US012735735B2

(12) United States Patent
Quiring et al.

(10) Patent No.: US 12,735,735 B2
(45) **Date of Patent: *Sep. 15, 2026**

(54) DIGITAL MICROBIOLOGY

(71) Applicants: BIO-RAD EUROPE GMBH, Basel (CH); BIO-RAD LABORATORIES, INC., Hercules, CA (US)

(72) Inventors: Christophe Quiring, Marnes la Coquette (FR); Christine Favier, Marnes-la-Coquette (FR); Patrice Sarfati, Marnes la Coquette (FR); Jean Francois Mouscadet, Marnes la Coquette (FR); Ronald Lebofsky, Sceaux (FR); Rebecca Dievart, Marnes la Coquette (FR)

(73) Assignee: BIO-RAD EUROPE GMBH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,860

(22) Filed: Apr. 8, 2024

(65) Prior Publication Data

US 2024/0336949 A1 Oct. 10, 2024

Related U.S. Application Data

(60) Continuation of application No. 17/686,466, filed on Mar. 4, 2022, now Pat. No. 11,952,610, which is a division of application No. 16/072,712, filed as application No. PCT/IB2017/000086 on Jan. 25, 2017, now Pat. No. 11,268,124.

(60) Provisional application No. 62/286,897, filed on Jan. 25, 2016.

(51) Int. Cl.

| | |
|---|---|
| ***C12Q 1/06*** | (2006.01) |
| ***C12N 9/26*** | (2006.01) |
| ***C12N 9/34*** | (2006.01) |
| ***C12N 9/38*** | (2006.01) |
| ***C12N 9/40*** | (2006.01) |
| ***C12N 9/42*** | (2006.01) |
| ***C12N 9/48*** | (2006.01) |
| ***C12Q 1/04*** | (2006.01) |

(52) U.S. Cl.

CPC ............. *C12Q 1/06* (2013.01); *C12N 9/2428* (2013.01); *C12N 9/2445* (2013.01); *C12N 9/2465* (2013.01); *C12N 9/2471* (2013.01); *C12N 9/2474* (2013.01); *C12N 9/485* (2013.01); *C12Q 1/04* (2013.01); *C12Q 1/045* (2013.01); *C12Y 302/01003* (2013.01); *C12Y 302/01022* (2013.01); *C12Y 302/01035* (2013.01); *C12Y 304/11* (2013.01)

(58) Field of Classification Search

CPC . C12Q 1/06; C12Q 1/04; C12Q 1/045; C12N 9/2428; C12N 9/2445; C12N 9/2465; C12N 9/2471; C12N 9/2474; C12N 9/485; C12Y 302/01003; C12Y 302/01022; C12Y 302/01035; C12Y 304/11

See application file for complete search history.

(56) References Cited

U.S. PATENT DOCUMENTS

| | | | |
|---|---|---|---|
| 4,399,219 | A | 8/1983 | Weaver |
| 4,401,755 | A | 8/1983 | Weaver |
| 4,643,968 | A | 2/1987 | Weaver |
| 4,959,301 | A | 9/1990 | Weaver et al. |
| 5,510,241 | A | 4/1996 | Thorns |
| 8,399,198 | B2 | 3/2013 | Hiddessen et al. |
| 9,012,390 | B2 | 4/2015 | Holtze et al. |
| 9,029,085 | B2 | 5/2015 | Agresti et al. |
| 9,068,210 | B2 | 6/2015 | Agresti et al. |
| 9,090,885 | B2 | 7/2015 | Boedicker et al. |
| 10,202,571 | B2 | 2/2019 | Boedicker et al. |
| 11,268,124 | B2 | 3/2022 | Quiring et al. |
| 11,952,610 | B2 | 4/2024 | Quiring et al. |
| 2005/0084923 | A1 | 4/2005 | Mueller et al. |
| 2010/0227767 | A1 | 9/2010 | Boedicker et al. |
| 2010/0317085 | A1 | 12/2010 | Boedicker et al. |
| 2011/0217711 | A1 | 9/2011 | Hiddessen et al. |
| 2015/0377869 | A1 | 12/2015 | Berkelman et al. |
| 2016/0039656 | A1 | 2/2016 | Walsh et al. |
| 2017/0022470 | A1 | 1/2017 | Calemczuk et al. |

FOREIGN PATENT DOCUMENTS

| | | |
|---|---|---|
| EP | 1 425 384 | 9/2002 |
| EP | 1 472 349 | 1/2003 |
| RU | 2569196 | 11/2015 |
| WO | WO 1989/010566 | 11/1989 |
| WO | WO 98/016830 | 4/1998 |
| WO | WO 2009/015390 | 1/2009 |
| WO | WO 2013/155525 | 10/2013 |

(Continued)

OTHER PUBLICATIONS

King AD Jr, Hocking AD, Pitt JI. Dichloran-rose bengal medium for enumeration and isolation of molds from foods. Appl Environ Microbiol. May 1979;37(5):959-64. doi: 10.1128/aem.37.5.959-964. 1979. PMID: 485140; PMCID: PMC243332 (Year: 1979).*

Boedicker, J. Q. et al. "Detecting bacteria and determining their susceptibility to antibiotics by stochastic confinement in nanoliter droplets using plug-based microfluidics" *Lab Chip*, Aug. 2008, pp. 1-15, vol. 8, No. 8.

Kang, D.-K. et al. "Rapid detection of single bacteria in unprocessed blood using Integrated Comprehensive Droplet Digital Detection" *Nature Communications*, Nov. 13, 2014, pp. 1-10, vol. 5.

Marcoux, P. R. et al. "Micro-confinement of Bacteria into w/o Emulsion Droplets for Rapid Detection and Enumeration" *Colloids and Surfaces A: Physiochemical and Engineering Aspects*, 2011, pp. 1-18, vol. 377, No. 1.

Written Opinion in International Application No. PCT/IB2017/000086, May 10, 2017, pp. 1-5.

(Continued)

*Primary Examiner* — Kade Ariani

(74) *Attorney, Agent, or Firm* — SALIWANCHIK, LLOYD & EISENSCHENK

(57) ABSTRACT

Methods, compositions, and kits are provided for rapidly analyzing microbial growth and/or number in a plurality of water-in-oil emulsion droplets.

13 Claims, 39 Drawing Sheets

(56) References Cited

FOREIGN PATENT DOCUMENTS

| | | |
|---|---|---|
| WO | WO 2014/138711 | 9/2014 |
| WO | WO 2015/015199 | 2/2015 |
| WO | WO 2015/048173 | 4/2015 |
| WO | WO 2015/150714 | 8/2015 |

OTHER PUBLICATIONS

Rothrock Jr., M. J. et al. "Quantification of Zoonotic Bacterial Pathogens within Commercial Poultry Processing Water Samples Using Droplet Digital PCR" *Advances in Microbiology*, 2013, pp. 403-411, vol. 3.

Naher, U.A et al. "Specific Growth Rate Sugar and Carbon Consumption of Diazotrophs Isolated from Rice Rhizosphere" *Journal of Biological Sciences*, 2008, pp. 1008-1014, vol. 8, No. 6.

Hammar, P. et al. "Single-cell screening of photosynthetic growth and lactate production by cyanobacteria" *Biotechnol Biofuels*., 2015, pp. 1-8, vol. 8, No. 193.

Courtois, F. et al. "Controlling the Retention of Small Molecules in Emulsion Microdroplets for Use in Cell-based Assays" *Anal. Chem*., Apr. 15, 2009, pp. 3008-3016, vol. 81, No. 8.

Furutani, S. et al. "Rapid Detection of *Salmonella enterica* in Food Using a Compact Disc-Shaped Device" *Micromachines*, 2016, pp. 1-9, vol. 7, No. 10.

Brouzes, E. et al. "Droplet microfluidic technology for single-cell high-throughput screening" *PNAS*, Aug. 25, 2009, pp. 14195-14200, vol. 106, No. 34.

Domingue, G. et al. "Bacterial doubling time modulates the effects of opsonisation and available iron upon interactions between *Staphylococcus aureus* and human neutrophils" *FEMS Immunology and Medical Microbiology*, 1996, pp. 223-228, vol. 16.

Giana, H. E. et al. "Rapid Identification of Bacterial Species by Fluorescence Spectroscopy and Classification Through Principal Components Analysis" *Journal of Fluorescence*, Nov. 2003, pp. 489-493, vol. 13, No. 6.

Bhatta, H. et al. "Use of Fluorescence Spectroscopy to Differentiate Yeast and Bacterial Cells" *Applied Microbiology and Biotechnology*, 2006, pp. 1-11, vol. 71, No. 1.

Dalterio, R. A. et al. "The Steady-State and Decay Characteristics of Primary Fluorescence From Live Bacteria" *Applied Spectroscopy*, 1987, pp. 234-241, vol. 41, No. 2.

Baraban, L. et al. "Millifluidic droplet analyser for microbiology" *Lab Chip*, 2011, pp. 4057-4062 and supplemental pp. 1-2, vol. 11.

Bian, X. et al. "A microfluidic drooplet digital PCR for simultaneous detection of pathogenic *Escherichia coli* O157 and *Listeria monocytogenes" Biosensors and Bioelectronics*, 2015, pp. 770-777, vol. 74.

Tanyeri, M. et al. "Detecting Single Bacterial Cells through Optical Resonances in Microdroplets" *Sens Lett*., Apr. 2008, pp. 326-329, vol. 6, No. 2.

Bao, N. et al. "Quantification of bacterial cells based on autofluorescence on a microfluidic platform" *Journal of Chromatography A*, available online Dec. 24, 2008, pp. 153-158, vol. 1181.

Funfak, A. et al. "Synergistic effects of metal nanoparticles and a phenolic uncoupler using microdroplet-based two-dimensional approach" *Journal of Environmental Monitoring*, 2011, pp. 410-415, vol. 13.

* cited by examiner

| MATRIX | FAT CONTENT | DROPLETS GENERATION |
|---|---|---|
| GROUND BEEF | 5% |  |
| GROUND BEEF | 15% |  |
| HAM | 25% |  |
| RAW WHOLE MILK | 4% |  |
| RAW MILK CAMENBERT | 22% |  |
| GRATED CARROTS | 0% |  |

DIGITAL MICROBIOLOGY

This application is a continuation of U.S. Ser. No. 17/686,466, filed Mar. 4, 2022, now U.S. Pat. No. 11,952,610, which is a divisional of U.S. Ser. No. 16/072,712, filed Jul. 25, 2018, now U.S. Pat. No. 11,268,124, which is the U.S. national stage application of International Patent Application No. PCT/IB2017/000086, filed Jan. 25, 2017, which claims the benefit of U.S. Provisional Application Ser. No. 62/286,897, filed on Jan. 25, 2016, the disclosures of which are hereby incorporated by reference in their entirety.

BACKGROUND

Identifying and/or quantifying microorganisms is relevant to many fields. Culturing the micro-organisms is a step in various assays and it takes one or more days to accomplish. Speeding up the culturing step would be a useful improvement to a variety of microbiological assays.

The food industry is subject to a plenitude of requirements for monitoring of numerous parameters of food safety. For example, food processors are generally required to analyze and control biological, chemical, and physical hazards from raw material production, procurement and handling, to manufacturing, distribution and consumption of the finished food product. One aspect of these requirements involves enumeration of microbial food quality indicators (QI). Such QI enumeration indicates the hygienic quality of the tested food. This hygienic quality information provides an indication of the likelihood of pathogenic organisms present in the food as well as the shelf life of the food. Exemplary QI enumeration techniques include colony counting and most probable number (MPN) techniques. Generally, such techniques can be prone to human error or inherent assay variability. Moreover, such techniques can require specialized reagents for enumeration of different target microorganisms. Furthermore, these techniques can require long incubation times (e.g., 18 to 24 hours or up to 5 days) before a result is obtained. Additionally, these techniques can require an undue amount of manual intervention.

In the clinical setting, pathogenic microorganisms can exhibit varying degrees of susceptibility to antimicrobial agents. Thus clinicians often benefit from identifying both the species or strain of pathogen and its susceptibility to various classes of antimicrobials and combinations thereof. However, methods for clinical assessment of microbial infections that are used in the art typically require at least 16-48 h to determine antimicrobial susceptibility. Moreover, typical antimicrobial susceptibility testing methods can be prone to human error or inherent assay variability. Additionally, these techniques can require specialized reagents for assessment of different target microorganisms. Additionally, these techniques can require an undue amount of manual intervention.

BRIEF SUMMARY OF THE INVENTION

Described herein are methods and compositions for determining the presence or absence of a microorganism in a sample. Also described herein are methods for rapidly assaying a food matrix for a number of target microorganisms per unit mass or volume. Additionally, methods (e.g., susceptibility tests) for rapidly assaying a target microorganism for a minimum inhibitory concentration of a test antimicrobial are described herein.

In an embodiment, a method for determining the presence or absence of a microorganism in a sample comprises i) encapsulating a sample in a plurality of water-in-oil emulsion droplets wherein the water-in-oil emulsion droplets further encapsulate a microbiological growth medium; ii) incubating the plurality of water-in-oil emulsion droplets at a temperature permissive of microbiological growth, and for a period of time sufficient to allow the target microorganisms to go through 5 to 45 doubling times; iii) identifying water-in-oil emulsion droplets comprising target microorganisms; and iv) responsive to identifying the target microorganism in at least one water-in-oil emulsion droplet, determining that the target microorganism is present in the sample.

BRIEF DESCRIPTION OF THE DRAWINGS

FIGS. 3A-30 illustrate rapid enumeration of *E. coli* from a ham food matrix using water-in-oil droplets.

FIGS. 21A and 21B show growth of *Mucor racemosus* CECT 20821 in YCG broth after 48 hours of incubation in the absence or in the presence, respectively, of dicloran in the oil phase.

FIGS. 23A and 23B show growth of *Aspergillus restrictus* CECT 20807 in YCG broth after 24 hours of incubation in the absence or in the presence, respectively, of dicloran in the oil phase. In FIG. 23A, the slide inlet is on the right side of the figure.

FIGS. 24A and 24B show growth of *Aspergillus restrictus* CECT 20807 in YCG broth after 48 hours of incubation in the absence or in the presence, respectively, of dicloran in the oil phase. In FIG. 24A, the slide inlet is on the right side of the figure.

FIGS. 25A and 25B show growth of *Penicillium hirsutum* ATCC 16025 in YCG broth after 24 hours of incubation in the absence or in the presence, respectively, of dicloran in the oil phase. The slide inlet is on the left side of FIG. 25A and the right side of FIG. 25B.

FIGS. 26A and 26B show growth of *Erotium rubrum* CECT 20807 in YCG broth after 24 hours of incubation in the absence or in the presence, respectively, of dicloran in the oil phase.

FIGS. 27A and 27B show growth of *Erotium rubrum* CECT 20807 in YCG broth after 48 hours of incubation in the absence or in the presence, respectively, of dicloran in the oil phase. In FIG. 27A, the slide inlet is on the right side of the figure.

FIGS. 29A and 29B show growth of *Fusarium graminearum* DSM 1096 in YCG broth after 48 hours of incubation in the absence or in the presence, respectively, of dicloran in the oil phase. In FIG. 29A, the slide inlet is on the right side of the figure.

FIGS. 30A and 30B show growth of *Aspergillus restrictus* CECT 20807 after 48 hours of incubation in the absence or presence, respectively, of rose bengal in the oil phase.

FIGS. 31A and 31B show growth of *Penicillium hirsutum* ATCC 16025 after 48 hours of incubation in the absence or presence, respectively, of Imazalil in the oil phase.

FIG. 32 is an image of droplets having *C. glabrata* and fluorescein-labeled Concanavalin A (ConA). FIG. 33 is an image of droplets having *C. tropicalis* and ConA.

FIG. 34 is an image of droplets having *E. coli* and ConA. FIG. 35 is a merged image of a visible image and a green fluorescence image from droplets having *C. krusei* and ConA.

FIGS. 39A and 40A are negative controls. Arrows show examples of droplets positive for the microorganism.

FIGS. 43A-45B illustrate the use of 5 (6)-carboxyfluorescein diacetate (CFDA) substrate for specific detection and/or enumeration of target microorganisms that express the esterase enzyme. FIGS. 43A and 43B show detection of *Candida albicans* ATCC 10231 in the absence and presence, respectively, of CFDA. FIGS. 45A and 45B show detection of *Zygosaccharomyces rouxii* DSM 7525 in the absence and presence, respectively, of CFDA. In each experiment, microorganisms were incubated 24 hours in YGC broth having 25 mg/L CFDA.

DETAILED DESCRIPTION OF THE INVENTION

I. Overview

Figure 1A:
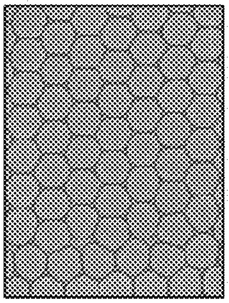
FIGS. 1A-1J illustrate results of a proof of concept experiment in which *E. coli* cells were partitioned into droplets, incubated at a growth period for the indicated times, and observed with either visible or fluorescent microscopy. The results indicate that bacteria can be detected in 6 h or less and strong autofluorescence can be detected in 8 h or less.
Figure 1B:
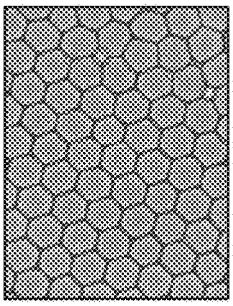
Figure 1C:
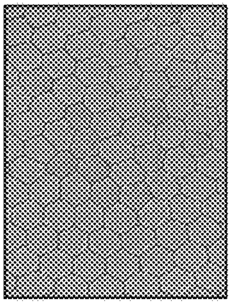
Figure 1D:
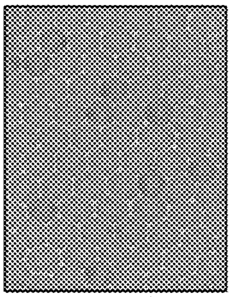
Figure 1E:
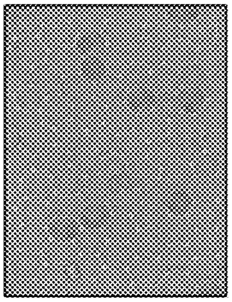
Figure 1F:
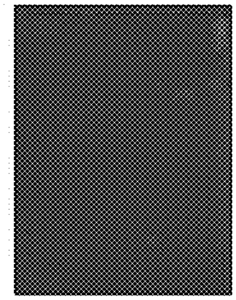
Figure 1G:
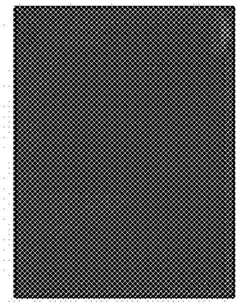
Figure 1H:
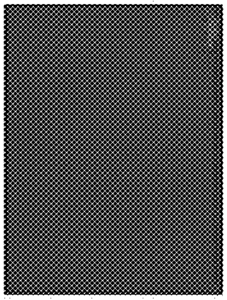
Figure 1I:
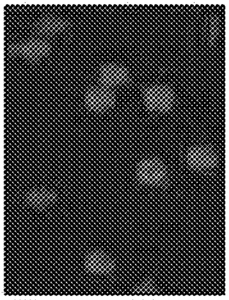
Figure 1J:
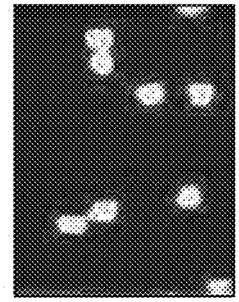
Figure 2A:
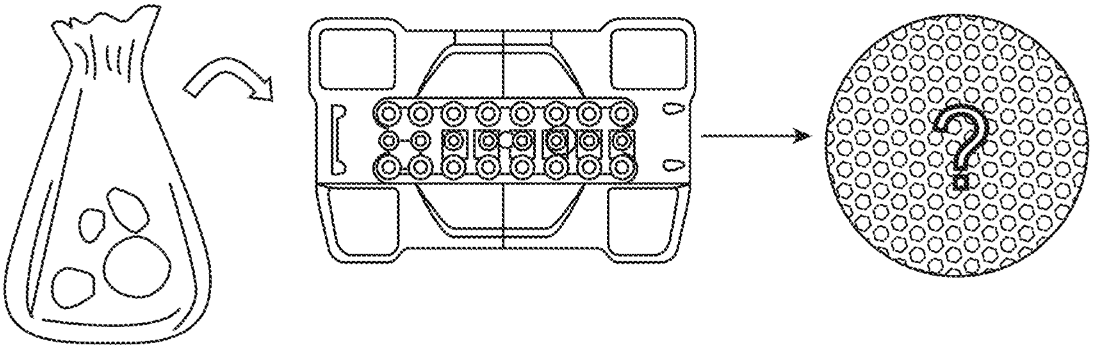
FIGS. 2A-2B illustrate results of an experiment in which the indicated food matrices were tested for compatibility with droplet generation.
Figure 2B:
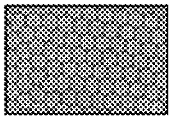
Figure 2B:
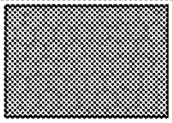
Figure 2B:
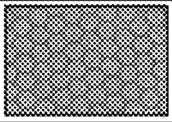
Figure 2B:
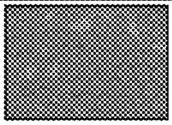
Figure 2B:
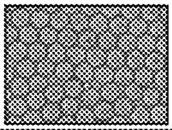
Figure 2B:
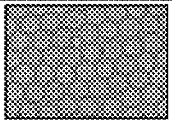
Figure 3A:
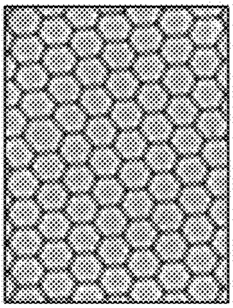
Figure 3B:
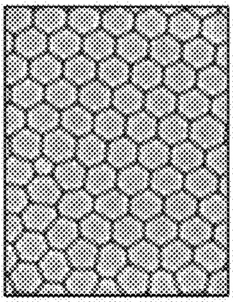
Figure 3C:
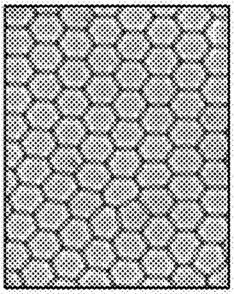
Figure 3D:
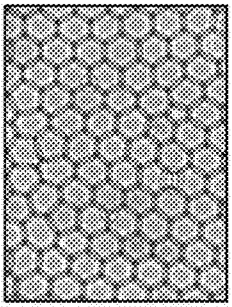
Figure 3E:
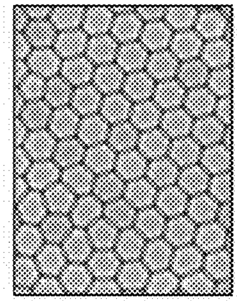
Figure 3F:
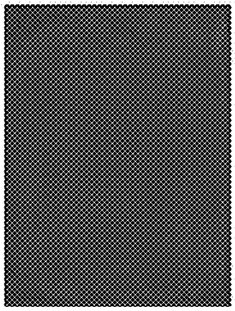
Figure 3G:
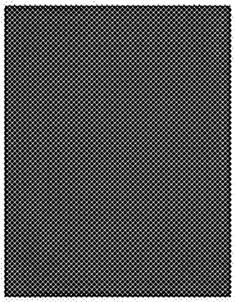
Figure 3H:
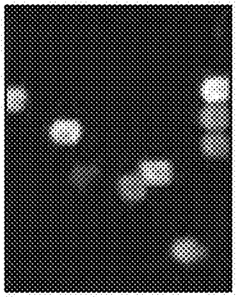
Figure 3I:
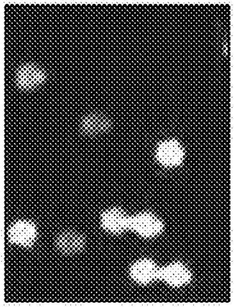
Figure 3J:
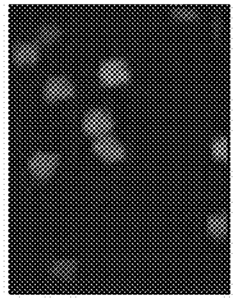
Figure 3K:
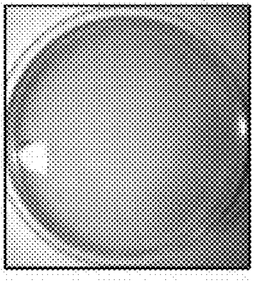
Figure 3L:
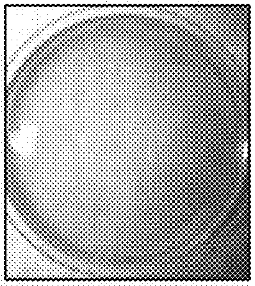
Figure 3M:
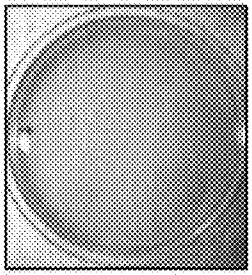
Figure 3N:
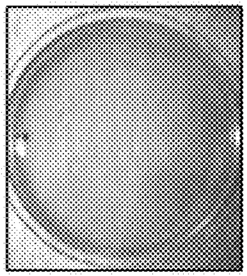
Figure 3O:
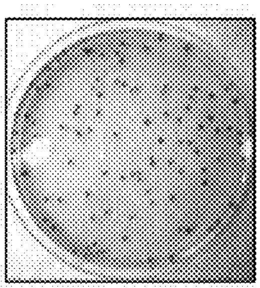
Figure 4A:
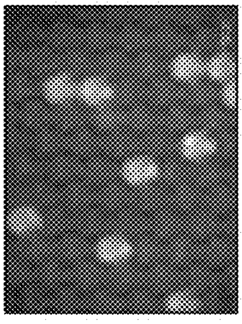
FIGS. 4A-4J illustrate rapid detection of various bacteria using water-in-oil droplets.
Figure 4B:
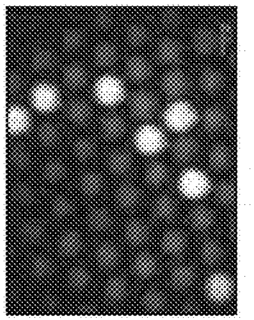
Figure 4C:
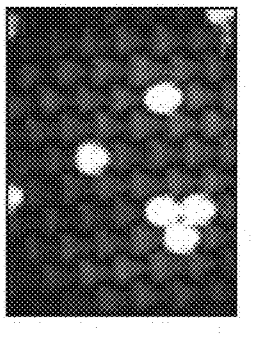
Figure 4D:
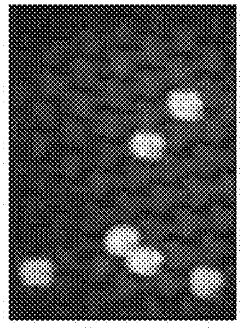
Figure 4E:
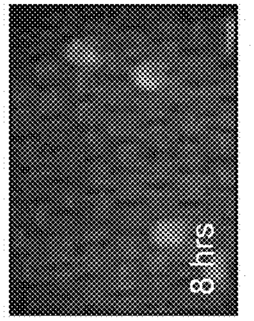
Figure 4F:
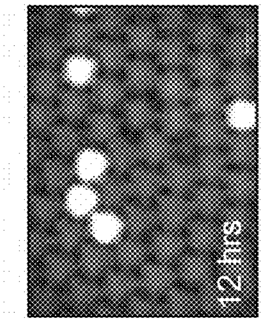
Figure 4G:
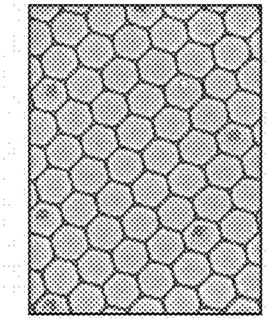
Figure 4H:
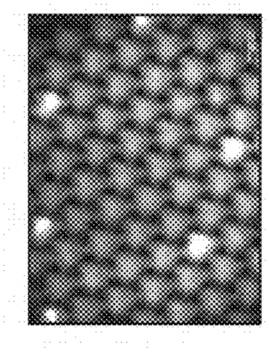
Figure 4I:
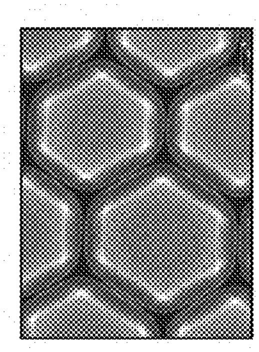
Figure 4J:
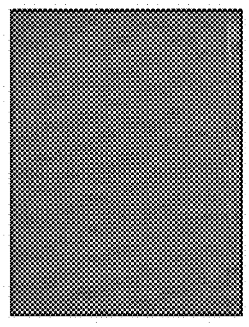
Figure 5A:
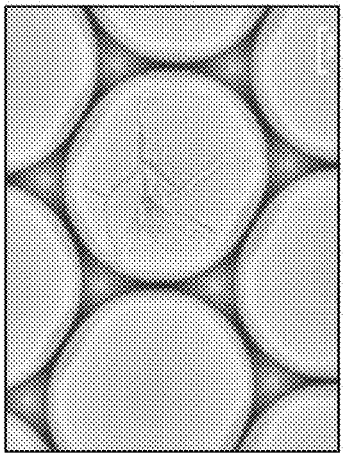
FIGS. 5A-5F illustrate rapid detection of various yeasts, and molds using water-in-oil droplets.
Figure 5B:
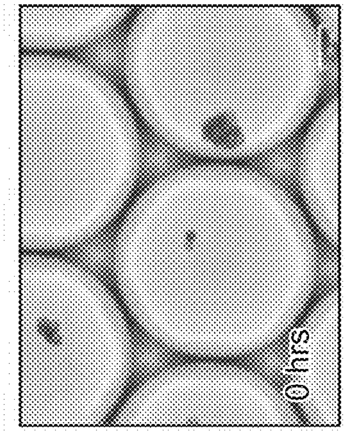
Figure 5C:
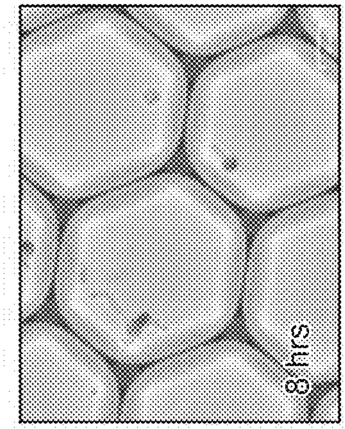
Figure 5D:
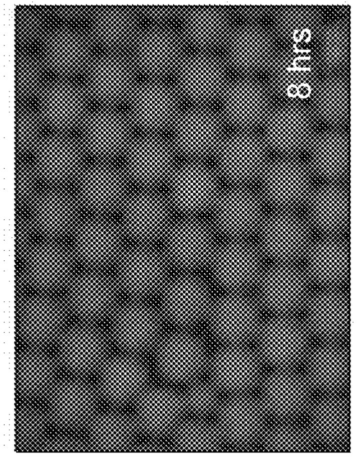
Figure 5E:
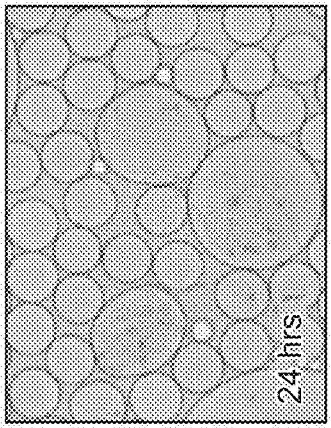
Figure 5F:
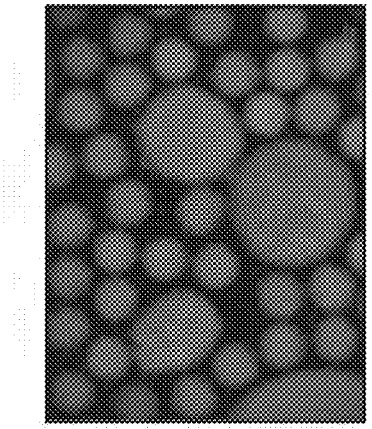

Described herein are methods, compositions, and kits where fewer doubling times are required in a culturing step allowing for analyzing rapidly the presence or absence of a microorganism and/or growth or number of microorganisms in a sample. These methods are useful in the areas of quality indicators (QI) for food and the environment and clinical diagnosis of microbial infections.

When analyzing food, the method is performed on any suitable food matrix from raw materials to finished food products. Food and food products include but are not limited to solid food and beverages, including water. QI enumeration for food also includes analysis of the environment in which food is prepared, processed and stored. Such environmental samples are samples taken from equipment, surfaces, etc. where food is being prepared, processed and stored. Examples include swabs of counters in a kitchen and slicing machinery.

The described methods compositions and kits are also useful for determining QI of the environment. Environments to be tested are any kind of environment where microorganisms, if present, would be detrimental to humans or animals. Such environments can be indoors or outdoors and include, but are not limited to, water used in recreation (e.g., swimming pool, lakes), farms and surfaces in buildings.

The methods, compositions, and kits described herein can also provide for rapid antimicrobial susceptibility testing and, optionally, specific identification without any incubation or within a small number of doubling times of the subject microorganism(s). Doubling time (also called mean generation time) is the time required for a given population (n) to double in number (2n) under optimal conditions of growth. Doubling times for various microorganisms are known and published in the literature. Optionally, identification of microorganisms is accomplished without any marker being added to enhance the signal of the identified microorganism (e.g., by autofluorescence). In other embodiments, reagents bind the target microorganism to aid in its identification and/or quantification.

This rapid assessment of microbial quality or antimicrobial susceptibility involves partitioning a sample containing one or more target microorganisms into a plurality of water-in-oil emulsion droplets containing an antibiotic to which susceptibility is to be tested, incubating the droplets for, or for at least, 1 to 35 (e.g., 1 to 30, 1 to 25, 1 to 20, 1 to 15, 1 to 10, 5 to 35, 5 to 30, 5 to 25, 5 to 20, 5 to 15, 5 to 10, 10 to 35, 10 to 30, 10 to 25, 10 to 20, 10 to 15) doubling times, and detecting the presence or absence of the target microorganisms in the droplets. In embodiments in which antimicrobial susceptibility is assessed, the droplets contain an antibiotic or an antifungal. In some embodiments, different concentrations of antimicrobial are tested. Which droplet contains which concentration of antibiotic is known by adding an identifier to each droplet. Such identifiers can be dyes or bar codes. In some embodiments, no incubation is used.

II. Compositions

Water-in-oil droplet chemistries described herein include droplets with skins and dual-phase surfactant droplets. As used herein, dual phase surfactant droplets contain an oil and an oil-phase surfactant as the non-aqueous phase and water and an aqueous-phase surfactant as the aqueous phase. Such water-in-oil droplets can be adapted for compatibility with: (i), microbial growth and culture media components; (ii), food matrices; (iii), detection reagents (e.g., a fluorescent detection reagent); (iv), antimicrobials; (v), clinical samples; or (vi), prolonged (e.g., greater than 4, 8, 24, or 36 h) incubation periods by enhancing stability, or a combination of two, three, four, or five of the foregoing. The inventors have surprisingly found that certain water-in-oil droplet chemistries described herein are compatible with a wide variety of food or clinical matrices. Moreover, the inventors have surprisingly found that certain water-in-oil droplet chemistries and methods of their use can provide improved QI enumeration, identification of microorganisms, and/or antimicrobial susceptibility results in a reduced amount of time. Additionally, surprisingly, certain microorganisms can be detected by detecting autofluorescence of droplets in which the microorganisms are grown thereby eliminating the need for addition of a detection reagent. Alternatively, an intercalating dye can be used to detect certain microorganisms. Surprisingly, certain dyes are effective without lysing the microorganism's cells and do not disrupt the cell growth.

A. Droplet with Skins Compositions

Water-in-oil emulsion droplets described herein include, but are not limited to, those that contain a "skin" or shell at an interface between an aqueous and a non-aqueous phase. Such skins are composed of skin-forming components. A skin-forming component is any substance or combination of substances that promotes formation of a skin near or at an aqueous/non-aqueous interface.

i. Skin-Forming Proteins

A skin-forming component can include at least one skin-forming protein. The skin forming protein can be provided in an aqueous phase prior to combining with a non-aqueous phase to form droplets. Alternatively, the skin forming component can be relatively hydrophobic and can therefore be provided in a non-aqueous phase prior to combining with an aqueous phase to form droplets. After combining of aqueous and non-aqueous phases, the skin-forming protein can be recruited to the aqueous/non-aqueous interface before or during skin formation.

The skin forming protein may be present at a concentration effective for detectable skin formation under skin formation conditions (e.g., heating). Exemplary effective concentrations include, but are not limited to, at least about 0.01% or 0.03%, 0.03% to 3%, 0.05% to 2%, 0.1% to 1%, or about 0.1% by weight. The protein may be a "nonspecific blocking" skin-forming protein or a "non-specific binding" skin-forming protein. The phrase "non-specific blocking" or "non-specific binding" as used herein refers generally to a capability to non-specifically bind to surfaces, that is, hydrophobic and/or hydrophilic surfaces, sometimes with the aid of heating. Non-specific blocking/binding proteins are typically water-soluble proteins, may be relatively large serum or milk proteins (among others), and/or may not interact with any of the other components of the aqueous phase in a specific binding fashion. Exemplary non-specific blocking/binding proteins that may be suitable as skin-forming proteins include, but are not limited to, albumins (such as a serum albumin (e.g., from bovine (BSA), human, rabbit, goat, sheep or horse, among others)), globulins (e.g., beta-lactoglobulin), casein, and gelatin (e.g., bovine skin gelatin type B), and fragments (e.g., proteolytic fragments) thereof.

ii. Aqueous Phase Surfactants

Water-in-oil emulsion droplets that contain a skin can be formed with an aqueous phase that contains a surfactant, a surface-active substance capable of reducing the surface tension of a liquid in which it is present. A surfactant can be a detergent and/or a wetting agent. In some embodiments, the surfactant contains a hydrophilic and a hydrophobic portion and is therefore amphipathic. The aqueous phase can include at least one non-ionic surfactant, at least one ionic surfactant, or at least one non-ionic and at least one ionic surfactant. Exemplary surfactants include, but are not limited to, block copolymers of polypropylene oxide and polyethylene oxide (e.g., poloxamers). Exemplary poloxamers include, but are not limited to, those sold under the trade names PLURONIC® and TETRONIC®. In some embodiments, the aqueous phase includes the surfactant PLURONIC® F-68. In some embodiments, the aqueous phase includes a water-soluble and/or hydrophilic fluorosurfactant. In some cases, the aqueous phase includes a fluorosurfactant sold under the trade name ZONYL®, such as a ZONYL® FSN fluorosurfactant. In some cases, the aqueous phase can include the surfactant polysorbate 20.

The concentration of a particular surfactant or total surfactant of an aqueous phase prior to, during, or after combining with a non-aqueous phase to form water-in-oil emulsion droplets with skins can be selected to stabilize emulsion droplets prior to skin formation (e.g., heating). An exemplary concentration of aqueous phase surfactant includes, but is not limited to, about 0.01% to about 10%, 0.05% to about 5%, 0.1% to about 1%, or 0.5% w/w, w/v, or v/v.

iii. Oil Phase

Water-in-oil emulsion droplets that contain a skin can be formed in, and/or formed by combining an aqueous phase with, a non-aqueous phase. The non-aqueous phase can be a continuous phase water-immiscible carrier fluid. Alternatively, the non-aqueous phase can be a dispersed phase. The non-aqueous phase can be referred to herein as an oil phase containing at least one oil, but may include additional liquid (or liquefiable) compounds or mixtures that are immiscible with water. The oil can be synthetic or naturally occurring. The oil can be a carbon-based (e.g., alkyl) and/or silicon-based (e.g., siloxane-based) oil. The oil can be a hydrocarbon and/or a silicone oil. The oil can be partially or fully fluorinated. The oil can be generally miscible or immiscible with one or more classes of organic solvents. Exemplary oils include, but are not limited to, at least one of silicone oil (e.g., polydimethylsiloxane), mineral oil, fluorocarbon oil, vegetable oil, or a combination thereof.

In an exemplary embodiment, the oil is a fluorinated or perfluorinated oil. A fluorinated oil can be a primary oil or an additive to a primary oil. Exemplary fluorinated oils include, but are not limited to, those sold under the trade name FLUORINERT®, such as FLUORINERT® electronic liquid FC-3283, FC-40, FC-43, FC-70, or combinations thereof. Additional or alternative exemplary fluorinated oils include, but are not limited to, those sold under the trade name NOVEC®, including NOVEC® HFE 7500 engineered fluid.

B. Dual Phase Surfactant Droplets

Dual phase surfactant droplet methods and compositions include, but are not limited to, those employing an oil phase containing a fluorosurfactant and an aqueous phase containing a non-ionic fluorosurfactant. In some cases, the oil is a fluorous oil. In some cases, the fluorosurfactant is non-ionic.

i. Oil Phase Fluorosurfactants

In some cases, the fluorosurfactant of the oil phase (e.g., fluorosurfactant of an oil phase containing a fluorous oil) is a triblock copolymer of Formula I:

Formula I

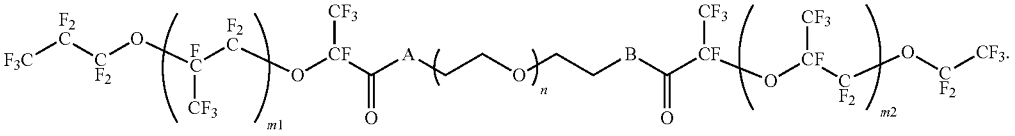

Formula I is a triblock copolymer containing polyethylene glycol (PEG) polymer covalently linked to a polyhexafluoropropylene (PFPE) at both ends. In one embodiment, the covalent linkage between the PEG block and PFPE blocks at both ends is an amide linkage (A and B are nitrogen). In another embodiment, the linkage between the PEG block and the two PFPE blocks is an ester linkage (A and B are oxygen). In another example, one end can be an ester linkage and one end an amide linkage (A is O, and B is N; or A is N, and B is O).

The lengths of the PFPE chains and the PEG block can affect the properties of the fluorosurfactant of Formula I. In some aspects of the present disclosure both $m_1$ and $m_2$ are independently in a range of about 10-100. In some cases both $m_1$ and $m_2$ are independently in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. In some cases $m_1$ is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. In some cases $m_2$ is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100.

The value of 'n' of Formula I may be in a range of about 10-60. In some cases the value of 'n' is in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, about 55-60. In some embodiments, each of $m_1$ and $m_2$ is about 35 and 'n' is about 22.

In some cases, the fluorosurfactant of the oil phase (e.g., fluorosurfactant of an oil phase containing a fluorous oil) is a polymer of Formula II:

Formula II

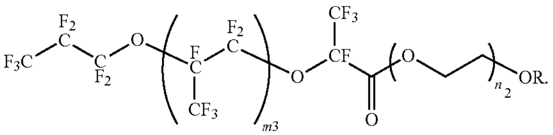

The surfactant of Formula II is a diblock copolymer of PEG and PFPE. The value of $m_3$, which represents the length of the PFPE block, is in a range of about 10-100. In some aspects, $m_3$ is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. The length of the PEG unit, '$n_2$' is in the range of about 10-60. In some cases the value of '$n_2$' is in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. The end of the PEG block, —OR, can either be a hydroxyl group (i.e., —OH), an alkoxy group, or an amine (R can be hydrogen, an alkyl group, or an amine).

In some cases, the fluorosurfactant of the oil phase (e.g., fluorosurfactant of an oil phase containing a fluorous oil) is a polymer of Formula III:

Formula III

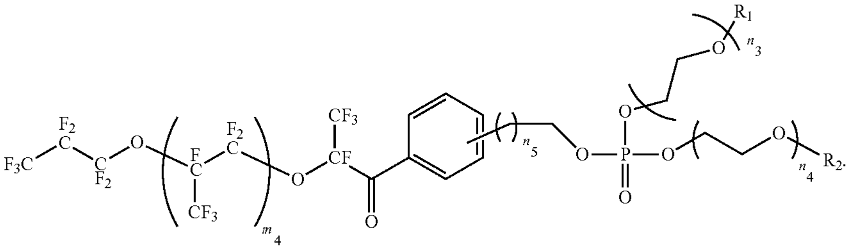

The surfactant of Formula III is a triblock copolymer wherein two units PEG (same or different length) and one unit of PFPE are connected by a phosphate linker ($PO_4$). The length of the PFPE chain $m_4$ is in a range of about 10-100. In some cases $m_4$ is in the range of about 10-20, about 10-30, about 10-40, about 10-50, about 10-60, about 10-70, about 10-80, about 10-90, about 20-30, about 20-40, about 20-50; about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. The lengths of the two PEG units, $n_3$ and $n_4$ are independently in a range of about 10-60. In some cases $n_3$ and $n_4$ are independently in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. In some cases $n_3$ is in the range of about 10-20, about 10-30, about 10-40, about 10-50, about 15-20, about 15-30, about 15-40, 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. In some cases $n_4$ is in the range of about 10-20, about 10-30, about 10-40, about 10-50, about 15-20, about 15-30, about 15-40, about 15-50, about 15-60, about 20-30, about 20-40, about 20-50, about 20-60, about 25-30, about 25-40, about 25-50, about 25-60, about 30-40, about 30-50, about 30-60, about 35-40, about 35-50, about 35-60, about 40-50, about 40-60, about 45-50, about 45-60, about 50-50, or about 55-60. The $CH_2$ spacer ($n_5$) can be 0, 1, 2 or 3 carbons in length.

In some cases, the fluorosurfactant contains a mixture of Formula I, Formula II, and/or Formula III. In some cases, the fluorosurfactant contains a mixture of Formula I and Formula II, a mixture of Formula I and Formula III, or a mixture of Formula II and Formula III. In some examples, the fluorosurfactant can comprise at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or about 99.9% (w/w) of a mixture of Formula I and Formula II. For example, the fluoro surfactant can comprise at least about 80%, about 90%, or 95% (w/w) of a mixture of Formula I and Formula II.

Further, the mixture of Formula I and Formula II can be in a ratio of greater than about 1:199, about 1:99, about 2:98, about 3:97, about 4:96, about 5:95, about 10:90, about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 96:4, about 97:3, about 98:2, about 99:1, or about 199:1 (w/w). For example, the mixture of Formula I and Formula II can be in a ratio of greater than about 80:20, about 90:10, or about 95:5 (w/w).

In certain examples, the mixture can further contain a compound of Formula XI:

Formula XI

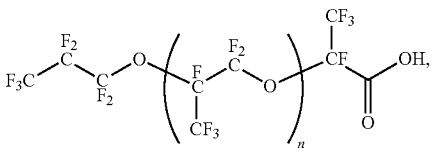

wherein n can be about 10 to 100, about 10 to 80, about 15 to 80, about 15 to 50, or about 20 to 50.

For example, the fluorosurfactant mixture can contain about 0.1% to 50%, about 0.1% to 20%, about 0.2% to 20%, about 0.2% to 10%, about 0.5% to 10%, about 0.5% to 5%, or about 1% to 5% (w/w) of Formula XI.

Further, the fluorosurfactant mixture can comprise greater than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the fluorosurfactant mixture can comprise greater than about 0.1% to about 0.5%, greater than about 1%, greater than about 2%, or about 5% (w/w) of Formula XI.

Alternatively, the fluorosurfactant mixture can comprise less than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the fluorosurfactant mixture can comprise less than about 1%, about 2%, about 5%, about 10%, or about 20% (w/w) of Formula XI.

In certain cases, the oil formulation can comprise less than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the oil formulation can comprise less than about 1%, about 2%, about 5%, about 10%, or about 20% (w/w) of Formula XI.

In other cases, the oil formulation can comprise greater than about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45% or about 50% (w/w) of Formula XI. For example, the oil formulation can comprise about greater than about 0.1%, about 0.5%, about 1%, about 2%, or about 5% (w/w) of Formula XI.

A surfactant can be characterized according to a Hydrophile-Lipophile Balance (HLB) value, which may be defined as the ratio of the molecular weight (MW) of the hydrophilic portion of the compound to the total MW of the compound. HLB can be controlled by varying the lengths/MWs of the hydrophobic portion (PFPE) and the hydrophilic portion (PEG) of the molecule. In some embodiments, droplets having oil-phase fluorosurfactants having longer (higher MW) perfluoropolyether chains can have increased resistance to thermally induced droplet coalescence.

In some embodiments, the MW of the perfluoropolyether chain is at least about 3000, at least about 4000, at least about 5000, at least about 6000, at least about 7000, at least about 8000, at least about 9000, or at least about 10000. In some other embodiments, the MW of the perfluoropolyether chain is about 3000, about 4000, about 5000, about 6000, about 7000, about 8000, about 9000, or about 10000.

In some aspects of the current disclosure, the HLB value of the fluoro surfactant is in the range of about 0-20. In some cases, the HLB values of the non-ionic surfactant ranges from about 0-10, about 0-20, about 5-10, about 5-15, about 5-20, or about 10-20. In some further aspects, the HLB value of the fluoro surfactant is about 1, about 2, about 3, about 4, about 5, about 6, about 7, about 8, about 9, about 10, about 11, about 12, about 13, about 14, about 15, about 16, about 17, about 18, about 19, or about 20.

In general, the fluoro surfactants obtained in the present disclosure are high purity fluorosurfactants and can be successfully used in microbial number and/or growth assays with while avoiding leaching of detection reagent and/or detectable or substantial inhibition of microbial growth. Inhibition of microbial growth can be detected by comparing doubling times of a target microorganism in bulk media of the same composition and temperature as the media and temperature used in the aqueous phase of a droplet. Generally, suitable levels of growth are within at least about 10% of the bulk doubling time.

In some cases, the fluorosurfactants can be greater than about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 85.5%, about 86%, about 86.5%, about 87%, about 87.5%, about 88%, about 88.5%, about 89%, about 89.5%, about 90%, about 90.5%, about 91.5%, about 92%, about 92.5%, about 93%, about 93.5%, about 94%, about 94.5%, about 95%, about 96.5%, about 97%, about 97.5%, about 98%, about 98.5%, about 99%, or about 99.5% weight percent (w/w) pure. In some examples, the fluorosurfactants are greater than about 90% weight percent (w/w) pure. For example, the fluorosurfactants can comprise at least 90% (w/w) of a mixture of Formula I and Formula II. In some cases the weight percent purity of the fluorosurfactant is in the range of about 90%-91% w/w, about 90%-92% w/w, about 90%-93% w/w, about 90%-94% w/w, about 90%-95% w/w, about 90%-96% w/w, about 90%-97% w/w, about 90%-98% w/w, about 90%-99% w/w, about 91%-92% w/w, about 91%-93% w/w, about 91%-94% w/w, about 91%-95% w/w, about 91%-96% w/w, about 91%-97% w/w, about 91%-98% w/w, 91%-99% w/w, about 92%-93% w/w, about 92%-94% w/w, about 92%-95% w/w, about 92%-96% w/w, about 92%-97% w/w, about 92%-98% w/w, about 92%-99% w/w, about 93%-94% w/w, about 93%-95% w/w, about 93%-96% w/w, about 93%-97% w/w, about 93%-98% w/w, about 93%-99% w/w, about 94%-95% w/w, about 94%-96% w/w, about 94%-97% w/w, about 94%-98% w/w, or about 94%-99% w/w.

In some cases the fluorosurfactants are greater than about 95% (weight percent) pure. For example, the fluorosurfactants can comprise at least 95% (w/w) of a mixture of Formula I and Formula II. In some cases the weight percent purity of the fluorosurfactant is in the range of about 95%-96% w/w, about 95%-97% w/w, about 95%-98% w/w, about 95%-99% w/w, about 96%-97% w/w, about 96%-98% w/w, about 96%-99% w/w, about 97%-98% w/w, about 97%-99% w/w, or about 98%-99% w/w. In some cases, the fluorosurfactants may have weight percent purity of about 90% w/w, about 91% w/w, about 92% w/w, about 93% w/w, about 94% w/w, about 95% w/w, about 96% w/w, about 97% w/w, about 98% w/w, or about 99% w/w.

The concentration of fluorosurfactant can affect droplet stability. In some cases, the concentration of fluorosurfactant can be in a range of 0.1-10.0 mM. In some embodiments, the concentration of fluorosurfactant is in a range of about 0.1 mM-1.0 mM, about 0.1 mM-2.0 mM, about 0.1 mM-3.0 mM, about 0.1 mM-4.0 mM, about 0.1 mM-5.0 mM, about 0.1 mM-6.0 mM, about 0.1 mM-7.0 mM, about 0.1 mM-8.0 mM, about 0.1 mM-9.0 mM, about 0.5 mM-1.0 mM, about 0.5 mM-2.0 mM, about 0.5 mM-3.0 mM, about 0.5 mM-4.0 mM, about 0.5 mM-5.0 mM, about 0.5 mM-6.0 mM, about 0.5 mM-7.0 mM, about 0.5 mM-8.0 mM, about 0.5 mM-9.0 mM, about 0.5 mM-10.0 mM, about 1.0 mM-2.0 mM, about 1.0 mM-3.0 mM, about 1.0 mM-4.0 mM, about 1.0 mM-5.0 mM, about 1.0 mM-6.0 mM, about 1.0 mM-7.0 mM, about 1.0 mM-8.0 mM, about 1.0 mM-9.0 mM, about 1.0 mM-10.0 mM, about 1.5 mM-2.0 mM, about 1.5 mM-3.0 mM, about 1.5 mM-4.0 mM, about 1.5 mM-5.0 mM, about 1.5 mM-6.0 mM, about 1.5 mM-7.0 mM, about 1.5 mM-8.0 mM, about 1.5 mM-9.0 mM, about 1.5 mM-10.0 mM, about 2.0 mM-3.0 mM, about 2.0 mM-4.0 mM, about 2.0 mM-5.0 mM, about 2.0 mM-6.0 mM, about 2.0 mM-7.0 mM, about 2.0 mM-8.0 mM, about 2.0 mM-9.0 mM, about 2.0 mM-10.0 mM, about 2.5 mM-3.0 mM, about 2.5 mM-4.0 mM, about 2.5 mM-5.0 mM, about 2.5 mM-6.0 mM, about 2.5 mM-7.0 mM, about 2.5 mM-8.0 mM, about 2.5 mM-9.0 mM, about 2.5 mM-10.0 mM, about 3.0 mM-4.0 mM, about 3.0 mM-5.0 mM, about 3.0 mM-6.0 mM, about 3.0 mM-7.0 mM, about 3.0 mM-8.0 mM, about 3.0 mM-9.0 mM, about 3.0 mM-10.0 mM, about 3.5 mM-4.0 mM, about 3.5 mM-5.0 mM, about 3.5 mM-6.0 mM, about 3.5 mM-7.0 mM, about 3.5 mM-8.0 mM, about 3.5 mM-9.0 mM, about 3.5 mM-10.0 mM, about 4.0 mM-5.0 mM, about 4.0 mM-6.0 mM, about 4.0 mM-7.0 mM, about 4.0 mM-8.0 mM, about 4.0 mM-9.0 mM, about 4.0 mM-10.0 mM, about 4.5 mM-5.0 mM, about 4.5 mM-6.0 mM, about 4.5 mM-7.0 mM, about 4.5 mM-8.0 mM, about 4.5 mM-9.0 mM, about 4.5 mM-10.0 mM, about 5.0 mM-6.0 mM, about 5.0 mM-7.0 mM, about 5.0 mM-8.0 mM, about 5.0 mM-9.0 mM, about 5.0 mM-10.0 mM, about 5.5 mM-6.0 mM, about 5.5 mM-7.0 mM, about 5.5 mM-8.0 mM, about 5.5 mM-9.0 mM, about 5.5 mM-10.0 mM, about 6.0 mM-7.0 mM, about 6.0 mM-8.0 mM, about 6.0 mM-9.0 mM, about 6.0 mM-10.0 mM, about 6.5 mM-7.0 mM, about 6.5 mM-8.0 mM, about 6.5 mM-9.0 mM, about 6.5 mM-10.0 mM, about 7.0 mM-8.0 mM, about 7.0 mM-9.0 mM, about 7.0 mM-10.0 mM, about 7.5 mM-8.0 mM, about 7.5 mM-9.0 mM, about 7.5 mM-10.0 mM, about 8.0 mM-9.0 mM, about 8.0 mM-10.0 mM, about 8.5 mM-9.0 mM, about 8.5 mM-10.0 mM, about 9.0 mM-10.0 mM, or about 9.5 mM-10.0 mM. In some embodiments, the concentration of fluorosurfactant is about 0.5 mM, about 1.0 mM, about 1.5 mM, about 2.0 mM, about 2.5 mM, about 3.0 mM, about 3.5 mM, about 4.0 mM, about 4.5 mM, about, 5.0 mM, about 5.5 mM, about 6.0 mM, about 6.5 mM, about 7.0 mM, about 7.5 mM, about 8.0 mM, about 8.5 mM, about 9.0 mM, or about 9.5 mM.

ii. Oil Phase

The oil phase or the continuous phase used for the dual-phase water-in-oil droplets can be any liquid compound or mixture of liquid compounds that is immiscible with water. The oil used can be or include, but is not limited to, at least one of silicone oil, mineral oil, hydrocarbon oil, fluorocarbon oil, vegetable oil, or a combination thereof. Any other suitable components can also be present in the oil phase, such as at least one surfactant, reagent, other additive, preservative, particles, or any combination thereof.

In some cases, the oil is fluorinated oil. Fluorinated oil can be any fluorinated organic compound. In some cases, the fluorinated oil is perfluorocarbon, such as perfluorooctane or perfluorohexane. In some cases, the fluorine-containing compound is a partially fluorinated hydrocarbon, such as 1,1,1-trifluorooctane or 1,1,1,2,2-petantafluorodecane. The fluorinated organics can be linear, cyclic or heterocyclic. In addition to carbon and fluorine, the fluorinated organic compound can further contain hydrogen, oxygen, nitrogen, sulfur, chlorine, or bromine atoms, or combinations thereof.

In some cases, the fluorinated oil is a perfluoroalkyl ether like methyl nonafluoroisobutyl ether sold as NOVEC™ HFE-7100 Engineered Fluid. In some cases, the fluorine containing compound is an ethoxy-nonafluorobutane, or the ethoxy-nonafluorobutane mixture, sold as NOVEC™ HFE-7200 Engineered Fluid. In some cases, the fluorine-containing compound is 3-ethoxy-1,1,1,2,3,4,4,5,5,6,6,6-dodecafluoro-2-trifluoromethyl-hexane, sold as NOVEC™ HFE-7500 Engineered Fluid. In some cases, the fluorine-containing compound can be 1,1,1,2,2,3,4,5,5,5-decafluoro-3-methoxy-4-trifluoromethyl-pentane, sold as NOVEC™ HFE-7300 Engineered Fluid.

In some embodiments, the fluorosurfactants reside mainly in the oil phase. In some cases at least about 90%, about 91%, about 92%, about 93%, about 94%, about 95%, about 96%, about 97%, about 98%, or about 99% of the fluorosurfactant resides in the oil phase.

iii. Aqueous Phase

The aqueous phase can contain any liquid or liquefiable component that when mixed with water at room temperature, forms a stable single phase aqueous solution. In some embodiments the aqueous phase can comprise one or more physiologically acceptable reagents and/or solvents etc. at a concentration that is compatible with microbial growth and/or enumeration. Some non-limiting examples of aqueous phase components include water, DMF, DMSO, methanol or ethanol. The aqueous phase can also include a buffering agent as described below. In some embodiments, the aqueous phase may include particles, such as beads. The aqueous phase may also include vehicles that provide for delayed release of reagents.

iv. Non-Ionic Non-Fluorosurfactant

The aqueous phase of the dual phase water-in-oil droplets can contain a non-ionic non-fluorosurfactant. In some embodiments, the non-ionic non-fluoro surfactant is a polyalkylene oxide block copolymer surfactant. In some cases, the non-ionic non-fluoro surfactant is a block copolymer of polypropylene glycol ($H-(O-CH(CH_3)-CH_2)_n-OH$, PPG) and polyethylene glycol ($H-(O-CH_2-CH_2)_n-OH$, PEG) having the general formula [$PPG_n$-$PEG_m$].

The non-ionic non-fluorosurfactant can be a di, tri, tetra, penta or even higher block polymer of PEG and PPG. In some cases the non-ionic non-fluorosurfactant is an alternating copolymer with regular alternating PEG and PPG units of general formula $(PEG\text{-}PPG)_x$, wherein x is in the range of about 10-100. In some cases, x is in the range of about 10-20, about 10-30, about 10-40, about 10-50, about 10-60, about 10-70, about 10-80, about 10-90, about 20-30, about 20-40, about 20-50, about 20-60, about 20-70, about 20-80, about 20-90, about 20-100, about 30-40, about 30-50, about 30-60, about 30-70, about 30-80, about 30-90, about 30-100, about 40-50, about 40-60, about 40-70, about 40-80, about 40-90, about 40-100, about 50-60, about 50-70, about 50-80, about 50-90, about 50-100, about 60-70, about 60-80, about 60-90, about 60-100, about 70-80, about 70-90, about 70-100, about 80-90, about 80-100, or about 90-100. In some cases the non-ionic non-fluorosurfactant is a random copolymer of PEG and PPG with the monomeric PEG and PPG blocks attached in a random sequence.

In some cases the molecular weight of PEG and PPG block copolymer is in the range of about 4,000 daltons ("Da")-25,000 Da. In some cases the molecular weight of the non-ionic non-fluorosurfactant is in the range of about 10,000 Da-25,000 Da; about 15,000 Da-25,000 Da; about 20,000 Da-25,000 Da; about 4,000 Da-20,000 Da; about 10,000 Da-20000 Da; about 15,000 Da-20,000 Da; about 4,000 Da-15,000 Da; about 10,000 Da-15,000 Da; or about 4,000 Da-10,000 Da. In some cases the molecular weight of the non-ionic non-fluorosurfactant is about 4,000 Da; about 4,500 Da; about 5,000 Da; about 5,500 Da; about 6,000 Da; about 6,500 Da; about 7,000 Da; about 7,500 Da; about 8,000 Da; about 8,500 Da; about 9,000 Da; about 9,500 Da; about 10,000 Da; about 10,500 Da; about 11,000 Da; about 11,500 Da; about 12,000 Da; about 12,500 Da; about 13,000 Da; about 13,500 Da; about 14,000 Da; about 14,500 Da; about 15,000 Da; about 15,500 Da; about 16,000 Da; about 16,500 Da; about 17,000 Da; about 17,500 Da; about 18,000 Da; about 18,500 Da; about 19,000 Da; about 19,500 Da; about 20,000 Da; about 20,500 Da; about 21,000 Da; about 21,500 Da; about 22,000 Da; about 22,500 Da; about 23,000 Da; about 23,500 Da; about 24,000 Da; about 24,500 Da; or about 25,000 Da.

In some cases, the non-ionic non-fluorosurfactant is a triblock copolymer of polypropylene oxide and polyethylene oxide, known as a poloxamer. In some cases the non-ionic non-fluorosurfactant is a poloxamer sold under the trade name PLURONIC® or TETRONIC®. In some embodiments, the Pluronic® surfactant is Pluronic® F-38, Pluronic® F-68, Pluronic® F-77, Pluronic® F-87, Pluronic® F-88, Pluronic®F-98, Pluronic® F-108 or Pluronic® F-127 (a=101, b=56).

In some embodiments the non-ionic non-fluorous surfactant is Nonidet® P40. The general structure of Nonidet® includes a hydrophilic polyethylene chain and an aromatic hydrocarbon lipophilic group as depicted in Formula VII:

Formula VII

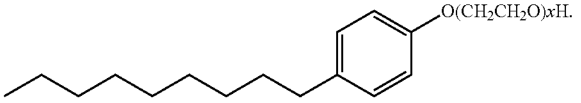

In some cases, the non-ionic non-fluorous surfactant can be a polyethylene glycol derivative. In some cases, the non-ionic non-fluorous surfactant is a polyethylene glycol derivative of Formula VIII:

Formula VIII

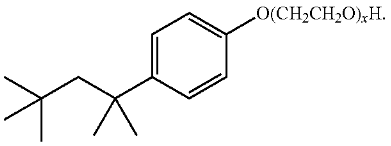

Exemplary non-ionic non-fluorous polyethylene glycol derivative surfactants of Formula VIII include, but are not limited to, Triton® surfactants. Exemplary Triton® surfactants include, but are not limited to, Triton® X-15 (x=1.5 avg), Triton® X-35 (x=3 avg), Triton® X-45 (x=4.5 avg), Triton® X-100 (x=9.5 avg), Triton® X-102 (x=12 avg), Triton® X-114 (x=7.5 avg), Triton® X-165 (x=16 avg), Triton® X-305 (x=30 avg), Triton® X-405 (x=35 avg), or Triton® X-705 (x=1.5 avg).

In some embodiments, the non-ionic non-fluorous surfactant is a polyoxyethylene derivative of sorbitan monolaurate of Formula IX:

Formula IX

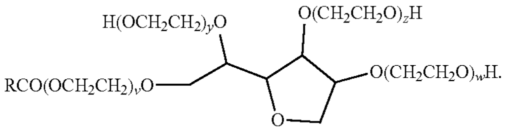

$v+w+y+z=20$

Exemplary polyoxyethylene derivatives of sorbitan monolaurate of Formula IX include, but are not limited to those commercially available under the trade name Tween®. In some cases, the non-ionic non-fluorous surfactant is Tween® 20 (R=$CH_2$ $(CH_2)_9CH_3$)), Tween® 40 (R=$CH_2$ $(CH_2)_{13}CH_3$), Tween® 60 (R=$CH_2$ $(CH_2)_{15}CH_3$) or Tween®-80 (R= $(CH_2)_7CH{=}CH(CH_2)_8$.

The concentration of non-ionic non-fluorosurfactant can be in a range of about 0.1-5.0% weight percent. In some embodiments the concentration of the non-ionic non-fluorosurfactant is less than about 1.5% weight by weight ("w/w"). In some cases, the concentration of Pluronic® is less than about 1.4% w/w, about 1.3% w/w, about 1.2% w/w, about 1.1% w/w, about 1.0% w/w, about 0.9% w/w, about 0.8% w/w, about 0.7% w/w, about 0.6% w/w, about 0.5% w/w, about 0.4% w/w, about 0.3% w/w, about 0.2% w/w or about 0.1% w/w. In some embodiments the Pluronic® F-98 concentration is in the range of about 0.50% w/w-1.5% w/w. In some embodiments the Pluronic® F-98 concentration is in the range of about 0.50% w/w-0.60% w/w, about 0.50% w/w-0.65% w/w, about 0.50% w/w-0.70% w/w, about 0.55% w/w-0.60% w/w, about 0.55% w/w-0.65% w/w, about 0.55% w/w-0.70% w/w, about 0.55% w/w-0.75% w/w, about 0.60% w/w-0.65% w/w, about 0.60% w/w-0.70% w/w, about 0.60% w/w-0.75% w/w, about 0.65% w/w-0.70% w/w, about 0.65% w/w-0.75% w/w, or about 0.70% w/w-0.75% w/w. In some further embodiments the concentration of the non-ionic non-fluorous surfactant can be adjusted to optimize the droplet stability and droplet size without inhibiting the microbial enumeration or microbial growth assay.

In some embodiments, the concentration of the fluorosurfactant is in a range of about 1.0-6.0 mM and the concentration of non-ionic non-fluorosurfactant is in a range of about 0.1%-3.0% weight percent. In a further embodiment, the fluorosurfactant has a structure of Formula I and a concentration of about 2.5 mM, and the non-ionic non-fluoro surfactant is Pluronic® F-98 and has a concentration of about 0.5% w/w-1.5% w/w. In some cases, the fluorosurfactant has a structure of Formula I and a concentration of about 2.5 mM, and the non-ionic non-fluorosurfactant is Pluronic® F-98 and has a concentration of about 0.50% w/w-0.60% w/w, about 0.50% w/w-0.65% w/w, about 0.50% w/w-0.70% w/w, about 0.55% w/w-0.60% w/w, about 0.55% w/w-0.65% w/w, about 0.55% w/w-0.70% w/w, about 0.55% w/w-0.75% w/w, about 0.60% w/w-0.65% w/w, about 0.60% w/w-0.70% w/w, about 0.60% w/w-0.75% w/w, about 0.65% w/w-0.70% w/w, about 0.65% w/w-0.75% w/w, or about 0.70% w/w-0.75% w/w.

In some embodiments, the non-ionic non-fluorous surfactants reside essentially in the aqueous phase. In some cases at least about 90%, about 91%, about 92%, about 93%, about 94%, about 95%, about 96%, about 97%, about 98%, or about 99% of the non-ionic non-fluorous surfactant resides in the aqueous phase of the water-in-oil emulsion droplets.

C. Droplet Salts and Buffering Agents

The aqueous phase of water-in-oil droplets described herein (e.g., droplets with skins and/or dual phase droplets) can include a variety of salts, buffering agents, microbial growth media components, detection reagents (e.g., dyes, probes, or fluorogenic or colorimetric substrates), microorganisms, food matrices, and/or any additional components necessary to determine microbial growth and/or numbers. All such additional components can be selected to be compatible with the intended assay.

Suitable buffer(s) or buffering agent(s) may be present in the aqueous phase. The buffer or buffering agent may be configured to maintain the pH of the aqueous phase near or at any suitable pH, such as a pH near or at which microbial growth and/or detection is optimal. For example, the pH may be selected to be at or near an optimum pH for an enzyme activity that can be detected by a fluorogenic or colorimetric substrate. As another example, the pH may be selected to be at or near an optimum pH for growth of a target microorganism. As yet another example, the pH, buffering agent, and/or concentration of buffering agent can be selected to provide for a detectable pH reduction caused by microbial growth, e.g., with a pH sensitive fluorophore. Similarly, suitable salts that may be present in the aqueous phase include, but are not limited to, salts compatible with microbial growth and/or detection. Exemplary salts include, but are not limited to, any one or combination of NaCl, KCl, $CaCl_2$, $MgCl_2$, $MgSO_4$, phosphate salts, and the like.

In some cases, the concentration of potassium salt (e.g., KCl) and/or sodium salt (e.g., NaCl) can be about, more than about, or less than about 10 mM, about 20 mM, about 30 mM, about 40 mM, about 50 mM, about 60 mM, about 80 mM, about 100 mM, about 200 mM. In some cases, the concentration of magnesium salt (e.g., $MgCl_2$) is at a concentration of about, more than about, or less than about 1.0 mM, about 2.0 mM, about 3.0 mM, about 4.0 mM, or about 5.0 mM. In some cases, the buffering agent is about, is more than about, or is less than about 1 mM, 5 mM, 10 mM, 15 mM, 20 mM, 30 mM, 50 mM, 80 mM, 160 mM, or 200 mM.

In some cases, the pH may, for example, approximate a physiological pH, such as about 5 to 9, 5 to 6.5, 6.5 to 8.5, 7 to 8, or about 7.5 among others. A particular buffering agent may be selected that has a pKa relatively close to the desired pH to be maintained and that is compatible with the reaction(s) to be performed. The buffering agent may be physiologically compatible. Exemplary buffering agents that may be suitable include, but are not limited to, Tris (2-Amino-2-hydroxymethyl-propane-1,3-diol), MES (2-(N-morpholino) ethanesulfonic acid), MOPS (3-morpholino-propane-1-sulfonic acid), HEPES (2-[4-(2-hydroxyethyl) piperazin-1-yl] ethanesulfonic acid), and the like. In some cases, the buffering agent is, or includes, a phosphate buffer, such as a mono-, di-, and/or tri-basic sodium or potassium phosphate buffer, or a combination thereof. In some cases, a buffering agent is inherently provided by one or more components of a minimal, complex, defined and/or undefined microbial medium. For example, components of tryptones, various peptones, phytones, amino acid mixtures, physiological sodium, potassium, or magnesium salts, etc., can provide sufficient buffering capacity for the methods and compositions of the present invention. Alternatively, in some cases, although minimal, complex, defined and/or undefined microbial media can provide buffering capacity, an additional buffering agent, such as one or more of the foregoing buffering agents is included in the aqueous phase of the water-in-oil droplets.

F. Droplet Growth Media

A wide variety of growth media can be selected as a component of the aqueous phase of the water-in-oil droplets. The word medium (also referred to as growth or culture media) as used herein includes any medium used for microbiological culture including defined and undefined components. Typically, a growth medium suitable for, compatible with, or optimal for, growth of the one or more target microorganisms to be enumerated or assayed for antimicrobial susceptibility is selected. Generally, the growth medium will contain a nitrogen source, a carbon source, and various essential elements.

The nitrogen source can be, or include, a protein, or mixture of proteins. For example, the nitrogen source can be beef extract, or yeast extract. The nitrogen source can be, or include, a partially or fully hydrolyzed protein or mixture of proteins such as peptone, tryptone, casamino acids, etc. The nitrogen source can be, or include, an amino acid or mixture of amino acids. In some cases, the nitrogen source is a nitrogen (e.g., nitrate) salt, such as ammonium sulfate.

The carbon source can be, or include, glucose, galactose, arabinose, succinate, glycerol, pyruvate, glutamate, xylose or a combination thereof. In some cases, in complex media containing one or more undefined nitrogen sources (e.g., beef extract, yeast extract, tryptone, or peptone), the carbon source is an inherent component of the undefined nitrogen source. Essential elements include, but are not limited to, sodium, potassium, calcium, magnesium, iron, nitrogen, phosphorous, and sulfur.

Exemplary growth media for use in an aqueous phase of water-in-oil emulsion droplets include, but are not limited to, tryptone-soya broth (TSB), buffered peptone water (e.g., BAM Media M192), and combinations thereof. In some cases, a selective media is used as a component of the aqueous phase of the water-in-oil emulsion droplets. Such selective media include, but are not limited to, chromogenic media, BairdParker, bromcresol purple ("BCP") agar, bile esculin agar ("BEA") agar, Bryant and Burkey's medium, buffered peptone water, chapman's medium, chocolate agar, cystine lactose electrolyte deficient ("CLED") agar, coletsos, columbia agar, Drigalski agar, Fraser, Granada, GVPC agar, Hektoen agar, king A & B, Lowenstein-Jensen, LT100, mac conkey agar, MRS broth or agar, mueller Hinton broth or agar, Müller-Kauffmann, listeria identification agar base ("PALCAM"), PCB, RPMI, RVS, Sabouraud, Schaedler broth or agar, selenite broth, Slanetz and Bartley's medium, SPS agar, TGY, TSB, TSI, TTC tergitol, VRBG, XLD, etc.

G. Droplet Antimicrobials

In some aspects the aqueous phase of the water-in-oil emulsion droplets can contain an antimicrobial. The antimicrobial can be included to ensure that the assay is not confounded by the presence of confounding microorganisms. For example, if QI enumeration is desired, where the target microorganisms are bacteria, then an antifungal agent can be included in the aqueous phase to avoid growth of fungi which are non-targeted organisms. As another example, if QI enumeration is desired, where the target microorganisms are fungi or molds, then an antibacterial agent can be included in the aqueous phase. Alternatively, the antimicrobial can be included to assess antimicrobial susceptibility of a target microorganism, or class of target microorganisms. For example, a minimum inhibitory concentration (MIC) against an antimicrobial can be determined by assaying the growth of target microorganism(s) with at least two (e.g., 3-10) different concentrations of the test antimicrobial in the aqueous phase. There can also be many more different concentrations such as when using a gradient of antimicrobial concentrations in the droplets. The gradient of concentrations can be linear or non-linear. In another example, one concentration is used when determining whether a microorganism is susceptible to the test antimicrobial. The one concentration selected is a breakpoint concentration that differentiates the susceptible organisms from those that are not susceptible.

A wide variety of antimicrobials can be employed in the aqueous phase of the water-in-oil emulsion droplets. Generally, the antimicrobials are selected to not disturb the existence of the droplets. For example, antimicrobials that reside essentially in the aqueous phase and do not substantially compartmentalize to the non-aqueous phase can be selected. Alternatively, partial partitioning of the antimicrobial to the oil phase can be accounted for before determining the MIC of the antimicrobial. As yet another alternative, the antimicrobial can be included in both the oil-phase and the aqueous phase if the antimicrobial exhibits substantial solubility in both phases. As yet another alternative, droplet chemistry can be adjusted to minimize such non-aqueous partitioning of the antimicrobial. For example, a dual phase system can be substituted for a droplets with skin system, or vice versa, or a surfactant (e.g., non-ionic non-fluorosurfactant, or a fluorosurfactant) with an increased or decreased HLB can be utilized.

Exemplary antimicrobials include but are not limited to β-lactam antimicrobials, cephamycin antimicrobials, cephalosporin antimicrobials, quinolone antimicrobials, fluoroquinolone antimicrobials, naphthyridine antimicrobials, polyketide antimicrobials, dihydrofolate reductase inhibitors, polymyxin antimicrobials, nitrofuran antimicrobials, antimicrobials of the amphenicol class, aminoglycoside antimicrobials, glycopeptide antimicrobials, polyene antifungal, imidazole or triazole antifungals such as imidazole- or triazole-class inhibitors of fungal lanosterol 14 α-demethylase, thiazole antifungals, allylamine antifungals, echinocandins antifungals, 5-fluorocytosine antifungals or combinations thereof. In some cases, the antimicrobial is cefoxitin, piperacillin, nalidixic acid, tetracyclin, vancomycin, trimethoprim, nitrofurantoin, colistin, nitrofuran, chloramphenicol, gentamycin, amphotericin B, fluconazole, or a combination thereof.

H. Droplet Antifungals

In some aspects, the oil phase of the water-in-oil emulsion droplets can contain one or more antifungal agents. The antifungal agent can be included to prevent microorganisms from growing outside the aqueous phase or to create a "fence" around the aqueous phase. For antifungal agents can be included in the oil phase to prevent the mold from growing outside of the aqueous phase. Exemplary antifungal agents include, but are not limited to, 2,6-dichloro-4-nitroaniline (or dicloran), 4,5,6,7-tetrachloro-2',4',5',7'-tetraiodofluorescein (or rose bengal), (RS)-1-[2-(allyloxy)-2-(2,4-dichlorophenyl)ethyl]-1H-imidazole (or imazalil, chloramizole), and/or chitosan.

In certain embodiments, the oil phase comprises dicloran at a concentration of about 5 mg/L to about 200 mg/L, about 10 mg/L to about 100 mg/L, about 20 mg/L to about 100 mg/L, about 40 mg/L to about 100 mg/L, or about 20 mg/L to about 200 mg/L. In some embodiments, the oil phase comprises dicloran at a concentration of about 5 mg/L, about 10 mg/L, about 20 mg/L, about 25 mg/L, about 30 mg/L, about 40 mg/L, about 50 mg/L, about 60 mg/L, about 70 mg/L, about 80 mg/L, about 90 mg/L, about 100 mg/L, about 125 mg/L, about 150 mg/L, about 175 mg/L, or about 200 mg/L.

In certain embodiments, the oil phase comprises rose bengal at a concentration of about 50 mg/L to about 375 mg/L, about 100 mg/L to about 200 mg/L or about 50 mg/L to about 150 mg/L. In some embodiments, the oil phase comprises rose bengal at a concentration of about 50 mg/L, about 75 mg/L, about 100 mg/L, about 125 mg/L, about 150 mg/L, about 175 mg/L, about 200 mg/L, about 250 mg/L, about 300 mg/L, about 350 mg/L, or about 375 mg/L.

In some embodiments, the oil phase comprises imazalil at a concentration from about 0.1 mg/L to about 2.5 g/L, about 0.1 mg/L to about 1.0 g/L, about 0.5 to about 1.0 g/L or about 0.5 mg/L to about 2.5 g/L. In some embodiments, the oil phase comprises imazalil at a concentration of about 0.1 mg/L, 0.25 mg/L, 0.5 mg/L, 0.75 mg/L, about 1 mg/L, about 2 mg/L, about 5 mg/L, about 10 mg/L, about 100 mg/L, about 1.0 g/L, or about 2.5 g/L.

In some embodiments, the oil phase comprises chitosan and the concentration of chitosan in the oil phase is about 0.3% or less.

I. Droplet Gelling Agents

In some aspects, the aqueous phase or the oil phase of the water-in-oil emulsion droplets comprises one or more gelling agents. In some embodiments in which the target microorganism is yeast, a gelling agent can be included in the aqueous phase to prevent a change in droplet size (e.g., to prevent a reduction in droplet size). In an embodiment, the aqueous phase comprises a hydrogel, such as alginic acid, that can be gelled by the addition of calcium ions. In a gelation process, alginate and calcium carbonate are included in the aqueous phase of the droplets and acetic acid is included in the oil phase of the droplets. During the gelation process, H+ ions from acetic acid diffuse from the oil phase into the aqueous phase of the droplet causing a decrease in the pH of the aqueous phase and the dissociation of calcium ions from the calcium carbonate according to the following equation:

$$CaCO_3+2H^+ \rightarrow CaHCO_3+H^+ \rightarrow Ca_2+H_2O+CO_2$$

In some embodiments, the concentration of alginate in the aqueous phase is about 3.5 grams/liter or less. In certain embodiments, the concentration of alginate in the aqueous phase is about 1, 2, 2.5, 3, or 3.5 grams/liter. In some embodiments, the concentration of calcium ion in the aqueous phase is about 1 gram/liter or less. In some embodiments, the concentration of calcium ion in the aqueous phase is about 0.25, 0.5, 0.75, or 1 gram/liter.

Other exemplary polymeric materials that may be used as gelling agents include, but are not limited to, kappa-carrageenan, iota-carrageenan, furcellaran, zein, succinylated zein, succinylated cellulose, and/or ethyl succinylated cellulose. Exemplary synthetic water soluble polymeric materials that may be used as gelling agents include, but are not limited to, those formed from vinyl pyrolidone, 2-methyl-5-vinyl pyrridine-metnyl acrylate-methacrylic acid copolymer, vinyl alcohol, vinyl pyridine, vinyl pyridine-styrene copolymer.

J. Droplet Detection Reagents

Water-in-oil emulsion droplets can contain one or more detection reagents. The detection reagents can be genotype specific nucleic acid detection reagents, proteins (e.g., antibodies, lectins, fibrinogen) and other molecules. Exemplary genotype specific nucleic acid detection reagents include, but are not limited to, nucleic acid probes. Genotype specific detection reagents may be specific for a particular genus, species or strain of microorganism. Exemplary nucleic acid probes include, but are not limited to, double-stranded probes, such as the double-stranded probes described in U.S. Pat. Nos. 5,928,862; or 9,194,007; Molecular Beacon probes, such as those described in WO 98/10096; TaqMan probes, such as those described in U.S. Pat. Nos. 5,210,015; 5,487,972; 5,538,848; 5,723,591; and 6,258,569; scorpion probes; light cycler probes; LUX probes; and amplifluor probes. Such probes can be used for detection by, e.g., incubating the droplets containing the probes under conditions for growth of the target microorganism(s), then lysing the target microorganisms after incubating, e.g., by heating, optionally amplifying a target locus, and detecting the presence or absence of a genotype with the nucleic acid probe. In some embodiments, labeled antibodies or other molecules specific to particular microorganisms are used. Such labeled molecules can be specific also to strains of microorganisms allowing for identification of those microorganisms which are susceptible to a particular antimicrobial agent.

The detection reagents can be genotype non-specific nucleic acid detection reagents include, but are not limited, to intercalating dyes. Intercalating dyes are generally aromatic cations with planar structures that insert between stacked base pairs in the DNA duplex, an arrangement that provides an environmentally dependent fluorescence enhancement for dye molecules and creates a large increase in the fluorescence signal relative to the free dye in solution. The signal enhancement provides a proportional response, allowing direct quantitative DNA measurements. Preferred intercalating dyes in the present disclosure include fluorescent dyes. The dye can be a cyanine or a non-cyanine intercalating dye. In some cases, the intercalating dye is a cyanine dye. In some cases the cyanine dye can be Thiazole Orange, SYBR® (e.g., Sybr Green I, Syber Green II, Sybr Gold, SYBR DX), Oil Green, CyQuant GR, SYTOX Green, SYT09, SYT010, SYT017, SYBR14, Oxazile Yellow, Thiazone Orange, SYTO, TOTO, YOYO, BOBO, and POPO. In some cases the dye is a non-cyanine dye. In some cases the non-cyanine dye is pentacene, anthracene, naphthalene, ferrocene, methyl viologen, tri-morpholmo ammonium, propidium (e.g., propidium iodide) or another aromatic or hetero aromatic derivative. In some cases, the intercalating dye is selected from the group consisting of DAPI (4',6-diamidino-2-phenylindole), acridine orange, ethidium monoazide (EMA), propidium monoazide (PMA), SYBR® Green I, SYBR® Gold, ethidium bromide, propidium bromide, Pico Green, Hoechst 33258, YO-PRO-I and YO-YO-I, SYTO®9, LC Green®, LC Green® Plus+, and EvaGreen®. In some cases, the intercalating dye is EvaGreen®. Such intercalating dyes can be used for detection by, e.g., incubating the droplets containing the probes under conditions for growth of the target microorganism(s), then lysing the target microorganisms after incubating, e.g., by heating, optionally amplifying a target locus, and detecting the presence or absence of double-stranded nucleic acid with the intercalating dye. In some embodiments, no incubation is required. Alternatively, the cells do not need to be lysed to detect the target microorganism and monitor the growth of the target microorganism.

The detection reagent can be phenotype specific. For example, the detection reagent can be a reagent that detects the presence of an enzyme activity indicative of the presence of an organism that produces such an enzyme. Accordingly, the detection reagent can be a pH sensitive chromophore or fluorophore that changes absorbance (e.g., of visible light) and/or fluorescence as a result of a change in pH. An example pH sensitive fluorescent probe is detectably fluorescent at a detection wavelength in an aqueous solution having a pH of less than about 5 and is not detectably fluorescent at the detection wavelength in an aqueous solution having a pH of greater than about 6.5.

For example, microorganisms such as certain bacteria such as Enterobacteriaceae, which are known to dramatically reduce the pH of media in which they are grown in the absence of a strong buffering agent at sufficient concentration can be detected with a marker (e.g., probe or other identifier) that changes color or fluoresces at low pH. Alternatively, the detection reagent can be a substrate of an enzyme indicative of a microorganism or class of microorganisms. In some embodiments, the detection reagent is a product of a reaction between a substrate and an enzyme produced by the target microorganism. The substrate can be colorimetric or fluorogenic. Exemplary enzymes, exemplary microorganisms, and corresponding substrates include, but are not limited to those described in Table I.

TABLE I

| Enzymatic activity | Genus/Species | Substrates |
|---|---|---|
| β-glucuronidase | *E. coli, Shigella* | Methyl-Umbellyferyl-β-D-glucuronide, Indolyl-β-D-glucuronide, Aldol ™-β-D-glucuronide |
| β-galactosidase | Coliforms | Methyl-Umbellyferyl-β-D-galactoside, Indolyl-β-D-galactoside, Aldol ™-β-D-galactoside |
| β-glucosidase | *Listeria* spp., KESC group, *Enterococcus* | Methyl-Umbellyfelyl-β-D-glucoside, Indolyl-β-D-glucoside, Aldol ™-β-D-glucoside |
| α-galactosidase | *Chronobacter* | Methyl-Umbellyfelyl-β-D-galactoside, Indolyl-β-D-galactoside, Aldol ™-β-D-galactoside |
| α-glucosidase | *Staphylococcus, Enterococcus* | Methyl-Umbellyfelyl-β-D-glucoside, Indolyl-β-D-glucoside, Aldol ™-β-D-glucoside |
| Phosphatase | *Staphylococcus aureus,* Enterobacteriaceae, *Clostridium perfringens* | Methyl-Umbellyferyl-phosphate, Indolyl-phosphate Aldol ™-phosphate |
| N-acetyl-glucosaminidase | *Candida* | Methyl-Umbellyferyl-N-acetyl-glucosaminide, Indolyl-N-acetyl-glucosaminide, Aldol ™-N-acetyl-glucosaminide, |
| Esterase | *Salmonella*, *Campylobacter, Pseudomonas* | Methyl-Umbellyferyl-caprylate, Indolyl-caprylate, Aldol ™-caprylate, Methyl-Umbellyferyl-caprate, Indolyl-caprate, Aldol ™-caprate, Methyl-Umbellyferyl-acetate, Indolyl-acetate, Aldol ™-acetate, |
| Aminopeptidase | *Pseudomonas* | Amino acid-p-nitroanilide, Amino acid-7 methyl coumarin |

TABLE I-continued

| Enzymatic activity | Genus/Species | Substrates |
| --- | --- | --- |
| Phospholipase | *Listeria monocytogenes, Pseudomonas aeruginosa, Bacillus cereus* | Methyl-Umbelliferyl-Phosphatidyl inositol, Indolyl-Phosphatidyl Inositol, Aldol ™-Phosphatidyl Inositol, Methyl-Umbelliferyl-Phosphatidyl choline, Indolyl-Phosphatidyl choline, Aldol ™-Phosphatidyl choline |

Generally, the detection reagents are selected to be compatible with the droplet chemistry employed. For example, detection reagents that reside essentially in the aqueous phase and do not substantially compartmentalize to the non-aqueous phase can be selected. In some cases, droplet chemistry can be adjusted to minimize non-aqueous partitioning of the detection reagent. For example, a dual phase system can be substituted for adroplets with skin system, or vice versa, or a surfactant (e.g., non-ionic non-fluorosurfactant, or a fluorosurfactant) with an increased or decreased HLB can be utilized.

J. Samples

Samples for partitioning into water-in-oil droplets can include any sample known or suspected of containing a target microorganism. For QI enumeration, the sample can be, or contain, food (e.g., food for humans or animals), environmental samples taken from surfaces or equipment. Samples can contain one or more target microorganisms. The target microorganism(s) can be or include bacteria, yeasts, or molds. Clinical samples include various bodily fluids or diluted specimens.

Any microorganism can be identified using the disclosed methods. Example target microorganism(s) can be or include gram positive and gram negative bacteria, Enterobacteriaceae (*Escherichia* spp., *Klebsiella* spp., *Enterobacter* spp., *Serratia marscescens*, and *Citrobacter* spp., *Shigella* spp., *Salmonella* spp., *Cronobacter* spp., . . . ), *Pseudomonas* spp., *Acinetobacter* spp., *Campylobacter* spp., *Staphylococcus* spp., *Legionella* spp., *Corynebacterium* spp., *Listeria* spp., *Enterococcus* spp., *Streptococcus* spp., *Clostridium* spp., *Bacillus* spp., *Candida* spp., *Aspergillus* spp., *Cryptococcus* spp., *Debaromyces* spp., *Geotrichum* spp., *Hanseniaspora* spp., *Kluyveromyces* spp., *Pichia* spp., *Rhodotula* spp., *Saccharomyces* spp., *Trichosporon* spp., *Zygosaccharomyces* spp., *Alternaria* spp., *Fusarium* spp., *Mucor* spp., *Penicillium* spp., *Pullularia* spp., *Trichothecium* spp. or a combination thereof.

The target microorganism(s) can be or include *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata, Mycobacterium tuberculosis, Cryptococcus albidus, Debaromyces hansenii, Geotrichum candidum, Hanseniaspora guillermonii, Kluyveromyces lactis, Pichia angusta, Rhodotula glutinis, Saccharomyces cerevisiae, Trichosporon pullulans, Zygosaccharomyces rouxii, Alternaria alternata, Fusarium graminearum, Mucor miehei, Penicillium patulum, Pullularia pullulans, Trichothecium roseum, Aspergillus niger*, or *Aspergillus fumigatus*, or a combination thereof.

i. Food Matrices

The food matrix can be a human food or an animal food, such as food for a pet or for livestock. The inventors have surprisingly found that water-in-oil droplet chemistries and methods of their use described herein are compatible with a wide variety of food matrices. Exemplary food matrices include, but are not limited to, those containing animal-based food (e.g., meat such as beef or ham; dairy such as milk or cheese) or plant-based food (e.g., vegetable or fruit), beverages or a combination thereof. In some cases, the meat containing food matrix is ground beef (e.g., 85% or 95% lean ground beef). In some cases, the milk containing food matrix is whole milk, cream, half-and-half, 2%, 1%, or fat-free (skim) milk.

A wide variety of fat contents of the food matrix are compatible with the water-in-oil chemistries described herein. Surprisingly, it was determined that substantial amounts of fat can be in the food matrix and not disturb the formation of the droplets. Possible fat contents include about 0%, less than about 0.5%, about 0.5%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, or about 60%. In some cases the fat content is from about 0% to about 20%, or from about 0% to about 25%, or from about 20 to 45%.

Generally the food matrix is suspended, mixed, blended, or homogenized into one or more, or all, components of the aqueous phase of the water-in-oil droplets. For example, the human food matrix can be mixed with one or more, or all, components of the aqueous phase of the water-in-oil droplets at a ratio of about 1:10, about 10:90, about 15:85, about 20:80, or about 25:75 weight of food matrix to total volume of aqueous phase components.

ii. Environmental Samples

When analyzing the environment, samples are from whichever environment is of interest whether indoors or outdoors. Examples of environments for which the QI is relevant include recreational water, beach sand and surfaces. An additional example is the environment on a farm, slaughterhouse or any other location where food is processed (e.g., packing houses). Samples from a farm would include soil samples, surfaces on farm buildings, farm equipment. Recreational water is any water in which recreation occurs and includes recreational bodies of water such as swimming pools, lakes, rivers, oceans, etc. Surfaces are relevant particularly in hospitals, schools, food processing facilities, etc. The samples would be swabs taken from surfaces and the swab is then introduced into the medium from which droplets are created.

iii. Clinical Samples

Described herein are methods and compositions for detecting the presence or absence or antimicrobial susceptibility of one or more target microorganisms in a clinical sample. In some cases, the sample is a sample from a subject (e.g., a human subject) known or suspected of being infected by a pathogenic microorganism. The sample can be blood, or a fraction thereof such as plasma or serum; tissue, urine, saliva; pericardial, pleural or spinal fluids; sputum, bone marrow stem cell concentrate, platelet concentrate; nasal, rectal, vaginal or inguinal swabs; wounds; specimens from skin, mouth, tongue, throat; ascites; stools and the like. Such samples can be analyzed to determine a microbial number and therefore assess the probability of pathogenic infection.

Alternatively, the clinical sample can be a pure or substantially pure culture of a target microorganism of known identity. Such a pure culture or substantially pure culture of a target microorganism of known identity can be analyzed by the disclosed methods for antimicrobial susceptibility. For example, a sample from a subject can be provided or obtained and assessed for the presence or absence of target microorganisms, e.g., by plating a sample from a subject or a cultured sample from a subject onto suitable medium. A single colony or plurality of colonies of target microorganism can be selected, optionally cultured, and partitioned into a plurality of water-in-oil emulsion droplets that contain a test antimicrobial. The test antimicrobial can be at one concentration or a plurality of concentrations in the plurality of water-in-oil emulsion droplets.

Sample Analysis

Samples can be analyzed with a fluorogenic or colorimetric substrate in the aqueous phase of the water-in-oil droplets to determine the presence or absence of a target microorganism that expresses an enzyme that recognizes the substrate, thus diagnosing a presence or absence of a genus or species or class of target microorganism(s). Alternatively, a binding partner specific for the microorganism of interest (e.g., an antibody) is used to determine the presence or absence of a target microorganism. In another embodiment, a target microorganism is identified as present if the interior of the droplet is turbid. Samples can be assayed in parallel with or without an antimicrobial susceptibility test, and optionally at multiple different antimicrobial concentrations, to simultaneously assess antimicrobial susceptibility of the target microorganism(s).

The total volume of aqueous phase components is a function of the number of droplets that the system generates and the volume of each droplet. In some cases, the total volume of aqueous phase components that is used to generate droplets is from 5 μL, 10 μL, 15 μL, 20 μL, 30 μL, 40 μL, 50 μL, 60 μL, 70 μL, 80 μL, 90 μL, 100 μL, 150 μL, 175 μL, 200 μL, 225 μL, 250 μL, 275 μL, 300 μL, 325 μL, 350 μL, 375 μL, 400 μL, 425 μL, 450 μL, 475 μL, 500 μL, 500 μL, 550 μL, 600 μL, 650 μL, 700 μL, 750 μL, 800 μL, 850 UL, 900 μL, 950 μL, 1 mL, 2 mL, 3 mL, 4 mL. In some cases, the total volume of aqueous phase components, including but not limited to clinical sample or pure culture from a clinical sample, that is used to generate droplets is from about 10 μL to about 1 mL, from about 20 μL to about 1 mL, from about 25 μL to about 500 μL, from about 50 μL to about 400 μL, from about 75 μL to about 300 μL, or from about 100 μL to about 200 μL.

In some cases, the total number of droplets of a plurality of droplets (e.g., containing a human food matrix or clinical sample) is at least about 1,000; 2,000; 3,000; 4,000; 5,000; 6,000; 7,000; 8,000; 9,000; 10,000; 15,000; 20,000; 25,000; 30,000; 35,000; 40,000; 50,000; 60,000; 70,000; 80,000; 90,000; 100,000. In other embodiments, up to a million droplets are formed. In some cases, the total number of droplets of a plurality of droplets (e.g., containing a human food matrix or clinical sample) is from about 1,000 to about 100,000; from about 2,000 to about 90,000; from about 3,000 to about 80,000; from about 4,000 to about 70,000; from about 5,000 to about 60,000; from about 7,500 to about 50,000; from about 10,000 to about 40,000; from about 15,000 to about 30,000, or about 20,000.

III. Methods

Described herein are methods for rapidly analyzing growth or number of one or more target microorganisms in a sample by partitioning the sample into a plurality of water-in-oil emulsion droplets, incubating the droplets for, or for at least, 1 to 50 (e.g., 5 to 20) doubling times, and detecting the presence or absence of the target microorganisms in the droplets.

Generally, the disclosed methods include encapsulating a sample in a plurality of water-in-oil emulsion droplets wherein the water-in-oil emulsion droplets further encapsulate a microbiological growth medium; incubating the plurality of water-in-oil emulsion droplets at a temperature permissive of microbiological growth, and for a period of time sufficient to allow the target microorganisms to go through 5 to 45 doubling times; identifying water-in-oil emulsion droplets comprising target microorganisms; and responsive to identifying the target microorganism in at least one water-in-oil emulsion droplet, determining that the target microorganism is present in the sample. In some embodiments, incubation is not used and the droplets are analyzed without incubating first.

In some embodiments, the water in oil droplets further include one or more of: intercalating dye, labeled protein (e.g., antibody, lectin or fibrinogen), bovine serum albumin.

A general method for analyzing a food matrix to determine the number of a target microorganism comprises the steps of: homogenizing a portion of the food matrix, wherein the portion of the matrix has a known mass or volume; incubating the plurality of water-in-oil emulsion droplets at a temperature permissive of microbiological growth, and for a period of time sufficient to allow the target microorganisms to double from 5 to 45 times; determining from the incubated water-in-oil emulsion droplets: a number of water-in-oil emulsion droplets that contain microorganisms, thereby determining a number of positive droplets; and a number of water-in-oil emulsion droplets that do not contain microorganisms, thereby determining a number of negative droplets; and determining from the number of positive droplets and negative droplets a total number of target microorganisms, thereby determining the number of target microorganisms per unit mass or volume of the food matrix. Example microbiological growth media include partially digested protein (e.g., partial tryptic digest of casein, partial papaic digest of soybean meal or a combination thereof). Water-in-oil droplets further optionally contain one or more of buffered peptone water (such as BAM Media M192) and a surfactant. For example, the surfactant can be non-ionic such as poloxamer. An example poloxamer has a molecular weight of about 1,800 g/mol. In some embodiments, the poloxamer comprises about 80% polyoxyethylene. Surfactants can be at concentrations of at least about 0.01% and no more than about 5% or about 1%. Encapsulated microbiological growth medium has a pH of about 7.2 in some embodiments.

A general method for assaying a target microorganism for a minimum inhibitory concentration of a test antimicrobial comprises: (i) encapsulating a plurality of the target microorganisms in a plurality of water-in-oil emulsion droplets comprising microbiological growth medium, wherein the water-in-oil emulsion droplets further encapsulate a microbiological growth medium; a first portion of the water-in-oil droplets encapsulate the test antimicrobial at a first concentration, or do not encapsulate the test antimicrobial; a second portion of the water-in-oil droplets encapsulate the test antimicrobial at a second concentration different than the first concentration; and optionally up to four additional portions of the water-in-oil droplets encapsulating additional different concentrations of the test antimicrobial; (ii) incubating the plurality of water-in-oil emulsion droplets at a temperature permissive of microbiological growth in an absence of the test antimicrobial, and for a period of time sufficient to allow the target microorganisms, if not inhibited by the test antimicrobial, to divide from 5 to 20 times, or more; iii) determining for each portion of the incubated water-in-oil emulsion droplets: a number of water-in-oil emulsion droplets comprising the target microorganism above a threshold number, thereby determining a number of positive droplets; and a number of water-in-oil emulsion droplets comprising the target microorganism below the threshold number, thereby determining a number of negative droplets; and iv) determining the minimum inhibitory concentration of the test antimicrobial from the positive and negative droplets for in each portion of droplets. In some embodiments, there are six portions of water-in-oil emulsion droplets and the first-fifth portions have concentrations of test antimicrobial that are serial two-fold dilutions of the concentration of the sixth portion.

In some embodiments, determining the number of positive droplets and the determining the number of negative droplets comprises detecting the presence or absence of bacterial spores or yeast or mold hyphae in the droplets by visual or computer imaging, wherein the number of positive droplets is the number of droplets exhibiting the presence of bacterial spores or yeast or mold hyphae in the plurality of water-in-oil droplets and the number of negative droplets is the number of droplets exhibiting the absence of bacterial spores or yeast or mold hyphae in the plurality of water-in-oil droplets.

A. Treatment of Aqueous Phase and/or Sample

The sample and/or the aqueous phase can be treated, prior to droplet generation, to facilitate formation of droplets. Treatment can be particularly suitable with a relatively high concentration and/or relatively long fungal filaments or microbial clusters in the aqueous phase. When droplets are formed under standard conditions, the aqueous phase can be subjected to a rapid decrease in cross sectional area, elongation, followed by separation and formation of the droplet. When microorganisms are present above certain concentrations or in certain morphologies (e.g., flocculent, hyphal, etc.), the ability to form droplets may be impaired. For example, these microorganisms can become entangled with each other in the rapid process of droplet formation, and may not have sufficient time to separate through diffusion, thereby forming a cord that causes the droplets not to form efficiently. The cord can result in jetting, microsatellites, and coalescence, and other features of poor emulsion formation. Alternatively, or in addition, the microorganisms can interact with the droplet interface, decreasing surface tension and preventing droplet formation.

In some cases, an approach is needed to overcome this effect on droplet formation. One exemplary approach is to slow down the rate of droplet formation so that the droplet has time to pinch off and form. Another mechanical solution may be to redesign the droplet generator to force the formation of droplets under these high concentration conditions. Another exemplary approach is to treat the sample to be incorporated into the aqueous phase to reduce clumping, aggregation, flocculation, length of hyphae, etc. In some cases, such reduction can be performed by heat treatment of the sample to at least about 40-50° C. for at least about 1, 2, 5, 10, 15, or 30 minutes, among others. The temperature applied is determined based on the heat stability of the microorganism being analyzed.

A further exemplary approach is to mechanically separate large clumps, aggregates, hyphal structures etc. Such mechanical separation can be performed as a separate step, or during homogenization or mixing of a sample (e.g., food matrix) with other components of the aqueous phase. For example, a sample of food matrix can be homogenized or mixed with aqueous phase components with a stomacher, bead beater, vortex, or other suitable apparatus, wherein such homogenization or mixing also separates clumps, aggregates, hyphal structures and the like of one or more target microorganisms. As another example, a sample, such as a pure culture of a target microorganism can be briefly subject to mechanical agitation (e.g., using a vortex mixer) prior to or after combining with one or more components of an aqueous phase.

B. Formation of Droplets

The aqueous and non-aqueous phases containing the components discussed above, including but not limited to target microorganisms, culture media, and optionally test antimicrobial, can be provided (e.g., obtained and/or prepared), and then utilized to form an emulsion, thus generating a plurality of water-in-oil droplets containing target microorganisms.

An emulsion generally includes droplets of a dispersed phase (e.g., an aqueous phase) disposed in an immiscible continuous phase (e.g., a non-aqueous phase such as an oil phase) that serves as a carrier fluid for the droplets. Both the dispersed and continuous phases generally are at least predominantly liquid.

Any suitable method and structure can be used to form the emulsion. Generally, energy input is needed to form the emulsion, such as shaking, stirring, sonicating, agitating, or otherwise homogenizing the emulsion. However, these approaches can produce polydisperse emulsions, in which droplets exhibit a range of sizes, by substantially uncontrolled generation of droplets. Alternatively, monodisperse emulsions (with a highly uniform size of droplets) can be created by controlled, serial droplet generation with at least one droplet generator. In exemplary embodiments, the droplet generator operates by microchannel flow focusing to generate an emulsion of monodisperse droplets. Other approaches to and structures for droplet generation that may be suitable are described, e.g., in U.S. Provisional Patent Application Ser. No. 61/341,218, filed Mar. 25, 2010; U.S. Provisional Patent Application Ser. No. 61/409,106, filed Nov. 1, 2010; U.S. Provisional Patent Application Ser. No. 61/409,473, filed Nov. 2, 2010; U.S. Provisional Patent Application Ser. No. 61/410,769, filed Nov. 5, 2010; U.S. patent application Ser. No. 12/862,542, filed Aug. 24, 2010; U.S. Patent Application Publication No. 2010/0, 173,394 A1, published Jul. 8, 2010; 2014/0,179,544; and International Patent Application Publication Nos. WO 2014/138,711; and WO 2011/109,546, the contents of each of which are hereby incorporated in the entirety for all purposes, and in particularly for disclosure related to droplet generation, droplet chemistry, microfluidic droplet handling, modulation of droplet temperature, and detection methods.

A surfactant present in the aqueous phase can aid in the formation of aqueous droplets within a non-aqueous phase. The surfactant can do so by physically interacting with both the non-aqueous phase and the aqueous phase, stabilizing the interface between the phases, and forming a self-assembled interfacial layer. The surfactant can increases the kinetic stability of the droplets, reduce coalescence of the droplets, reducing droplet aggregation, or a combination thereof. The droplets can be relatively stable to shear forces created by fluid flow during fluidic manipulation. For example, the droplets can be stable to flow rates of at least 40 L/min or 50 L/min in a 100 μm or 200 μm channel using selected combinations of non-aqueous and aqueous phase formulations. The resulting droplets can have any suitable shape and size. The droplets can be spherical, when shape is not constrained. The average diameter of the droplets can be about 1 to 500 μm, 5 to 500 μm, or 50 to 500 μm, and the average volume of the droplets may be about 50 pL to 500 nL, 100 pL to 10 nL, 200 pL to 5 nL, about 0.5 nL, about 1 nL, about 2 nL, about 3 nL, or about 5 nL. The number of droplets generated can depend upon a variety of factors including, but not limited to, the instrumentation utilized and manner of droplet generation (e.g., bulk agitation or serial generation), the droplet chemistry, droplet volume, the volume of aqueous and/or non-aqueous phases consumed during droplet generation, the volume of the sample analyzed, and the number of target microorganisms to be partitioned.

The droplets can be formed and then collected as an emulsion in a reservoir, such as vial, a test tube, a well of a plate, a chamber, or the like. In some embodiments, the droplets can be collected as an emulsion in a PCR tube or microplate, which is then incubated in an incubator configured to hold one or more PCR tubes or microplates. Alternatively, or in addition, the droplets can be collected in a reservoir and then transferred to a different container for incubation at a microbial growth temperature and/or may be manipulated and/or transported via fluidics, such as microfluidics to an incubator position. In an alternative embodiment, droplets are formed and enter a microfluidic channel. In such an embodiment, a single-file line of droplets forms in the channel.

There is no requirement for a specific concentration of microorganisms in the aqueous phase prior to droplet generation. In order to achieve substantially all droplets with no more than one microorganism at droplet generation, the starting aqueous phase is at a concentration where one in ten droplets contains a microorganism. In other embodiments, more than one microorganism can be in each droplet.

Droplets can be dispersed in a spacing fluid. In some cases, the spacing fluid can facilitate fluidic manipulation of droplets that are densely packed and/or facilitate dispersal of sticky droplets or capsules. For example, droplets can be generated, optionally transformed into capsules, incubated at one or more temperatures (e.g., microbial growth and/or detection temperatures), and then dispersed in a spacing fluid. Alternatively, the droplets can be dispersed in a spacing fluid prior to one or more of the incubations. In some cases, the spacing fluid contains the oil phase component of the non-aqueous phase used to generate the droplets. In some cases, the spacing fluid contains the oil phase but not the non-aqueous surfactant used to generate the droplets.

D. Droplet Transformation

Droplet chemistries containing one or more skin-forming components (e.g., skin-forming proteins) can be transformed from droplets to capsules for enhanced stability. Such transformation can be useful for analysis of slow growing microorganisms. In such cases, droplet coalescence or aggregation during extended incubation at a microbial growth temperature can be reduced or eliminated. Moreover, in some cases hyphal growth of a target microorganism can penetrate the walls of untransformed droplets, decreasing droplet stability. In such cases, transformation of droplets to capsules can be useful to reduce or eliminate such hyphal-penetration. Alternatively, capsule formation can be performed after incubation of droplets at a microbial growth temperature. Such capsule formation can, e.g., allow for capsule formation and simultaneous killing of target microorganisms. Such capsules can optionally be stored and/or analyzed at a later time. In some cases, capsule formation by heating after incubation of droplets at a microbial growth temperature can be performed to reveal internal epitope or to release nucleic acid from the microorganisms in the droplets, if present, and detect the nucleic acid with one or more probes or intercalating dyes.

Generally, droplets are transformed by heating. The droplets, the continuous phase, and/or the emulsion can be heated to a temperature sufficient for skin formation and for a time sufficient to produce the skin. An inverse relationship can exist between the temperature and the time sufficient for such a conversion to occur. That is, heating the droplets at a relatively low temperature can require a longer heating time than heating the droplets at a relatively higher temperature. However, skin formation can occur rapidly above a threshold temperature and much more slowly a few degrees below the threshold temperature. For example, skin formation can occur or be complete in less than about five minutes or less than about one minute when the emulsion is heated above the threshold temperature. Transformation of droplets into capsules may decrease the solubility of one or more skin-forming proteins (and/or other skin-forming component(s)) in the aqueous phase, such that the skin-forming component(s) become less soluble (e.g., become substantially insoluble) in the aqueous phase. Accordingly, the skin can be substantially insoluble in the aqueous phase.

In some embodiments, the threshold temperature can correspond to the denaturation temperature of a skin-forming protein in the aqueous phase. Accordingly, formation of the skin can be a consequence of protein denaturation that occurs much more rapidly above the threshold temperature than below. As an example, BSA has been reported to denature at about 50° C. to 55° C., and droplets incorporating BSA as a skin-forming protein can be induced to form a skin rapidly at about the same temperature. Accordingly, use of another skin-forming protein with a different denaturation temperature can require heating to a corresponding different temperature before skin is formed.

In some cases, a skin-forming component having a skin-forming (e.g., denaturation) temperature that is compatible with viability of a target microorganism can be selected. For example, a relatively low skin-forming temperature can be selected for capsule formation of droplets so that the target microorganism can remain substantially viable after incubating for, or for at least, about 1-5 minutes at the skin-forming temperature of the skin-forming component. Alternatively, a skin-forming component having a skin-forming (e.g., denaturation) temperature that is compatible with killing of target microorganisms or releasing nucleic acid from the target microorganisms can be selected. For example, a relatively high skin-forming temperature can be selected for capsule formation of droplets so that target microorganisms can be substantially killed or lysed after incubating for, or for at least about 1-30 minutes at the skin-forming temperature of the skin-forming component.

Heating the droplets to a temperature above skin formation temperature can convert a self-assembled interfacial layer to an interfacial skin. The skin can be composed of protein, or protein and surfactant, among others. In some cases, the droplets can be heated via thermal cycling, such as is performed during PCR amplification. The thermal cycling profile can include variations in temperature from about 4° C. to about 99° C. The droplets optionally can be heated via thermal cycling as a result of transport of the droplets through a flow-based thermocycling system. Further aspects of an exemplary flow-based thermocycling system are disclosed in U.S. Patent Application Publication No. 2010/0,173,394 A1, published Jul. 8, 2010, which is incorporated herein by reference.

D. Incubation

After droplet or capsule formation, the droplets or capsules can be incubated at a selected temperature or temperatures. For example, droplets or capsules can be incubated at one or more temperatures suitable for microbial growth, lysis, enzymatic processing of a colorimetric or fluorogenic substrate, or nucleic acid detection, or a combination thereof. Fluorogenic substrates undergo intramolecular aldol condensation after cleavage with an enzyme of the target microorganism, thereby producing a fluorescent indicator compound. Exemplary microbial growth temperature include, but are not limited to, 20° C., 25° C., 30° C., 35° C., 37° C., 40° C., 41° C., 41.5° C., 42° C., 43° C., 44° C., 45° C., or 50° C. In some cases, the microbial growth temperature is optimized for a particular target microorganism or class of target microorganisms. For example, if the target microorganism is *E. coli*, then the microbial growth temperature can be 37° C. Alternatively, a target microbial growth temperature that is suitable for growth of multiple microorganisms having multiple different optimal growth temperatures can be selected. For example, growth of yeasts, molds, and bacteria can be assayed simultaneously using a microbial growth temperature of 25° C., 30° C., 35° C., or 37° C.

Droplets or capsules can be incubated at a microbial growth temperature for a selected number of doubling times. The present inventors have surprisingly discovered that the methods and compositions described herein can provide accurate microbial numbers or antimicrobial susceptibility results after no time for doubling or a relatively small number of doubling times (e.g., 1, 2, 3, 4, 5, 10, 15, 20, 25, 30, 35, 40, or 45; 5-45, 10-40, 15-30, 20-25, 10-20, 10-15, or 5-15), thus enabling a rapid assay as compared to standard culture in liquid (broth) and/or plating techniques. One of skill in the art will appreciate that a target microorganism that is incubated for a selected number of doubling times at a microbial growth temperature does not necessarily double in quantity the selected number of times due to lag phase, acceleration phase, exponential phase, stationary phase, deceleration phase, death phase, or combinations thereof that microorganisms typically exhibit.

Such selected numbers of doubling times can correspond to at least about 15 min, 20 min, 30 min, . . . 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 32 h, 34 h, 36 h, 38 h, 40 h, 44 h, 48 h, 52 h, 58 h, 60 h, 66 h, or 72 h.

The selected numbers of doubling times can correspond to:

from at least about 4 h and no more than about 16 h or at least about 4 h and no more than about 8 h for bacteria;

from at least about 6 h and no more than about 12 h or at least about 8 h and no more than about 12 h for yeast;

from at least about 8 h and no more than about 36 h or at least about 8 h and no more than about 24 h for molds;

from about from 2 h to about 8 h, 2 h to about 6 h, from about 4 h to about 8 h, or from about 4 h to about 12 h for a fast growing microorganism such as *E. coli* at or near an optimal growth temperature such as 37° C.;

from about 4 h to about 12 h, from about 4 h to about 16 h, from about 4 h to about 18 h, from about 4 h to about 24 h, from about 4 h to about 48 h, from about 6 h to about 12 h, from about 6 h to about 16 h, from about 6 h to about 18 h, from about 6 h to about 24 h, from about 6 h to about 48 h, from about 8 h to about 16 h, from about 8 h to about 18 h, from about 8 h to about 24 h, or from about 8 h to about 48 h for a slower growing microorganism such as *Listeria* spp. at or near an optimal growth temperature such as 37° C.;

from about 4 h to about 12 h, from about 6 h to about 12 h, from about 6 h to about 16 h, from about 6 h to about 18 h, from about 6 h to about 24 h, from about 6 h to about 48 h, from about 8 h to about 12 h, from about 8 h to about 16 h, from about 8 h to about 18 h, from about 8 h to about 24 h, from about 8 h to about 48 h, from about 12 h to about 16 h, from about 12 h to about 18 h, from about 12 h to about 24 h, or from about 12 h to about 48 h for a yeast or mold.

In some cases, after incubation at the microbial growth temperature, droplets or capsules are incubated at a second temperature. The second temperature can be lower (e.g., 4° C.) for short term storage. The second temperature can be higher (e.g., 65° C. or 95° C.) to form capsules, lyse target microorganisms, release nucleic acid, and/or initiate amplification and/or detection by thermocycling. In some cases, after incubation at the microbial growth temperature, droplets or capsules are incubated at a temperature selected for fluorogenic or colorimetric detection of an enzyme that is not substantially active against a fluorogenic or colorimetric substrate at the microbial growth temperature. Alternatively, the enzyme can be active at the microbial growth temperature and additional incubation temperatures are not required. In some cases, although the enzyme can be active at the microbial growth temperature it is sequestered inside the cells of the target microorganism. In such cases, a high temperature incubation step after microbial growth can be performed to release a fraction of the enzyme for subsequent detection.

E. Detection

The presence or absence of target microorganisms in a plurality of droplets or capsules can be detected by a variety of methods. For example, the inventors have surprisingly discovered that droplets containing above a threshold concentration of certain target microorganisms (e.g., after incubation of droplets for a suitable number of target microorganism doubling times or divisions) exhibit a detectable autofluorescence. Therefore, after incubation at a microbial growth temperature droplets can be assayed for the presence or absence of autofluorescence, wherein the autofluorescence is indicative of the presence of the target microorganism.

In some cases, detection can be detection of turbidity in the droplets. Thus, droplets in which encapsulated microorganisms have substantially divided can be detected. In some cases, detection can be detection of fluorescence or absorbance of a fluorophore or chromophore. For example, a digestion of a fluorogenic or colorimetric substrate such as one of the substrates of Table I can be detected by detecting droplets that exhibit characteristic absorbance or fluorescence. As another example, fluorogenic probes or intercalating dyes can be used to respectively detect the presence or absence of a nucleic acid sequence or double-stranded nucleic acid in general. As yet another example, a pH sensitive chromophore or fluorophore can be used to detect presence or absence of a change in pH in the droplets indicating a presence or absence of target microorganisms in the droplets respectively. In other embodiments, a detectable moiety that specifically binds the microorganism of interest is used to identify the presence or absence of the microorganism. Such a detectable moiety can be a labeled protein (e.g., an antibody, a lectin, fibrinogen). Markers such as these can be used with and without lysing agents.

Generally, droplets are identified as positive or negative. Positive droplets are those that contain microorganisms or contain above a threshold number of microorganisms and negative droplets are those that do not contain microorganisms or contain below a threshold number of microorganisms. In some assays, droplets are analyzed before and after incubation. In such an assay, positive droplets are those for which the number of microorganisms increased from the initial analysis and negative droplets are those for which the number of microorganisms did not increase from the initial analysis. Analysis can be performed manually, e.g., using an optical microscope or in an automated fashion. In some cases, the automated detection is performed by serially flowing the droplets through a detection region configured to detect absorbance, transmission or emission (e.g., fluorescence) at one or more wavelengths. In some cases, a spacing fluid is added to droplets flowing in a channel to a detection region that is operatively disposed with respect to a detector and/or an excitation light source. In some cases, the automated detection is performed by a high throughput 3D particle counting system in a volume of droplets as described in *Nature Communications* 5, Article number: 5427, doi: 10.1038/ncomms6427, 13 Nov. 2014. For example, high throughput 3D particle counting can be used to detect a single-fluorescent droplet in a several milliliter pool of non-fluorescent droplets.

The sample can be assayed for total microbial load, total bacterial load, total coliforms, yeasts, molds, or a combination thereof. Alternatively, specific microorganisms are identified and, optionally, quantified.

F. Determination of Microorganism Number

After droplets are detected for the presence or absence of microorganisms, thus obtaining a number of positive droplets and a number of negative droplets, the data can be analyzed to determine a quantitative result, such as microbial load of a food matrix sample or the presence of a target microorganism in a clinical sample. In some cases, the fraction of positive droplets (i.e., ratio of positive droplets over total droplets) is calculated from the number of positive and negative droplets. In some cases, the fraction is corrected by fitting the fraction to a Poisson distribution. The Poisson correction accounts assumes that target microorganisms are randomly partitioned into droplets during droplet formation, and therefore multiple target microorganisms can partition into a single droplet with a finite, concentration dependent, and predictable probability. In some cases, the value of $\ln(1-p)$, where p is the fraction of positive droplets, determines the number of target microorganisms per droplet and thus the number of target microorganisms in the sample from which the droplets were generated.

IV. Kits

Described herein are kits for enumeration of one or more target microorganisms, determining antimicrobial susceptibility of a target microorganism, or a combination thereof. The kits can include non-aqueous phase reagents for forming dual-phase droplets and/or droplets with skins, such as oil (e.g., fluorous oil) and non-aqueous surfactant (e.g., a fluorosurfactant or mixture containing one or more fluorosurfactants). The kit can include aqueous phase reagents, such as skin-forming components (e.g., BSA). Additional or alternative aqueous phase reagents include aqueous surfactant (e.g., a non-ionic non-fluorosurfactant or a mixture containing a non-ionic non-fluorosurfactant). The kit can include oil phase reagents such as antifungal agents (e.g., dicloran, rose bengal, and/or chitosan). The kit can include detection reagents including, but not limited to, one or more enzyme substrates of Table I, an intercalating dye, an antibody, a lectin, fibrinogen, or a nucleic acid probe. The kit can include one or more control microorganisms. The kit can include one or more test antimicrobials. The kit can include instructions for carrying out the methods described herein.

EXAMPLES

Example I: Detection of Antimicrobial Susceptibility

Materials and Methods

Strains with well characterized minimal inhibitory concentrations (MICs) against a large variety of drugs (CLSI: M100S21. Performance standards for antimicrobial susceptibility testing; twenty-first informational supplement. Wayne, PA: Clinical and Laboratory Standards Institute; 2011) were chosen from isolates obtained from the American Type Culture Collection (ATCC®). They comprised *Escherichia coli* (ATCC®25922™), *Staphylococcus aureus* (ATCC®29212™), *Enterococcus faecalis* (ATCC®29212™) and *Candida albicans* (ATCC®24433™). Another strain of *S. aureus* ATCC®43300 was studied for which the MIC was not characterized in the CLSI document but determined by Witte et al. (Clin Microbiol Infect 2007; 13:408-412). This strain is known to carry an heterogeneous resistance phenotype was also used with or without induction with cephalosporins.

Each strain was stored as −80° C. frozen stock. Except when indicated, after overnight cultures in Trypto-casein-soy broth (TCS; Bio-Rad, Marnes la Coquette, France), all bacterial strains were started from the same adjusted turbidity which was equivalent to 1:100 of a 0.5 McFarland in TCS. For the *Candida albicans*, the starting turbidity was equivalent to a 1:10 of a 0.1 McFarland.

Susceptibility Testing

Droplets were prepared according to the manufacturer instructions (Bio-Rad) using QX200™ Droplet Generation Oil for EvaGreen (+surfactant) with the mixing parameters adjusted for sample volume and approximate number of microorganisms. Turbidity adjusted cultures were diluted in aqueous-phase reagents with a known concentration of antibiotic or antifungal agents in a 1:1 ratio of TCS culture to aqueous phase reagents (v/v, 10 μL/10 μL).

The antibiotic and antifungal agents tested comprised cefoxitin, piperacillin, nalidixic acid, tetracyclin, vancomycin, trimethoprim, nitrofurantoin, colistin, nitrofuran, chloramphenicol, gentamycin, amphotericin B, fluconazole.

As soon as the droplets were prepared, the cartridges, protected by an adhesive film, were directly incubated at 37° C. (at 30° C. for the *C. albicans*).

After 4 and 6 hours of incubation, droplets were pipetted and introduced into cell counting slides (Bio-Rad). The microorganisms were then observed in the droplets using a microscope (objective 100× or 400×). The approximate counts of droplets carrying microorganisms as their growth inside the droplets were reported.

The minimal inhibitory concentration (MIC) was determined as the lowest concentration of an antimicrobial agent that prevents visible growth of a microorganism (i.e. a total absence of bacteria or a total absence of fungal growth observable in droplets using the microscope).

Results

I. *E. coli* ATCC®25922

1-Piperacillin: Expected MIC (CLSI): 1-4 mg/L

| Reading times/ Conc of antibiotic | 4 h |
|---|---|
| No antibiotic | Growth in more than 50% of the droplets |
| 1 mg/L | Limited growth in droplets with cells forming filaments |
| 2 mg/L | No growth |

Observed MIC: 2 mg/L

2-Nalidixic acid: Expected MIC (CLSI): 1-4 mg/L

| Reading times/ Conc of antibiotic | 4 h | 6 h |
|---|---|---|
| No antibiotic | Growth in more than 50% of the droplets | Growth in more than 50% of the droplets |
| 1 mg/L | Growth in 20-30% of droplets with cells forming filaments | Growth in about 50% of droplets with cells forming filaments |
| 2 mg/L | Growth in 20-30% of droplets with cells forming filaments | One or few small filaments in 10-25% of droplets |
| 4 mg/L | One or few small filaments in 20-30% of droplets | No growth |

Observed MIC: 4 mg/L

3-Tetracycline: Expected MIC (CLSI): 0.5-2 mg/L

| Reading times/Conc of antibiotic | 4 h | 6 h |
|---|---|---|
| No antibiotic | Growth in more than 50% of the droplets | Growth in more than 50% of the droplets |
| 0.125 mg/L | Growth in 30-50% of droplets | Growth in 30-50% of droplets |
| 0.25 mg/L | Limited growth in few droplets | Growth in 20-30% of droplets |
| 0.5 mg/L | No growth | No growth |

Observed MIC: 0.5 mg/L

4-Trimethoprim: Expected MIC (CLSI): 0.5-2 mg/L

| Conc of | Reading times | |
|---|---|---|
| antibiotic | 4 h | 6 h |
| No antibiotic | Growth in more than 50% of the droplets | Growth in more than 50% of the droplets |
| 0.125 mg/L | Limited growth in few droplets with cells forming filaments | Growth in 30-50% of droplets with cells forming filaments |
| 0.25 mg/L | Limited growth in few droplets with cells forming filaments | Growth in 20-30% of droplets with cells forming filaments |
| 0.5 mg/L | One or few small filaments in about 20% of droplets | Limited growth in few droplets with cells forming filaments |

-continued

| Conc of | Reading times | |
|---|---|---|
| antibiotic | 4 h | 6 h |
| 1 mg/L | No growth | Limited growth in few droplets with cells forming filaments |
| 2 mg/L | No growth | No growth (one small filament in 10-25% of droplets likely artifact) |

Observed MIC: 1 mg/L (4 h) or 2 mg/L (6 h)

5-Colistin: Expected MIC (CLSI): 0.5-2 mg/L

| Cone of | Reading times | |
|---|---|---|
| antibiotic | 4 h | 6 h |
| No antibiotic | Growth in 30-50% of the droplets | Growth in more than 50% of the droplets |
| 0.125 mg/L | Growth in 10-20% of droplets | ND |

-continued

| Cone of | Reading times | |
|---|---|---|
| antibiotic | 4 h | 6 h |
| 0.25 mg/L | Limited growth in few droplets | Growth in 20-30% of droplets |
| 0.5 mg/L | Growth in 1 droplet | Growth in about 10% of droplets |
| 1 mg/L | ND | No growth |

Observed MIC: 1 mg/L

6-Nitrofuran: Expected MIC (CLSI): 4-16 mg/L

| Conc of | Reading times | |
|---|---|---|
| antibiotic | 4 h | 6 h |
| No antibiotic | Growth in >50% of the droplets | Growth in more than 50% of the droplets |
| 1 mg/L | Growth in approx. 20% of droplets | ND |
| 2 mg/L | Limited growth in about 20% of droplets with cells; some of them forming filaments | Growth in approx. 30-50% of droplets |
| 4 mg/L | Limited growth in about 20% of droplets with cells forming filaments | Growth in approx. 20% of droplets with cells; some of them forming filaments |
| 8 mg/L | No growth | No growth |
| 16 mg/L | No growth | No growth |

Observed MIC: 8 mg/L

7-Chloramphenicol: Expected MIC (CLSI): 2-8 mg/L

| Conc of | Reading times | |
|---|---|---|
| antibiotic | 4 h | 6 h |
| No antibiotic | Growth in >50% of the droplets | Growth in more than 50% of the droplets |
| 0.5 mg/L | Growth in approx. 30-50% of droplets | ND |
| 1 mg/L | Growth in approx. 20-30% of droplets | Growth in approx. 30-50% of droplets |
| 2 mg/L | No growth | Limited growth in few droplets with cells |
| 4 mg/L | No growth | No growth |
| 8 mg/L | No growth | ND |

Observed MIC: 2-4 mg/L

8-Gentamycin: Expected MIC (CLSI): 0.25-1 mg/L

| Conc of | Reading times | |
|---|---|---|
| antibiotic | 4 h | 6 h |
| No antibiotic | Growth in approx. 50% of the droplets | Growth in more than 50% of the droplets |
| 0.125 mg/L | Growth in approx. 50% of the droplets | ND |
| 0.25 mg/L | Growth in approx. 30-50% of droplets | ND |
| 0.5 mg/L | Growth in approx. 30% of droplets | Growth in approx. 30-50% of droplets |
| 1 mg/L | Few droplets with limited # of cells | Few droplets with limited # of cells |
| 2 mg/L | No growth | No growth |

Observed MIC: 2 mg/L

II. *S. aureus* ATCC®29213™

1-Vancomycin: Expected MIC (CLSI): 0.25-1 mg/L

| Conc of | Reading times | |
|---|---|---|
| antibiotic | 4 h | 6 h |
| No antibiotic | Growth in approx. 50% of the droplets | Growth in more than 50% of the droplets |
| 0.25 mg/L | Growth in approx. 25-50% of droplets | Growth in approx. 50% of the droplets |

-continued

| Conc of | Reading times | |
|---|---|---|
| antibiotic | 4 h | 6 h |
| 0.5 mg/L | 1 droplet with cells | Growth in approx. 10% of droplets |
| 1 mg/L | ND | No growth |

Observed MIC: 1 mg/L

2-Cefoxitin: Expected MIC (CLSI): 1-4 mg/L

| Conc of | Reading times | |
|---|---|---|
| antibiotic | 4 h | 6 h |
| No antibiotic | Growth in approx. 50% of the droplets | ND |
| 0.5 mg/L | Growth in approx. 20-30% of droplets | ND |
| 1 mg/L | Growth in approx. 20% of droplets | Growth in <50% of droplets |
| 2 mg/L | No growth | No growth |

Observed MIC: 2 mg/L

III. *E. faecalis* ATCC®29212™

1-Vancomycin: Expected MIC (CLSI): 1-4 mg/L

| Conc of | Reading times | |
|---|---|---|
| antibiotic | 4 h | 6 h |
| No antibiotic | Growth in >50% of the droplets | Growth in more than 50% of the droplets |
| 0.25 mg/L | Growth in 25-50% of droplets | Growth in 20-50% of droplets |
| 0.5 mg/L | Growth in 25-30% of droplets | Growth in approx. 30% of droplets |
| 1 mg/L | Limited growth in 25-30% of droplets | Growth in 20-30% of droplets |
| 2 mg/L | No growth | No growth |

Observed MIC: 1-2 mg/L

IV. *C. albicans* ATCC®24433™

1-Amphotericin B: Expected MIC (CLSI): 0.25-1 mg/L

| Conc of | Reading times | | |
|---|---|---|---|
| antibiotic | 4 h | 6 h | 24 h |
| No antibiotic | Growth in 15-20% of droplets | Full growth in approx. 50% of the droplets | Full growth in approx. 50% of the droplets |
| 0.125 mg/L | Growth in 15-20% of droplets | Full growth in approx. 50% of the droplets | Full growth in approx. 50% of the droplets |
| 0.25 mg/L | Growth in 15-20% of droplets | Growth in 30-40% of the droplets | Full growth in approx. 50% of the droplets |
| 0.5 mg/L | Growth in 15-20% of droplets | Growth in approx. 30% of droplets | Growth in approx. 20% of droplets |
| 1 mg/L | Limited growth in 15-20% of droplets | Limited growth (2-3 cells) in approx. 20% droplets with cells | Limited growth in approx. 20% of droplets |
| 2 mg/L | 1 cell in 15-20% of droplets | Limited growth (2-3 cells) in approx. 20% droplets with cells | Limited growth in approx. 20% of droplets |

-continued

| Conc of antibiotic | Reading times | | |
|---|---|---|---|
| | 4 h | 6 h | 24 h |
| 4 mg/L | 1 cell in 15-20% of droplets | 1 cell in 10% of droplets | 1-2 cells in 20% of droplets |
| 8 mg/L | 1 cell in 15-20% of droplets | 1 cell in 10% of droplets | 1-2 cells in 20% of droplets |

Observed MIC: 2-4 mg/L

2-Fluconazole: Expected MIC (CLSI): 0.25-1 mg/L

| Conc of antibiotic | Reading times | |
|---|---|---|
| | 4 h | 6 h |
| No antibiotic | Growth in 35-40% of droplets | Growth in 35-40% of droplets |
| 1 mg/L | Growth in 25% of droplets | Growth in 15-20% of droplets |
| 2 mg/L | Growth in 15-20% of droplets | Growth in 15-20% of droplets |
| 4 mg/L | Growth in approx. 15% of droplets | Growth in 15-20% of droplets |
| 8 mg/L | Limited growth (1-4 cells) in approx. 15% of droplets | Limited growth (few cells) in approx. 15% of droplets |
| 16 m g/L | Limited growth (1-4 cells) in approx. 15% of droplets | Limited growth (few cells) in approx. 15% of droplets |
| 32 m g/L | Limited growth (1-4 cells) in approx. 15% of droplets | Limited growth (few cells) in approx. 15% of droplets |
| 64 m g/L | Limited growth (1-4 cells) in approx. 15% of droplets | Limited growth (even less cells) in approx. 15% of droplets |

Observed MIC: 8 mg/L

V. *S. aureus* ATCC®43300™: Expected MIC (JCM): 16-32 mg/L

The induction of the resistance was performed by inoculating this strain on MRSASELECTII (Bio-Rad) followed by an overnight incubation. Colonies were picked up to perform the bacterial suspension in TCS.

| | Reading times | |
|---|---|---|
| Conc of antibiotic | 4 h w/o induction | 6 h w/o induction |
| No antibiotic | Growth in approx. 20% of droplets | Growth in approx. 20% of droplets |
| 4 mg/L | No growth | Limited growth (few cells) in few of droplets |
| 8 mg/L | ND | No growth |
| 16 mg/L | ND | ND |
| 32 mg/L | ND | ND |

Observed MIC: 2-4 mg/L using non induced strain

-continued

| | Reading times | |
|---|---|---|
| Conc of antibiotic | 4 h with induction | 6 h with induction |
| No antibiotic | Growth in approx. 20% of droplets | Growth in 50% of droplets |
| 4 mg/L | Limited growth (few cells) in approx. 10% of droplets | Limited growth (few cells) in less than 10% of droplets |
| 8 mg/L | Limited growth in few droplets | 1 droplet with cells |
| 16 mg/L | Very limited growth (few cells) in few droplets | No growth |
| 32 mg/L | No growth | ND |

Observed MIC: 16-32 mg/L with induced strain

As illustrated in the foregoing results, MICs against a variety of test antimicrobials can be accurately and rapidly determined for a variety of target microorganisms using water-in-oil droplet compositions and methods described herein.

Example II: Enumeration of Microorganisms

1. Encapsulation and Growth

Goal: To investigate whether i) bacterial cells can be encapsulated in droplets using water-in-oil droplet chemistry, ii) bacterial cells can grow inside droplets and iii) bacterial cells can metabolize a substrate in droplets in order to generate a fluorescent signal. For this purpose a pure culture of *Escherichia coli* cells was encapsulated in droplet in the presence of 4-Methylumbelliferyl-β-D-glucuronide and incubated at 37° C. for various times. Droplets were then observed with either visible or fluorescent microscopy.

Materials and Methods

*E. coli* ATCC 25922 was grown overnight in Tryptone-Soya Broth.

The culture was diluted in order to obtain:

- Droplets culture: A $10^5$ cfu/ml bacterial suspension in Buffered Peptone Water supplemented with 4-Methylumbelliferyl-β-D-glucuronide (100 mg/l) and Pluronic F-98 (1%). 20 μl of this suspension were mixed with 50 μl of QX200™ Droplet Generation Oil for EvaGreen (+surfactant) (Available from Bio-Rad Laboratories) with the Bio-Rad droplets generator system. The droplets then were transferred into a 96-well microplate.
- Bulk reaction: A 50 cfu/ml bacterial suspension in 5 ml of Buffered Peptone Water supplemented with 4-Methylumbelliferyl-β-D-glucuronide (100 mg/l) and Pluronic F-98 (1%).

Both microplates and tubes were incubated at 37±1° C. for 24 hours.

After 0, 4, 6, 8 and 24 hours of incubation:

- A sample of droplets was observed with the ZOE Fluorescent Cell Imager (Bio-Rad) in the visible channel and the blue fluorescence channel.
- A sample of droplets was tested with the Bio-Rad droplet reader QX200.
- In the same time, the 5 ml tube was observed under ultraviolet light using a Wood lamp at 365 nm.

Results: As shown on FIG. 1, bacterial growth can be detected from 6 h following encapsulation. Growth could be followed either by direct observation of droplets full of bacteria or owing to the emission of a blue fluorescence. Control experiments without MUG substrate (not shown) as well as experiments with other bacteria (see 4) demonstrated that this blue fluorescence was due to the auto-fluorescence of the droplet loaded with bacteria. The substrate was likely leached into the oil phase. Conversely, metabolization of the substrate was observed in the bulk reaction (not shown).

This lack of metabolization was confirmed with *Listeria*. Yet, this experiment indicated that it is possible to encapsulate and grow bacteria within droplets in a short time. The autofluorescence in droplets phenomenon has not been previously described.

2. Food Matrices

Goal: To investigate whether the generation of droplets is compatible with a suspension obtained from a food matrix diluted 10-fold in buffered peptone water. Several matrices were used for a proof-of-concept experiment.

Materials and Methods 25 g of a food matrix (ground beef with 5% and 15% of fat content, ham, raw milk, raw milk camembert and grated carrots) were weighed in a stomacher bag containing a 280 μm filter.

225 ml of Buffered Peptone Water supplemented with 4-Methylumbelliferyl-β-D-glucuronide (100 mg/l) and Pluronic F-98 (1%) were added to the bag.

The food sample was suspended in the broth using a stomacher system for 2 minutes.

20 μl of the food suspension were mixed with 50 μl of QX200™ Droplet Generation Oil for EvaGreen (+surfactant) with the Bio-Rad droplets generator system.

The food suspensions and the droplets obtained were observed with the ZOE Fluorescent Cell Imager in the visible channel.

Results: Visual inspection of droplets (visible microscopy) showed that droplets were actually generated whatever the food matrix. All droplets were homogeneous in size and their stabilities over time were comparable. This result indicated that the standard protocol for sample preparation from food matrices is compatible with droplet generation within the limits of the matrices tested so far (FIG. 2).

3. Time-to-Result

Goal: To determine whether growth of bacteria encapsulated from a food suspension can be detected at an earlier time than when the same suspension is streaked on a petri dish. For this purpose, a ham matrix was contaminated with *E. coli*, and a sample of the homogenized matrix was either encapsulated or streaked on a Petri dish before incubation at 37° C. for various times.

Materials and Methods 25 g of ham were suspended in 225 ml of Buffered Peptone Water and Pluronic F-98 (1%) in a stomacher bag with a 280 μm filter using the stomacher system for 2 minutes.

An overnight culture of *E. coli* ATCC 25922 in Tryptone-Soya Broth was diluted in order to spike the ham suspension at the level of $10^5$ cfu/mL.

20 μl of this suspension was mixed with 50 μl of QX200™ Droplet Generation Oil for EvaGreen (+surfactant) with the Bio-Rad droplets generator system. The droplets were transferred into an Eppendorf microplate.

Serial dilutions of the ham suspension were carried out and spread on a TBX agar.

The Eppendorf microplate and the TBX plates were incubated at 37±1° C. for 24 hours.

After 0, 4, 6, 8 and 24 hours of incubation:

A sample of droplets was observed with the ZOE Fluorescent Cell Imager (Bio-Rad) in the visible channel and the blue fluorescence channel.

A sample of droplets was tested with the Bio-Rad droplets reader QX200.

In the same time, the TBX agar plates were observed.

Results: Growth of the bacteria encapsulated in droplets was readily detectable either by visible microscopy or by fluorescent microscopy owing to the autofluorescence phenomenon described above. Bacteria were detected as early as 6 h following encapsulation whereas the colonies were not detected before 24 h on the Petri dish. Direct visual enumeration the positive droplets or reading the positive droplets with the QX reader yielded an estimate close to the expected number of bacteria and matching the visual enumeration on Petri dish. Altogether these results demonstrated that droplet encapsulation can be used to enumerate bacteria present in a suspension of a food sample (FIG. 3).

4. Other Bacteria, Yeasts, and Molds

Goal: To prove that the principle of early detection of bacterial growth in droplet can be extended to other bacteria and microorganisms.

Materials and Methods (Bacteria and Yeast)

*Enterobacter cloacae* ATCC 13047, *Enterobacter aerogenes* ATCC 13048, *Citrobacter freundii* ATCC 8090, *Bacillus subtilis* ATCC 6633, *Staphylococcus aureus* ATCC 25923 and *Candida albicans* ATCC 10231 were grown overnight in Tryptone-Soya Broth.

The cultures were then diluted in order to obtain a $10^5$ cfu/ml cells suspension in Buffered Peptone Water supplemented with Pluronic F-98 (1%). 20 μl of these suspensions were mixed with 50 μl of QX200™ Droplet Generation Oil for Eva Green (+surfactant) with the Bio-Rad droplets generator system. The droplets obtained were transferred in a well of an Eppendorf microplate.

The microplate was incubated at 37±1° C. for 24 hours.

After 0, 4, 6, 8 and 24 hours of incubation:

A sample of droplets was observed with the ZOE Fluorescent Cell Imager in both the visible channel and the blue fluorescence channel.

A sample of droplets was enumerated with the Bio-Rad droplets reader QX200.

Figure 6A:
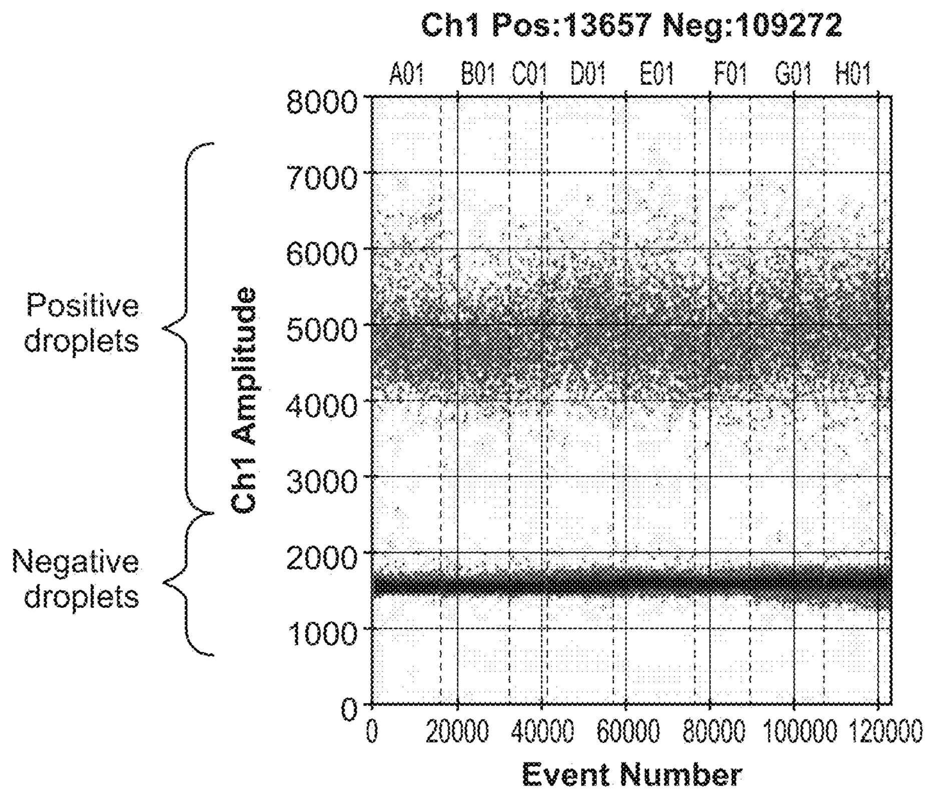
FIGS. 6A-6B illustrate accurate enumeration of target bacteria by counting positive and negative droplets in an automated droplet reader.
Figure 6B:
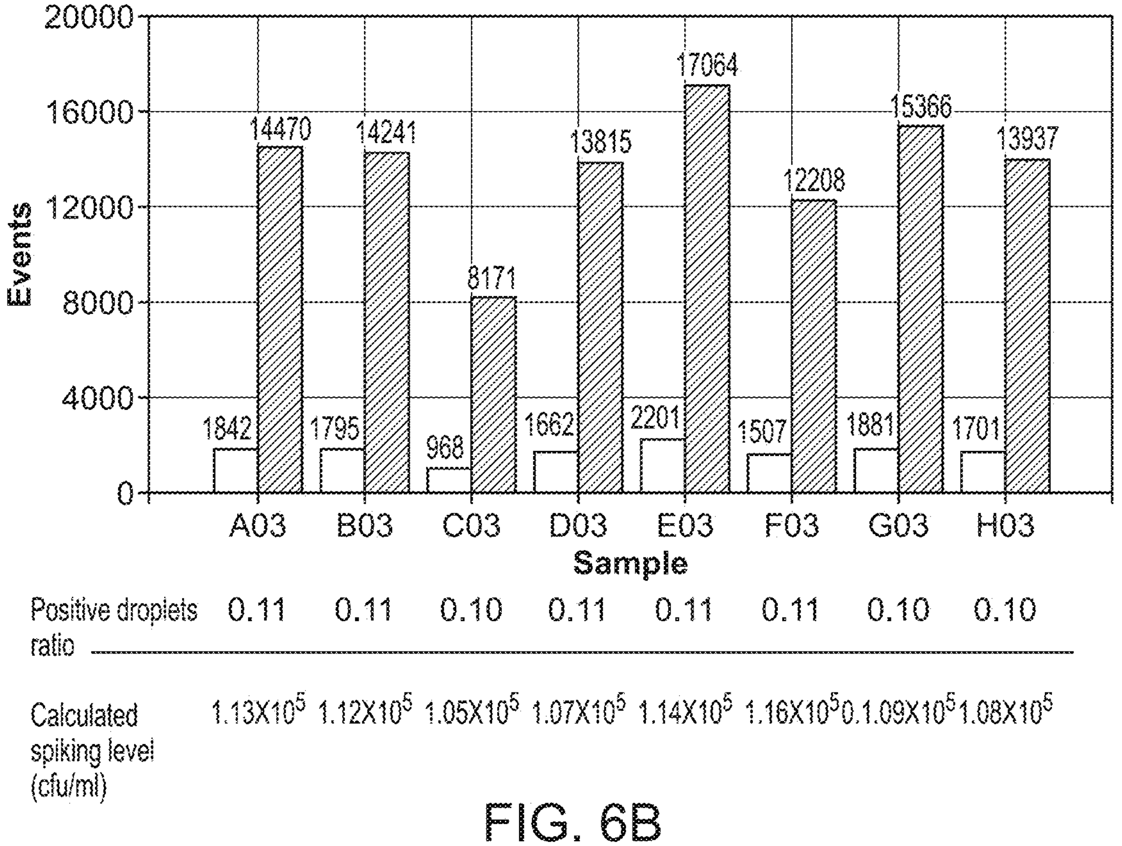
Figure 7A:
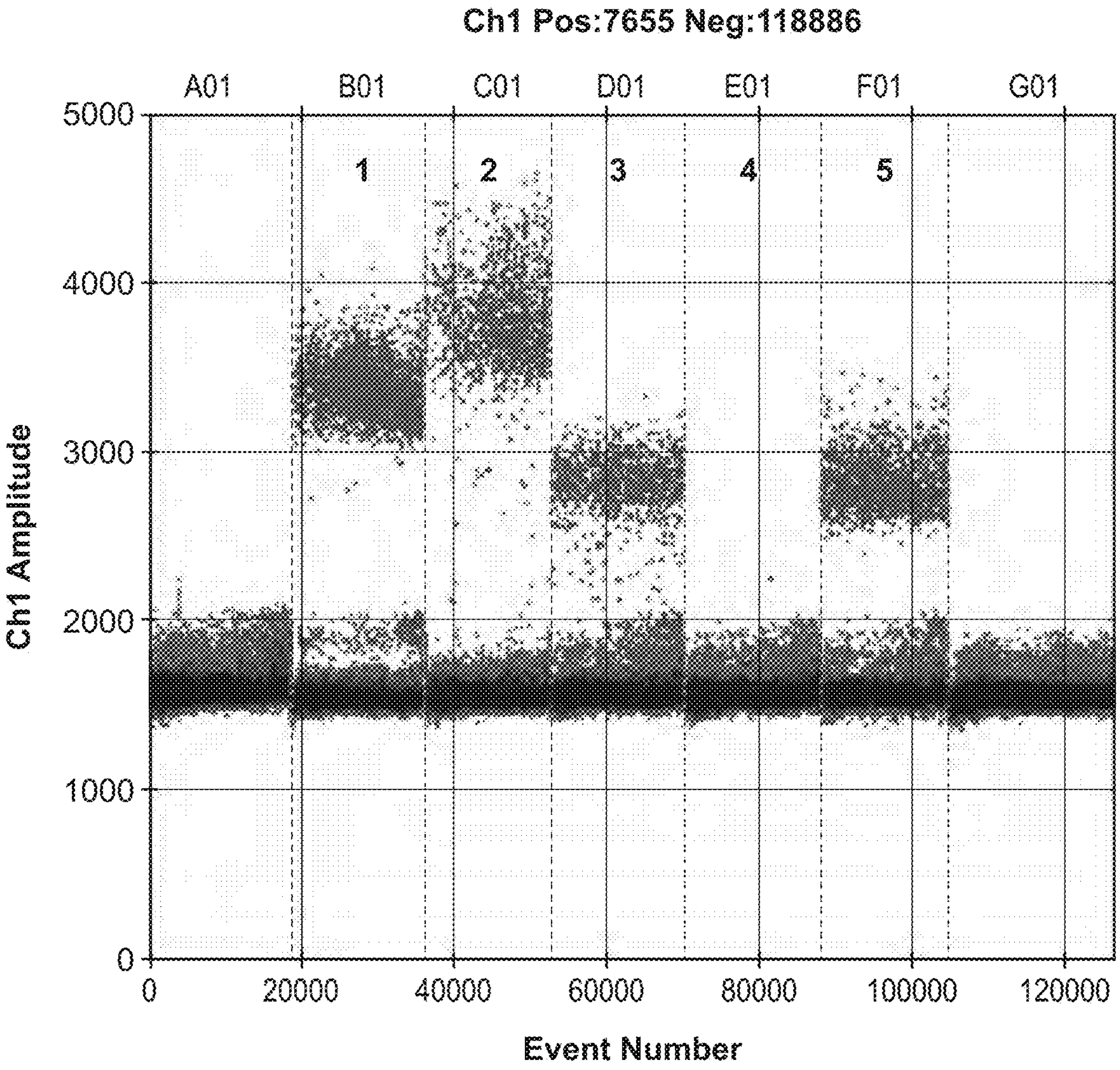
FIGS. 7A-7B illustrate accurate enumeration of target bacteria and yeasts by counting positive and negative droplets in an automated droplet reader.
Figure 7B:
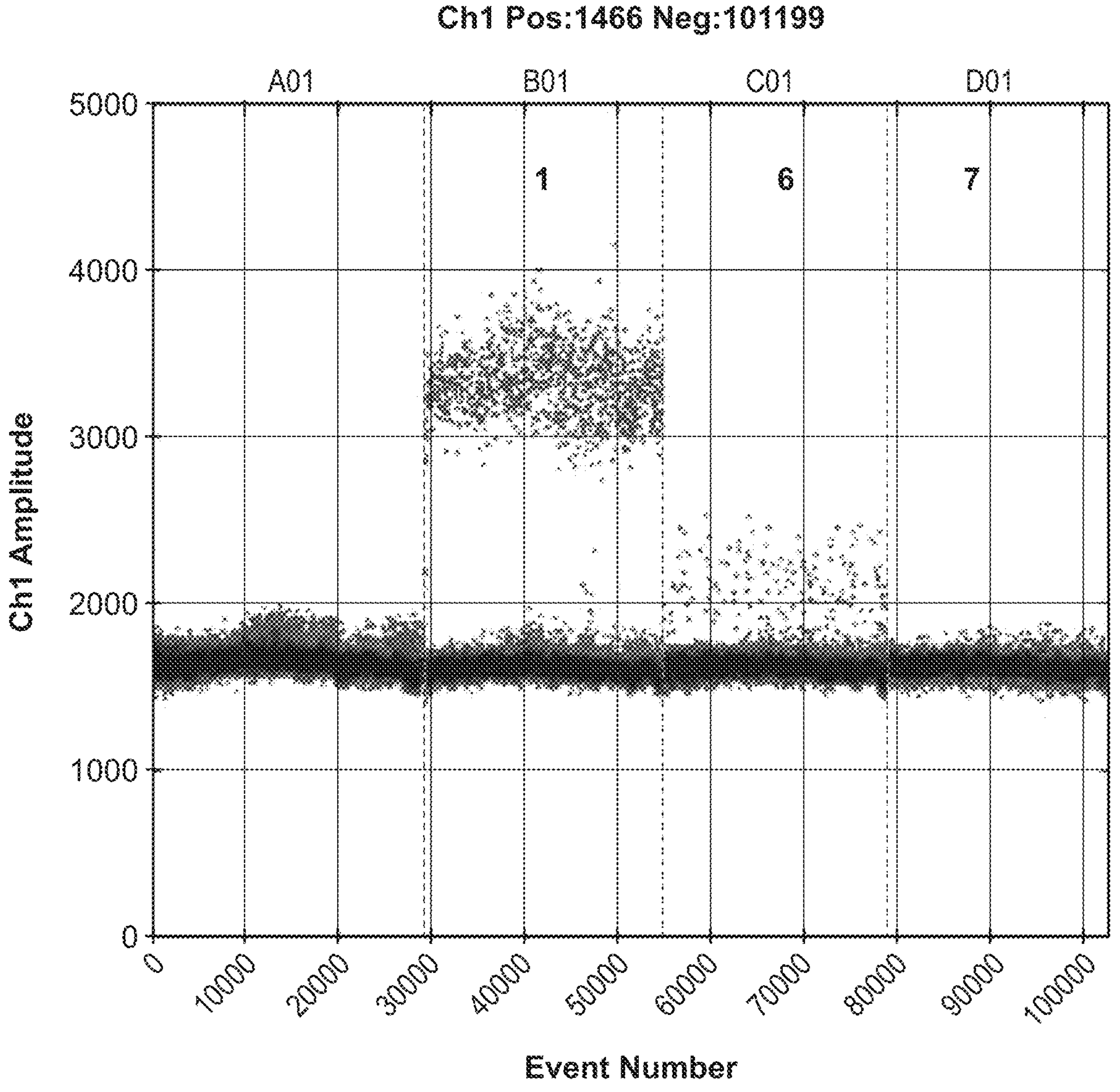
Figure 8A:
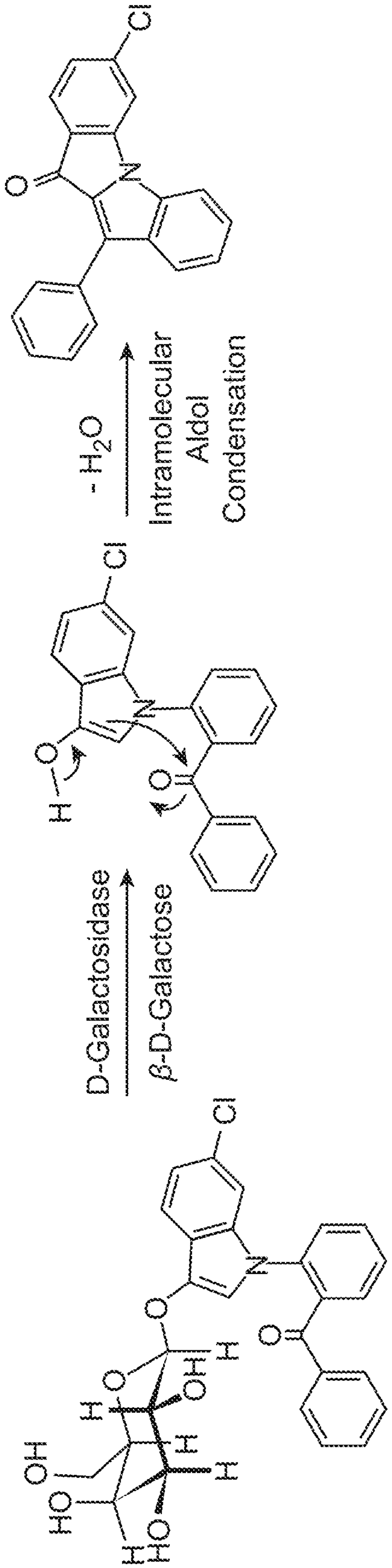
FIGS. 8A-8D illustrate the use of a β-galactosidase substrate for specific detection and/or enumeration of a target microorganism that expresses the β-galactosidase enzyme.
Figure 8B:
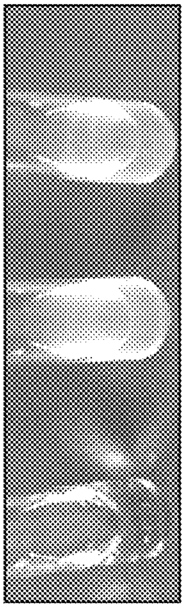
Figure 8C:
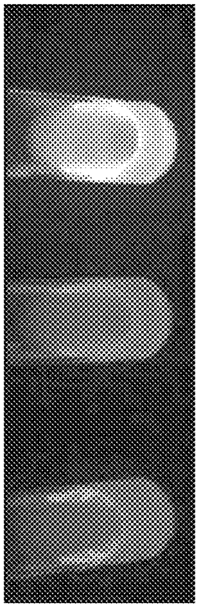
Figure 8D:
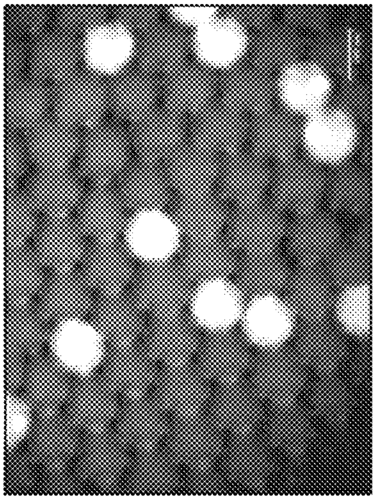

Results: All bacteria (gram negative as well as gram positive) and yeast could be detected by visual examination of droplets within various times following encapsulation (see FIGS. 4 and 5). Autofluorescence was detected, although with various intensities. Enterobacteriaceae gave rise to a strong auto-fluorescence within 8 h, whereas 24 hr were required to obtain a similar signal for *Bacillus subtilis*. *Staphylococcus aureus* elicited a weak signal and *Listeria* (see also 6) did not give rise to a fluorescence signal. All microorganisms could be enumerated using the QX200 reader, although the intensities of the positive droplets varied as a function of the autofluorescence intensity (see FIGS. 6 and 7).

Materials and Methods (Mold)

*Aspergillus niger* T646 (Bio-Rad internal strain collection number) was grown for 5 days on a sabouraud agar.

The spores were then harvested with a loop and were suspended in Buffered Peptone Water.

The spores suspension was diluted in order to obtain a $10^5$ cfu/ml spore suspension in Buffered Peptone Water supplemented with Pluronic F-98 (1%). 20 μl of these suspensions were mixed with 50 μl of QX200™ Droplet Generation Oil for EvaGreen (+surfactant) with the Bio-Rad droplets generator system. The droplets obtained were transferred in a well of an Eppendorf microplate.

The microplate was incubated at 37±1° C. for 24 hours.

After 0, 4, 6, 8 and 24 hours of incubation:

a sample of droplets was observed with the ZOE Fluorescent Cell Imager from Bio-Rad in the visible channel and the blue fluorescence channel.

a sample of droplets was tested with the Bio-Rad droplets reader QX200.

Results: Mold growth could be observed in droplets although, conversely to bacteria and yeast, mold growing led to an observable amount of droplet coalescence, likely due to the protrusion of hyphae through droplet membrane (FIG. 5). Alternative droplet chemistries can be used to prevent this fusion effect. Mold growth gave rise to a weak but detectable autofluorescence.

5. *Listeria* Species

Goal: *Listeria* is a slow growing bacterium. This experiment was undertaken to determine whether *Listeria* growth in droplet can be detected within 24 h. Moreover we also studied whether a specific substrate can be used for detection. Three species of *Listeria* were mixed together to represent a *Listeria* spp. population and grown in droplets in the presence of 4-Methylumbelliferyl-β-D-glucoside.

Materials and Methods

*Listeria monocytogenes* ATCC 13932, *Listeria innocua* ATCC 33090 and *Listeria grayi* ATCC 19120 were grown overnight in Tryptone-Soya Broth.

The cultures were then diluted in order to obtain:

a $10^5$ cfu/ml bacterial suspension in Buffered Peptone Water supplemented with 4-Methylumbelliferyl-β-D-glucoside (100 mg/l) and Pluronic F-98 (1%). 20 μl of this suspension were mixed with 50 μl of QX200™ Droplet Generation Oil for EvaGreen (+surfactant) with the Bio-Rad QX200™ droplet generator system. The droplets obtained were transferred into a well of a microplate.

a 50 cfu/ml bacterial suspension in 5 ml of Buffered Peptone Water supplemented with 4-Methylumbelliferyl-β-D-glucoside (100 mg/l) and Pluronic F-98 (1%).

The microplate and the tubes were incubated at 37±1° C. for 24 hours.

After 0, 4, 6, 8 and 24 hours of incubation:

a sample of droplets was observed with the ZOE Fluorescent Cell Imager in the visible channel and the blue fluorescence channel.

a sample of droplets was tested with the Bio-Rad droplets reader QX200.

In the same time, the 5 ml tube was observed under ultraviolet light using a Wood lamp at 365 nm.

Results: As shown on FIG. 4, bottom right panel, bacterial growth can be detected within 24 h by direct observation of droplets full of bacteria. No fluorescence was detected, thereby indicating that i) no auto-fluorescence was generated by *Listeria* growth and ii) the MUG substrate was not metabolized or not metabolised enough to elicit a detectable signal as already noted with *E. coli*. Growth can likely be detected in a shorter time under optimized conditions. More sensitive substrates can be readily screened. Moreover this experiment was carried out with a media that is not optimized for *Listeria* growth. Better results are expected with a dedicated broth.

6. Use of an ALDOL® Substrate for Detection of Coliform Bacteria (*E. coli*)

Goal: A green fluorescence substrate specific for β-galactosidase expressing coliforms such as *E. coli* was performed to assess whether alternative substrates could perform better than MUG.

Materials and Methods (Bacteria and Yeast)

*E. coli* ATCC 25922 was grown overnight in Tryptone-Soya Broth.

The culture was diluted in order to obtain a $10^5$ cfu/ml bacterial suspension in Buffered Peptone Water supplemented with Aldol®458-β-D-galactoside (100 mg/l) and Pluronic F-98 (1%). 20 μl of this suspension were mixed with 50 μl of QX200™ Droplet Generation Oil for EvaGreen (+surfactant) with the Bio-Rad QX200™ droplet generator system. The droplets obtained were transferred to a well of a microplate.

The microplate was incubated at 37±1° C. for 24 hours.

After 0, 4, 6, 8 and 24 hours of incubation:

a sample of droplets was observed with the ZOE Fluorescent Cell Imager from Bio-Rad in the visible channel and the green fluorescence channel.

a sample was tested with the Bio-Rad QX200 droplet reader.

Results: After 6 h, a clear green fluorescent signal was observable (see FIG. 8). This signal was different from the blue fluorescence obtained in similar conditions in absence of the substrate. The fluorescence could be read on the FAM channel of the QX reader (not shown) and gave rise to a stronger fluorescence than the blue autofluorescence, thereby demonstrating that a specific substrate can be used to identify bacteria in droplets.

7. Detection of Microorganisms Using an Antibody as a Marker

Figure 9A:
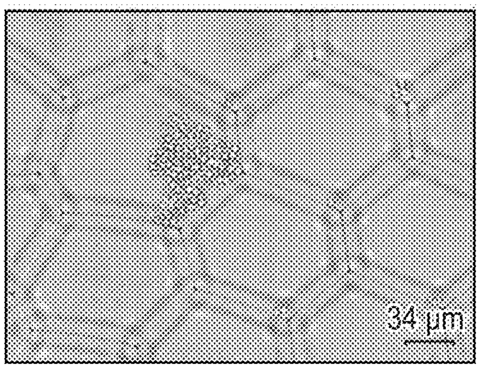
FIGS. 9A-9B illustrate detection of *C. albicans* in droplets without incubation.
Figure 9B:
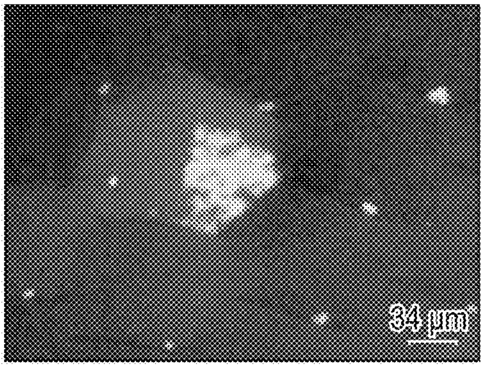

An anti-*Candida* antibody Ac EBCA1 (Bio-Rad Laboratories) that recognizes *C. albicans* was labeled using Kit Lynx LNK024RPE (Abd Serotec). After overnight cultures in sabouraud agar (Bio-Rad Laboratories), droplets were first made by adding a mixture (v/v) of *C. albicans* ATCC®24433™ (1McFarland) to dilutions of the conjugate from 1/25 to 1/200. The samples were read using the ZOE™ Fluorescent Cell Imager (Bio-Rad Laboratories). FIGS. 9A and 9B show clear fluorescence at (To) using an inoculum equivalent to 1McFarland and conjugate at 1/200.

Figure 10A:
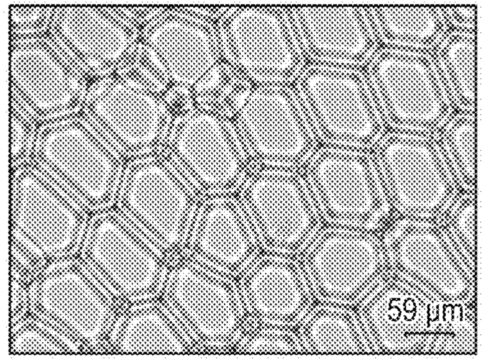
FIGS. 10A-10C illustrate *C. albicans* inoculum equivalent to 0.1 McFarland and conjugate at 1/200 after 5 hours of incubation.
Figure 10B:
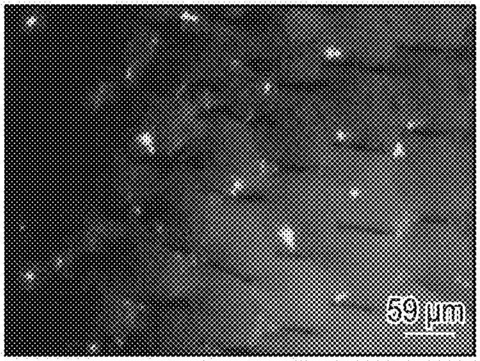
Figure 10C:
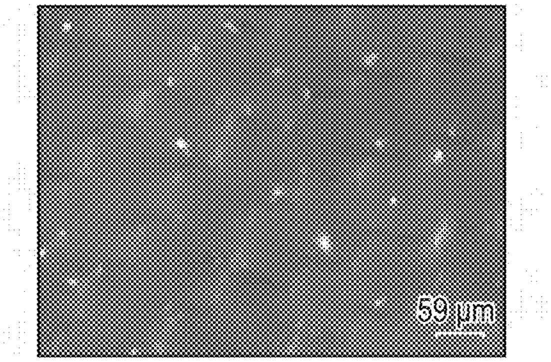
Figure 11A:
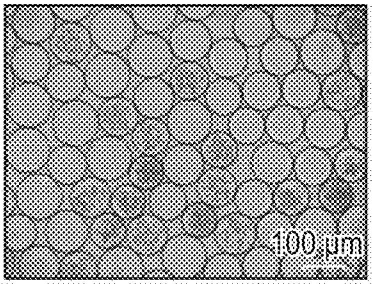
FIGS. 11A-11C illustrate *C. albicans* inoculum equivalent to 0.1McFarland and conjugate at 1/200 after 24 hours.
Figure 11B:
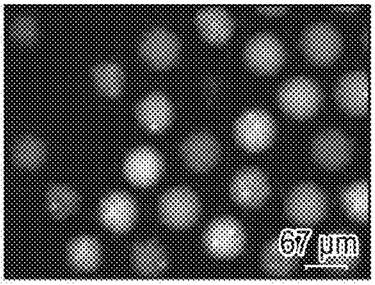
Figure 11C:
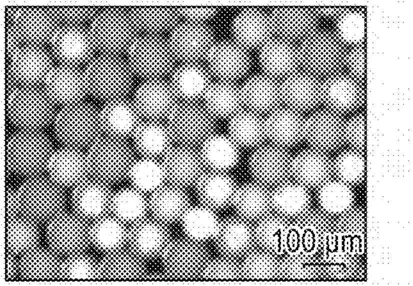

In an additional experiment, droplets were made by adding a mixture (v/v) of a reduced inoculum of *C. albicans* ATCC®24433™ (0.1 McFarland) to dilutions of the conjugate from 1/25 to 1/200, then were incubated at 30° C. The samples were read using the ZOE™ Fluorescent Cell Imager (Bio-Rad Laboratories) after 5 h or 24 h. FIGS. 10A-10C are images of inoculum equivalent to 0.1 McFarland and conjugate at 1/200 after 5 hours. FIGS. 11A-11C are images of inoculum equivalent to 0.1McFarland and conjugate at 1/200 after 24 hours.

Figure 12A:
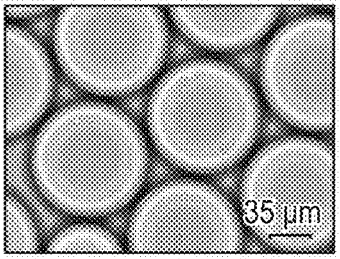
FIGS. 12A-12B illustrate *C. parapsilosis* inoculum equivalent to 1McFarland and conjugate at 1/200 without incubation.
Figure 12B:
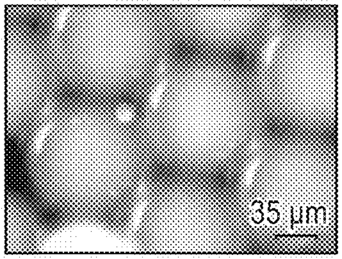

*C. parapsilosis* (ATCC®22019™), to which the antibody does not specifically bind, was studied in the same way as *C. albicans* above. FIGS. 12A and 12B are images of inoculum equivalent to 1McFarland and conjugate at 1/200 at $T_0$. No microorganism is visible as would be expected as the antibody does not specifically bind *C. parapsilosis.*

In another experiment, an anti-PBP2a antibody (Biosource clone M0071933) that recognizes PBP2a indicative of the resistance against methicillin in *Staphylococcus aureus* (SA) was labeled using Kit Lynx LNK174PETR (Abd Serotec). After overnight cultures on blood agar plates (Bio-Rad Laboratories), droplets were first made by adding colonies of each of the 4 tested strains of MSSA and MRSA (1/50 of a 0.5 McFarland, equivalent to approximately 1-10 bacterial cell in 20 droplets) to the conjugate at 1/200 supplemented by Bovine serum albumin (BSA)+/− cefoxitin (FOX at 0 or 2 mg/L) in broth. After incubation at 37° C. for 3 hours, the samples were read using the ZOE™ Fluorescent Cell Imager (Bio-Rad Laboratories). The tables below show growth (visible) and labeling (fluorescence) obtained for the tested strains of MSSA and MRSA.

| Strains | BSA 0 + FOX 0 | BSA 25% + FOX 0 | BSA 0 + FOX 2 | BSA 2.5% + BSA FOX 2 |
|---|---|---|---|---|
| MSSA ATCC 6538 | Growth + | Growth +> | Growth − | Growth − |
| MSSA ATCC 29213 | Growth (+) | Growth +> | Growth − | Growth − |
| MRSA ATCC 49476 | Growth ((+)) | Growth (+) | Growth ((+)) | Growth + |
| MRSA ATCC BAA 2312 | Growth + | Growth +> | Growth +< | Growth +> |

| Strains | BSA 0 + FOX 0 | BSA 2.5% + FOX 0 | BSA 0 + FOX 2 | BSA 2.5% FOX 2 |
|---|---|---|---|---|
| MSSA ATCC 6538 | Fluo ++ to +++ | Fluo ++ to +++ | BN − | BN − |
| MSSA ATCC 29213 | Fluo + to ++ | Fluo +++ | BN (+) | BN (+) |
| MRSA ATCC 49476 | Fluo + to ++ | Fluo +++ | Fluo +/ BN (+) | Fluo +++ |
| MRSA ATCC BAA 2312 | Fluo + | Fluo ++ to +++ | Fluo+ | Fluo ++ to +++ |

BSA was added to the broth to increase the growth and to aid the identification of the SA strains. Adding BSA promotes the production of a micro-colony of bacterial cells (i.e., the bacterial cells form a cluster instead of remaining single) which in turn emits a stronger detection signal, thereby aiding detection of microorganism.

The antibody detected both MRSA and MSSA when it was supposed to be specific for MRSA, FOX was then added to inhibit specifically the growth of MSSA and to obtain a fluorescent signal limited to MRSA. Background noise (BN) was observed due to fluorescence not related to bacterial cells. The concentration of antibody may be adjusted to reduce background fluorescence.

The results show that MRSA could be detected in droplets even at a low concentration within 3 hours by using a combination of labeled antibody, BSA and cefamycin.

8. Detection of Microorganisms Using Fibrinogen as a Marker

Fibrinogen (Sigma Aldrich) that binds to *Staphylococcus aureus* (*S. aureus* cells express surface proteins that promote attachment to host proteins such as fibronectin) was labeled using Kit Lynx LNK174PETR (Abd Serotec). After overnight cultures on blood agar plates (Bio-Rad Laboratories), droplets were first made by adding a suspension of colonies of each of the 4 tested strains of MSSA and MRSA (1/50 of a 0.5 McFarland, equivalent to approximately 1-10 bacterial cell in 20 droplets) to the conjugate at 1/200 supplemented by Bovine serum albumin (BSA)+/− cefoxitin (FOX at 0 or 2 mg/L) in broth. After incubation at 37° C. for 3 hours, the samples were read using the ZOE™ Fluorescent Cell Imager (Bio-Rad Laboratories). The tables below show growth (visible) and labeling (fluorescence) obtained for the tested strains of MSSA and MRSA.

| Strains | BSA 0 + FOX 0 | BSA 2.5% + FOX 0 | BSA 0 + FOX 2 | BSA 2.5% + FOX 2 |
|---|---|---|---|---|
| MSSA ATCC 6538 | Growth + | Growth +> | Growth − | Growth − |
| MSSA ATCC 29213 | Growth (+) | Growth + | Growth − | Growth − |
| MRSA ATCC 49476 | Growth (+) | Growth (+) | Growth (+) | Growth + |
| MRSA ATCC BAA 2312 | Growth − | Growth +(+) | Growth − | Growth +(+) |

| Strains | BSA 0 + FOX 0 | BSA 2.5% + FOX 0 | BSA 0 + FOX 2 | BSA 2.5% + FOX 2 |
|---|---|---|---|---|
| MSSA ATCC 6538 | Fluo +++ | Fluo +++ | BN (+) | BN (+) |
| MSSA ATCC 29213 | Fluo ++ to +++/ BN (+) | Fluo +++ | BN (+) | BN (+) |
| MRSA ATCC 49476 | Fluo +++ | Fluo +++ | Fluo ++ to +++/BN (+) | Fluo +++ |
| MRSA ATCC BAA2 312 | BN (+) | Fluo +++ | BN (+) | Fluo +++ |

The results show that MRSA could be detected in droplets even at a low concentration within 3 hours by using a combination of labeled fibrinogen, BSA and cefamycin.

9. Detection of Microorganisms Using an Intercalating Agent as a Marker

A solution of 1 mg/mL of propidium iodide ("PI" from Sigma Aldrich) was prepared and 400 μL were added to 9 ml TCS broth (Bio-Rad Laboratories) previously spiked with *S. aureus* ATCC®29213™ ("SA") at 0.005McFarland. 10 μL of this mix with 10 μL of various concentrations of cefoxitin ("FOX") were used to prepare droplets. The samples were read using the ZOE™ Fluorescent Cell Imager (Bio-Rad Laboratories) over time up to 8 h. The results demonstrate that PI can be used to identify the presence or absence of a particular microorganism in a sample without a lysing agent being added to the reaction.

Figure 13A:
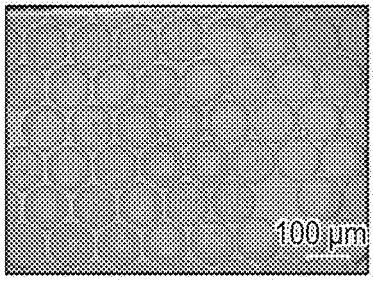
FIGS. 13A-13B are a sample of *S. aureus* ("SA")+propidium iodide ("PI") without cefoxitin ("FOX") after 6 h of incubation.
Figure 13B:
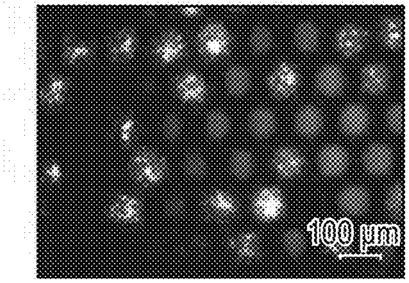
Figure 14A:
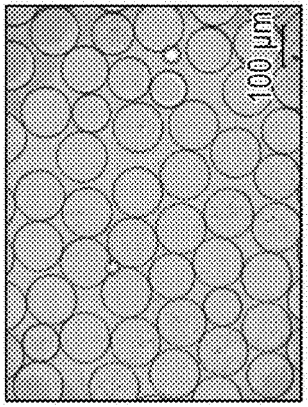
FIGS. 14A-14C are a sample of SA+PI+0.25 mg/L FOX after 6 h of incubation.
Figure 14B:
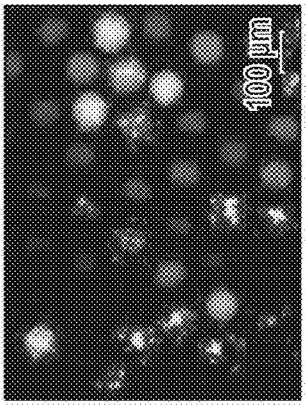
Figure 14C:
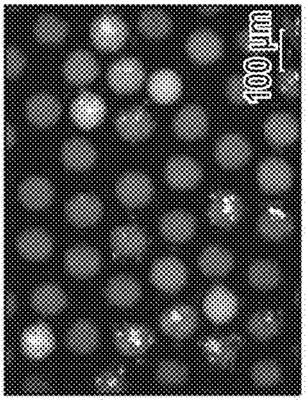
Figure 15A:
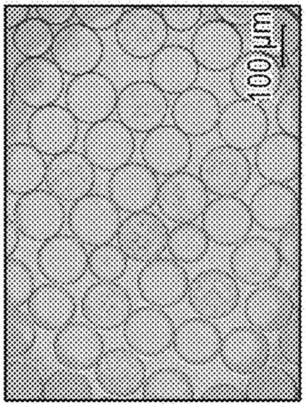
FIGS. 15A-15C are a sample of SA+PI+0.5 mg/L FOX after 6 h of incubation.
Figure 15B:
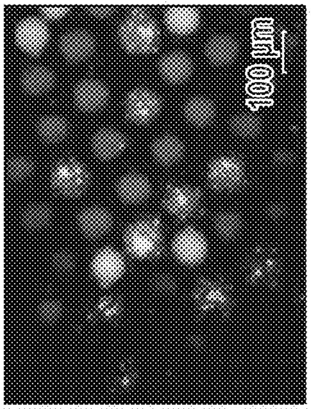
Figure 15C:
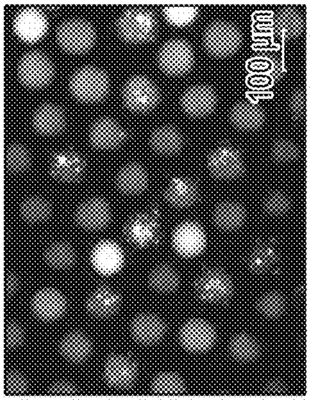
Figure 16A:
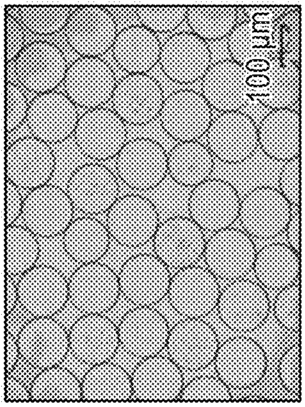
FIGS. 16A-16C are a sample of SA+PI+4 mg/L FOX after 6 h of incubation.
Figure 16B:
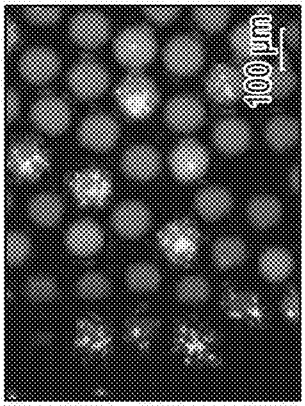
Figure 16C:
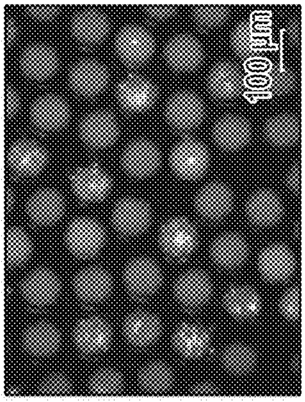

FIGS. 13A and 13B are a sample of SA+PI without FOX after 6 h of incubation. FIGS. 14A-14C are SA+PI+0.25 mg/L FOX after 6 h of incubation. FIGS. 15A-15C are SA+PI+0.5 mg/L FOX after 6 h of incubation. FIGS. 16A-16C are SA+PI+4 mg/L FOX after 6 h of incubation. PI is excluded from viable cells and penetrates the cell membranes of dead or dying cells. Surprisingly, PI labeled all viable cells in this experiment. Intercalating agents are considered toxic for cell growth because they react with DNA, blocking the replication of the cells. However, by following the turbidity of a bacterial culture over time in the presence and absence of PI, the inventors observed that PI allowed growth of bacteria or yeast with only a limited impact.

10. Detection of Microorganisms Using an Intercalating Agent as a Marker and Using an Additional Heating Step Goal: To determine if using an intercalating agent along with an additional heating step enhances the fluorescent signal detected from droplets having bacterial cells.

Materials and Methods

Figure 17A:
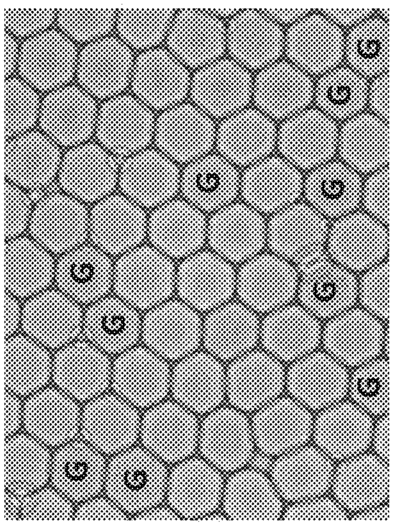
FIGS. 17A-17F illustrate the use of propidium iodide and a heating step to enhance the fluorescent signal detected from droplets having bacterial growth (G). Droplets were formed from buffered peptone water broth spiked with *E. coli* ATCC 25922 in the absence (FIGS. 17A and 17D) or presence (FIGS. 17B-17C and 17E-17F) of propidium iodide. The droplets were incubated 24 hours at 37° C. The droplets shown in FIGS. 17C and 17F were also heated at 90° C. for 5 minutes.
Figure 17B:
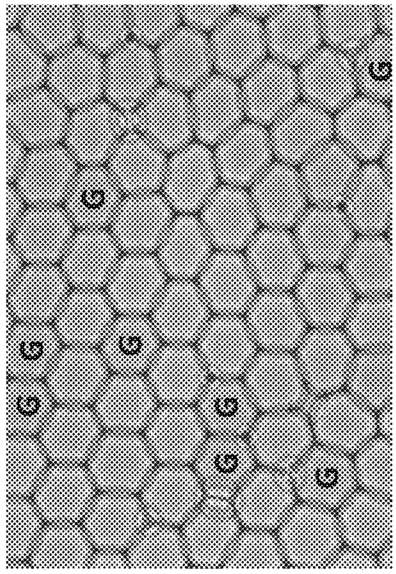
Figure 17C:
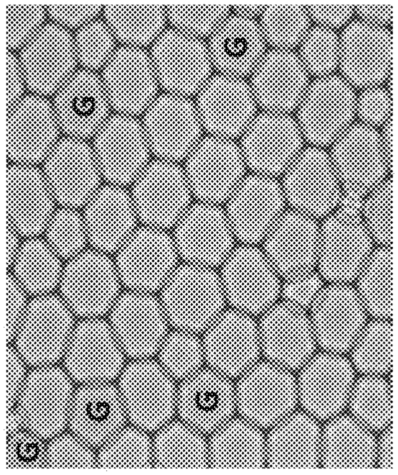
Figure 17D:
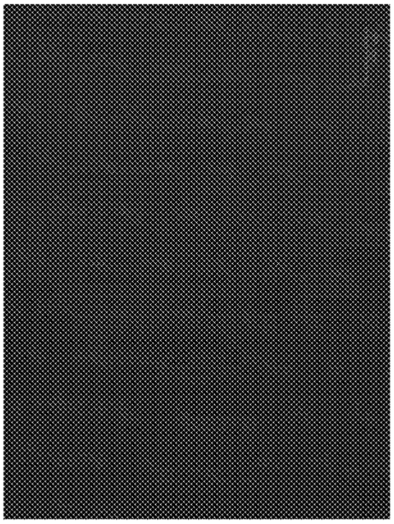
Figure 17E:
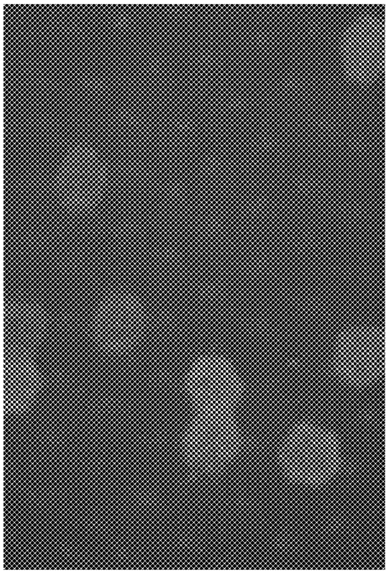
Figure 17F:
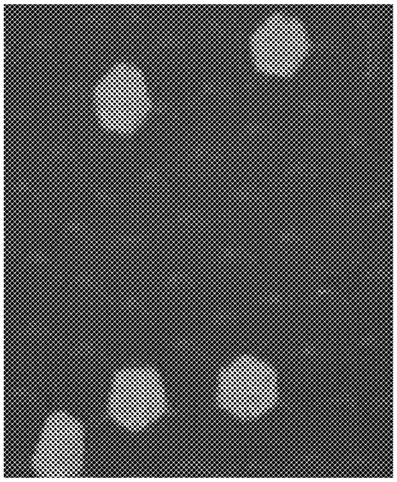

- Buffered peptone water broth without and with 15 µM propidium iodide (PI) was spiked with *Escherichia coli* ATCC 25922.
- Droplets were then produced with the Bio-Rad QX200™ Droplet Generator and EvaGreen oil such that one out of ten droplets contained a single bacterial cell. The droplets were transferred to a microwell and were incubated for 24 hours at 37° C.
- A portion of the droplets having propidium iodide were also heated at 90° C. for 5 minutes.
- The droplets were then imaged with a ZOE™ Fluorescent Cell Imager using a bright-field channel (FIGS. 17A-17C) or with a red fluorescent filter (FIGS. 17D-17F).

Results: As shown in FIGS. 17A-17C, bacterial growth (G) was observed in buffered peptone water with no PI, with PI, and with PI plus an additional heating step. However, no fluorescence signal was observed from any of the droplets when no PI was present (FIG. 17D). A weak fluorescent signal was observed from droplets having bacteria and PI (FIG. 17E), indicating that PI can be used to differentiate between droplets having bacterial growth from empty droplets. As shown in FIG. 17F, heating droplets having bacteria and PI at 90° C. for 5 minutes enhances the fluorescence signal.

11. Detection of Microorganisms Using pHrodo® Red as a pH Indicator

Goal: To determine if microorganisms can be detected with pHrodo® Red.

Materials and Methods (Bacteria and Yeast)

Figure 18A:
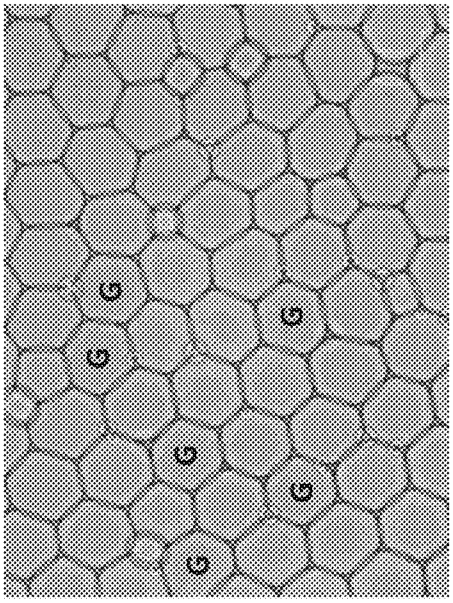
FIGS. 18A-18D illustrate the use of a pH indicator for detection of microorganisms. Droplets were formed from tryptone-glucose broth spiked with *E. coli* ATCC 25922 in the absence (FIGS. 18A and 18C) or presence (FIGS. 18B and 18D) of pHrodo® Red.
Figure 18B:
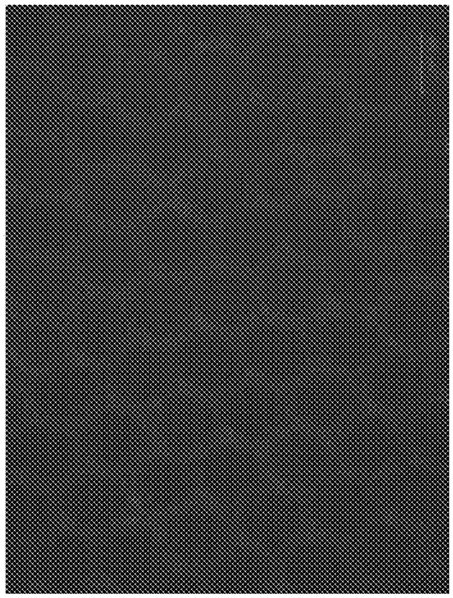
Figure 18C:
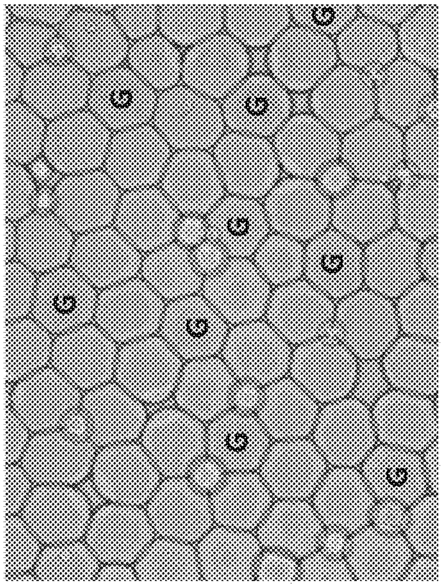
Figure 18D:
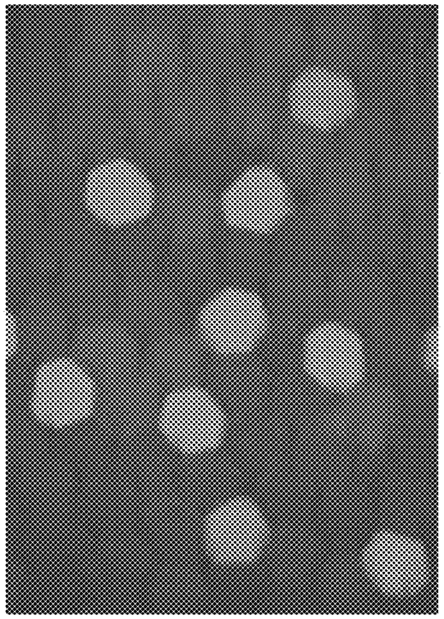

- Tryptone-glucose broth without and with 5 µM pHrodo® Red were spiked with *E. coli* ATCC 25922.
- Droplets were then produced with the Bio-Rad QX200™ Droplet Generator and EvaGreen oil such that one out of ten droplets contained a single bacterial cell. The droplets were transferred to a microwell and were incubated for 24 hours at 37° C.
- The droplets were then imaged with a ZOE™ Fluorescent Cell Imager using a bright-field channel (FIGS. 18A and 18C) or with a red fluorescent filter (FIGS. 18B and 18D).

Results: In the absence of pHrodo® Red, no fluorescence was observed in droplets having bacterial growth G (FIG. 18B). In the presence of pHrodo® Red, droplets having bacterial growth produce red fluorescence due to a change in pH indicator properties in the presence of acid following glucose fermentation (FIG. 18D), thereby demonstrating that a pH indicator can be used to identify bacteria in droplets.

12. Use of an ALDOL518® Substrate for Detection of Coliform Bacteria (*Enterobacter aerogenes*)

Goal: A red fluorescence substrate specific for β-glucosidase expressing coliforms such as *Enterobacter aerogenes* ATCC 13048 was performed to assess whether alternative substrates could perform better than MUG.

Materials and Methods

Figure 19A:
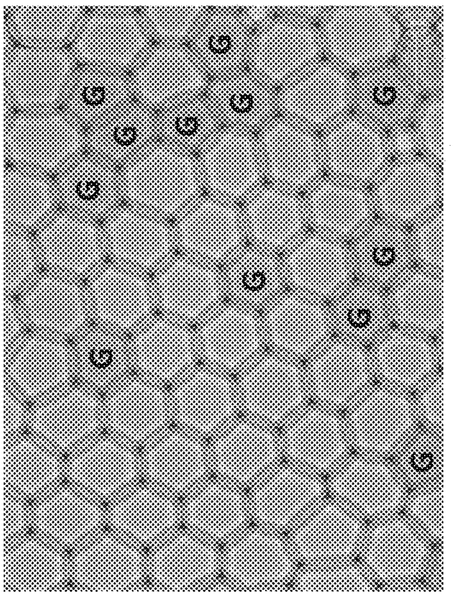
FIGS. 19A-19D illustrate the use of a β-glucoside substrate for specific detection and/or enumeration of a target microorganism that expresses the β-glucosidase enzyme. Droplets were formed from buffered peptone water broth spiked with *Enterobacter aerogenes* ATCC 13048 in the absence (FIGS. 19A and 19C) or presence (FIGS. 19B and 19D) of ALDOL®518-β-glucoside.
Figure 19B:
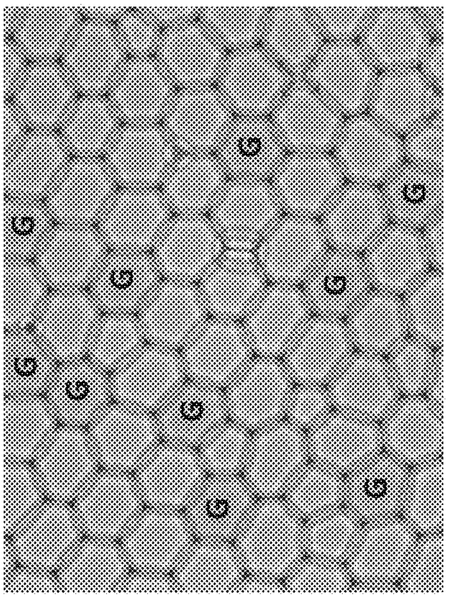
Figure 19C:
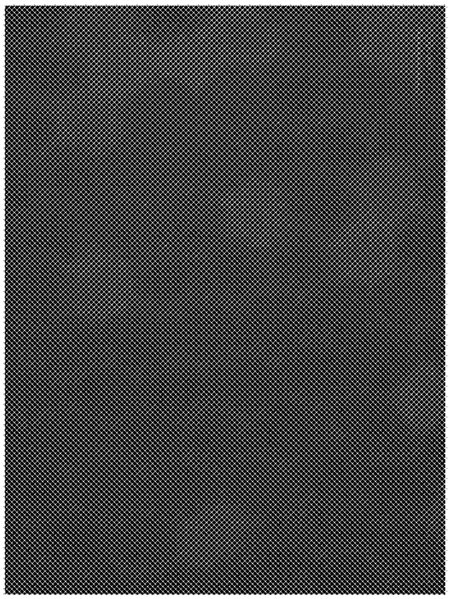
Figure 19D:
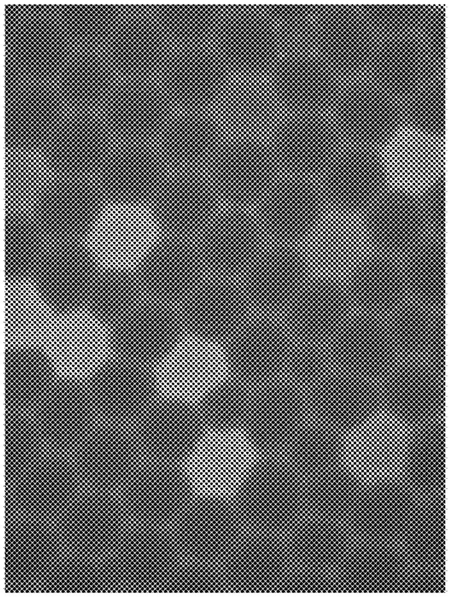

- Buffered peptone water broth without and with ALDOL518®-β-glucoside at 250 mg/L were spiked with *Enterobacter aerogenes* ATCC 13048.
- Droplets were produced with the Bio-Rad QX200™ Droplet Generator and EvaGreen oil to obtain 10,000 bacteria per droplet. These droplets were then diluted with droplets containing the same broth but no bacteria. The droplets obtained were transferred to a well of a microplate.
- The microplate was incubated at 37±1° C. for 24 hours. The droplets were imaged with a ZOE™ Fluorescent Cell Imager using a bright-field channel (FIGS. 19A and 19B) or with a red fluorescent filter (FIGS. 19C and 19D).

Results: In the absence of ALDOL518®-β-glucoside, no fluorescence was observed in droplets having bacterial growth (FIG. 19C). In the presence of ALDOL518®-β-glucoside, the β-glucosidase activity of *Enterobacter aerogenes* ATCC 13048 hydrolyzes the substrate and releases a fluorescent ALDOL compound such that droplets having bacterial growth produce red fluorescence (FIG. 19D), thereby demonstrating that a specific substrate can be used to identify bacteria in droplets.

13. Inhibition of Mold Growth Outside the Droplet Aqueous Phase Using Dicloran

Goal: To determine if including an antifungal agent (e.g., dicloran) in the droplet oil phase inhibits mold growth outside the droplet aqueous phase.

Materials

| Reagent | Supplier | Reference | CAS number |
|---|---|---|---|
| Dicloran (2,6-Dichloro-4-NitroAniline) | Sigma Aldrich | D67820 | 99-30-9 |
| Acetone | VWR | 20066.31 | 67-64-1 |
| CFDA (5(6)-Carboxyfluorescein diacetate) | Sigma Aldrich | 21879 | 124387-19-5 |
| DMSO (Dimethylsulfoxide) | VWR | 23846.297 | 67-68-5 |
| YGC broth | | | |
| Yeast extract | Bio-Rad | 5 g/L | N/A |
| Glucose | | 20 g/L | |
| Chloramphenicol | | 0.3 g/L | |

| Droplet generation component | Supplier | Reference |
|---|---|---|
| Oil for Eva Green | Bio-Rad | 186-4006 |
| Pluronic F68 surfactant 10% | DBC | — |
| DG8 cartridge | Bio-Rad | 186-4008 |
| DG8 gasket | Bio-Rad | 186-3009 |
| TC20 counting slide | Bio-Rad | 1450011 |

Methods

Preparation of Spore Stock Suspensions

Usual foodborne mold strains were grown until the sporulation state (usually for 5 to 7 days) on the appropriate culture medium at 28° C. Spores were then scraped into 0.05% Tween 80 sterile solution. The collected suspensions were filtered on several layers of gauze compressed to eliminate most of the hyphae and mycelium fragments. When necessary, the suspensions were kept under stirring in the dark and at room temperature before the filtration step to ensure optimal spore release from the fungal structures. The spore concentration was determined in a hemocytometer chamber and/or by plating on agar Petri plates.

The suspensions were then centrifuged for 5 minutes at 10.000 rpm and the supernatants discarded. The pellets were resuspended with the appropriate volume of YGC broth containing 30% of glycerol and the aliquots were stored at −20° C. for up to 6 months.

Sample Preparation for Droplet Generation

Aliquots were thawed at room temperature and washed once in YGC broth to remove glycerol. The spores were then diluted to the concentration of $10^5$ spores/mL in YGC broth containing 5% of Pluronic F68 surfactant.

For the detection assay, fluorogenic substrate CFDA (5 (6)-Carboxyfluorescein diacetate) was added to the YGC broth. The substrate was prepared by dissolving 10 mg in 1 mL of DMSO (Dimethylsulfoxide) and 28.75 μL of this solution was added to 10 mL of YGC broth.

The CFDA was used at the final concentration of 25 mg/L taking into account the 15%-dilution factor due to the surfactant and inoculum volumes.

Addition of Dicloran to Eva Green Oil

Dicloran stock solution was prepared at 40 mg/mL in acetone. The stock solution was then diluted to produce working solutions according to table below.

| Dicloran working solution (mg/L) | Dicloran stock solution (μL) | Acetone (μL) |
|---|---|---|
| 4 | 100 | 900 |
| 6 | 150 | 850 |
| 8 | 200 | 800 |
| 12 | 300 | 700 |
| 16 | 400 | 600 |
| 20 | 500 | 500 |

A volume of 10 μL of the appropriate working solution was then added to 2 mL of Oil for Eva Green to reach the targeted final concentrations (0.5% v/v) (see the table below).

| Dicloran working solution (mg/L) | Dicloran final concentration in Oil for Eva Green (mg/L) |
|---|---|
| 4 | 20 |
| 6 | 30 |
| 8 | 40 |
| 12 | 60 |
| 16 | 80 |
| 20 | 100 |

Droplet Generation and Analysis

For droplet generation using the QX200™ Droplet generator, the 'sample' and 'oil' wells of a DG8 cartridge were respectively filled with 20 μL of the prepared spore suspension (with or without CFDA) and 70 μL of the Oil for Eva Green (with or without Dicloran). After the generation process, the droplet emulsions (30-35 μL/well) were transferred to a 96-well Eppendorf plate and placed at 28° C. for 24 to 48 hours. For analysis, the droplet emulsions (20 μL/sample) were observed with the ZOE™ fluorescent cell imager.

Figure 20A:
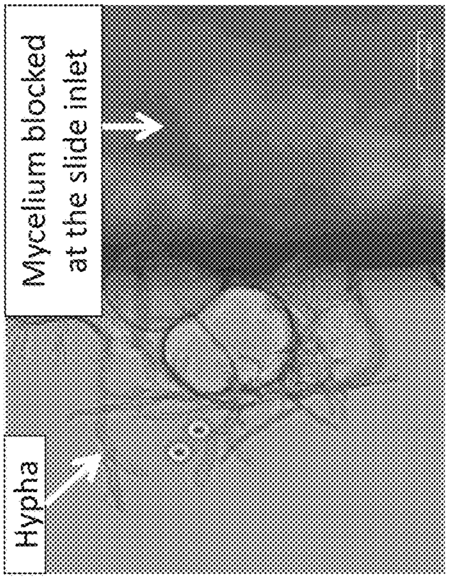
FIGS. 20A-20B illustrate a control condition in which no antifungal compound was included in the oil phase of water-in-oil droplets having mold spores (i.e., *Fusarium graminearum* DSM 1096) in the water phase. After 48 hours of incubation, mold hyphae were able to cross droplet membranes, resulting in droplet coalescence (FIG. 20A). Further growth led to sporulation (FIG. 20B).
Figure 20B:
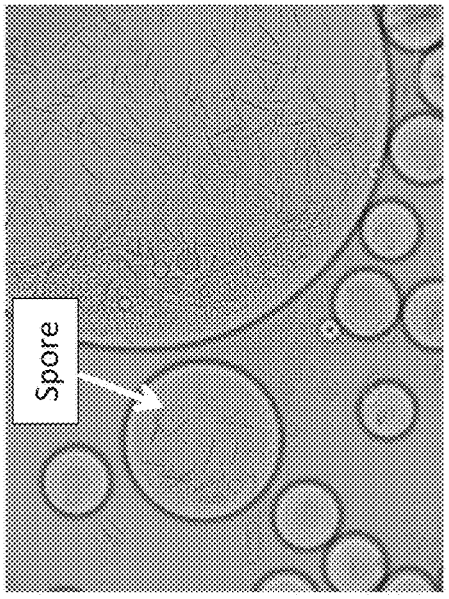
Figure 21A:
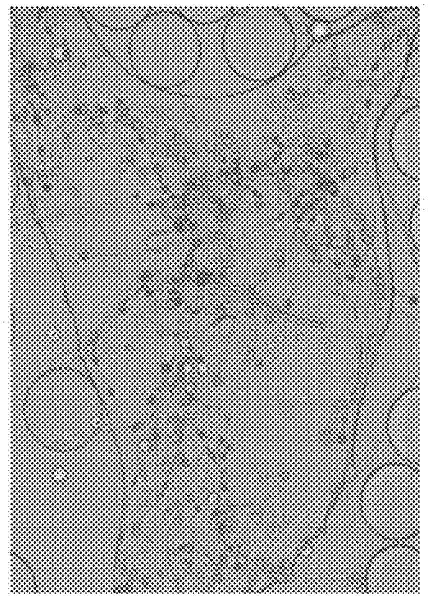
FIGS. 21A-21B illustrate inhibition of mold growth outside the aqueous phase when 60 mg/L dicloran is included in the oil phase of the water-in-oil droplets.
Figure 21B:
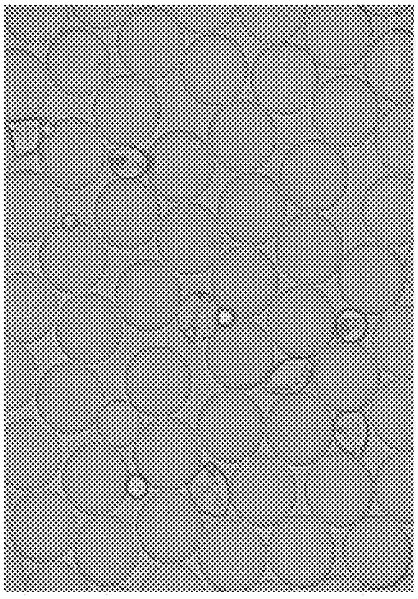
Figure 22A:
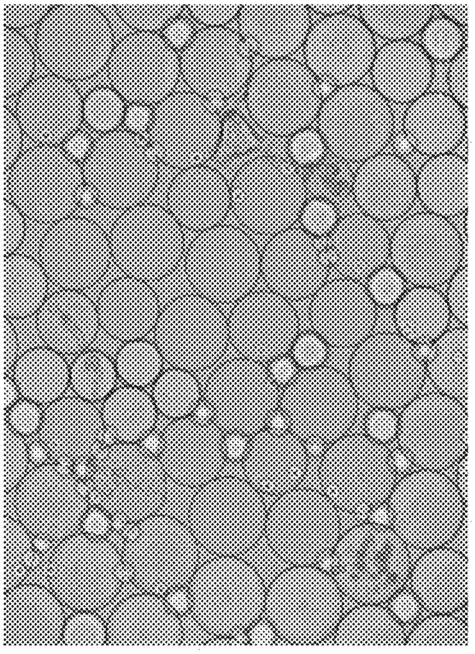
FIGS. 22A-22D illustrate inhibition of mold growth outside the aqueous phase when 40 mg/L dicloran is included in the oil phase of the water-in-oil droplets. *Mucor racemosus* CECT 20821 in YCG broth was incubated for 48 hours in the presence of dicloran in the oil phase. Fluorogenic substrate 5,6 carboxyfluorescein diacetate (25 mg/dL) was added to the broth for the images shown in FIGS. 22C and 22D).
Figure 22B:
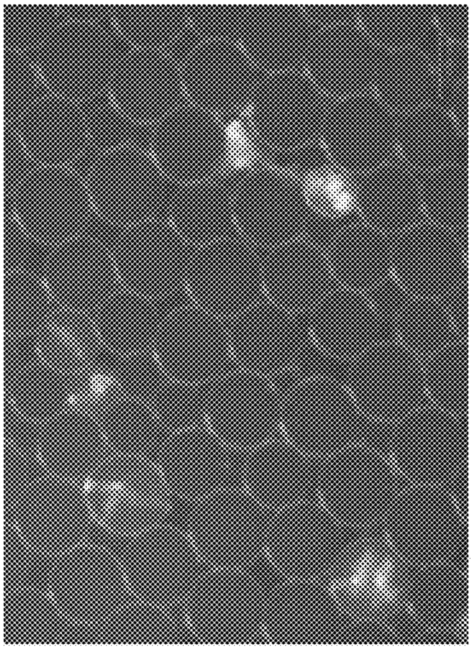
Figure 22C:
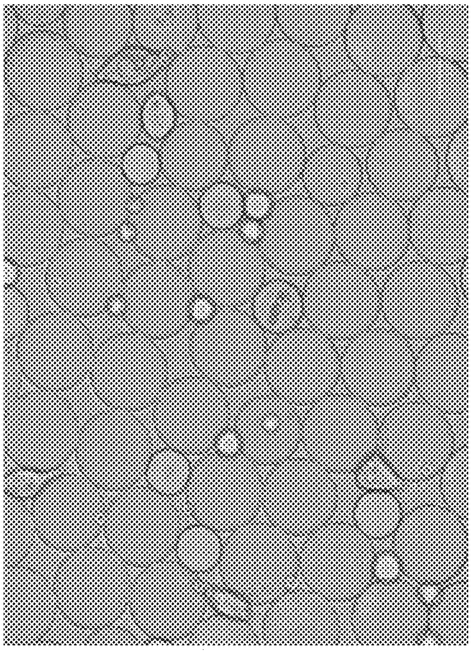
Figure 22D:
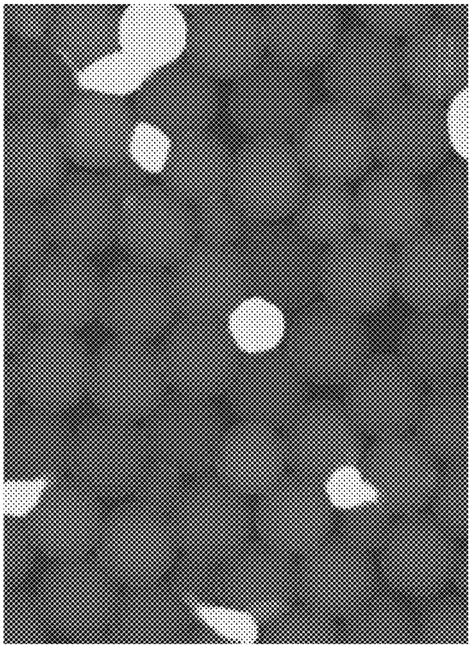
Figure 23A:
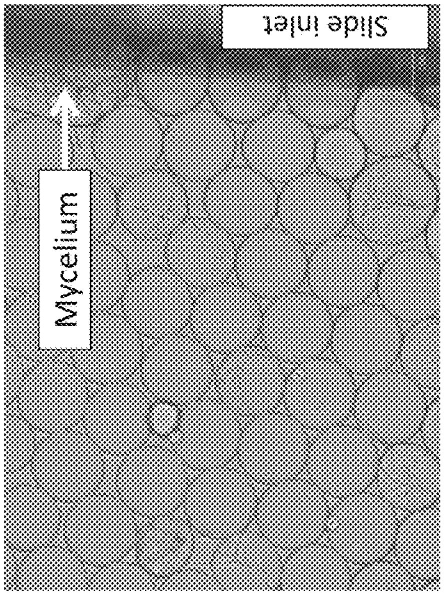
FIGS. 23A-23B illustrate inhibition of mold growth outside the aqueous phase when 80 mg/L dicloran is included in the oil phase of the water-in-oil droplets.
Figure 23B:
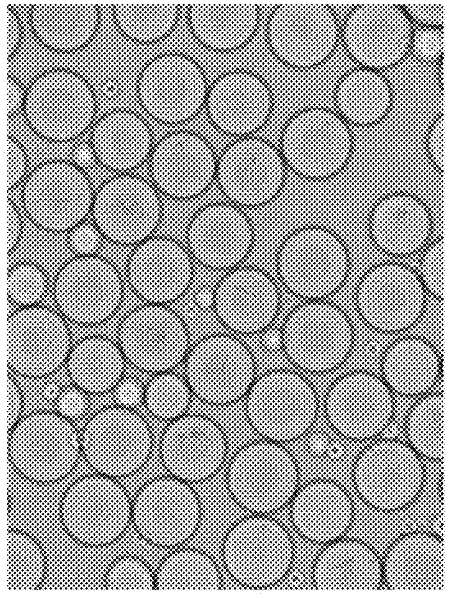
Figure 24A:
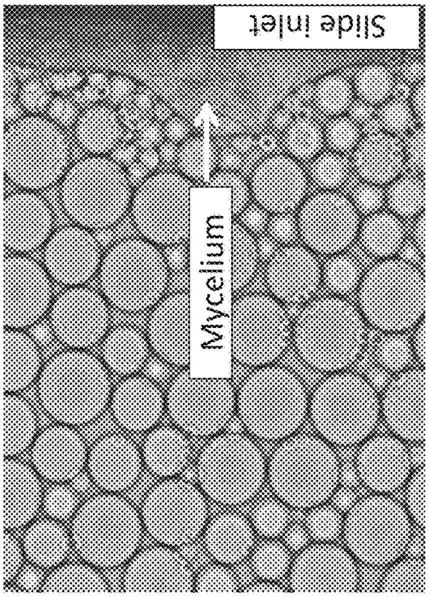
FIGS. 24A-24B illustrate inhibition of mold growth outside the aqueous phase when 100 mg/L dicloran is included in the oil phase of the water-in-oil droplets.
Figure 24B:
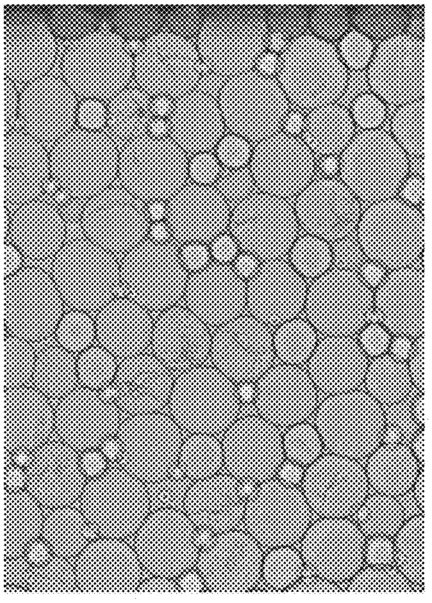
Figure 25A:
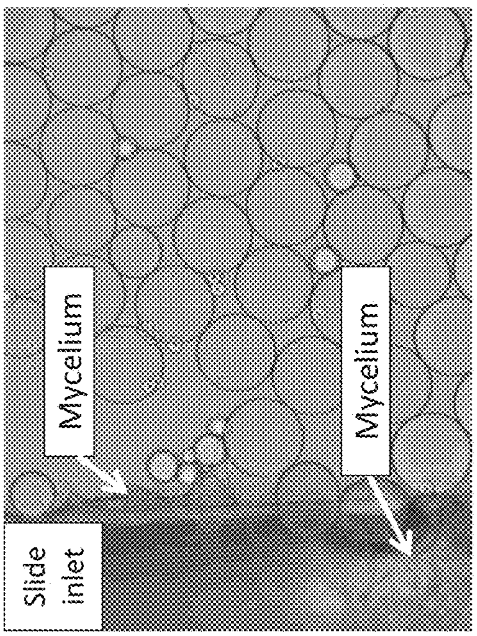
FIGS. 25A-25B illustrate inhibition of mold growth outside the aqueous phase when 80 mg/L dicloran is included in the oil phase of the water-in-oil droplets.
Figure 25B:
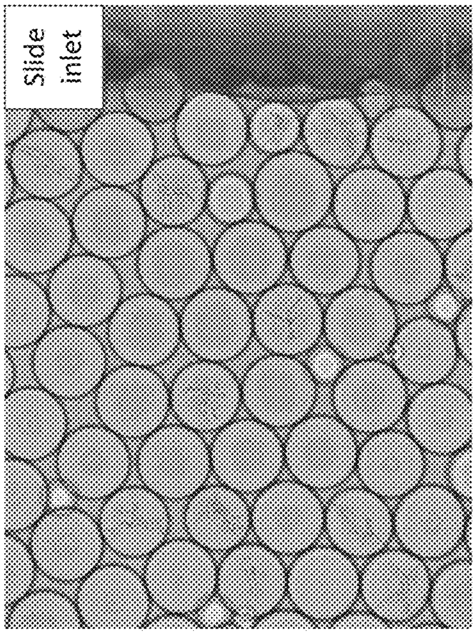
Figure 26A:
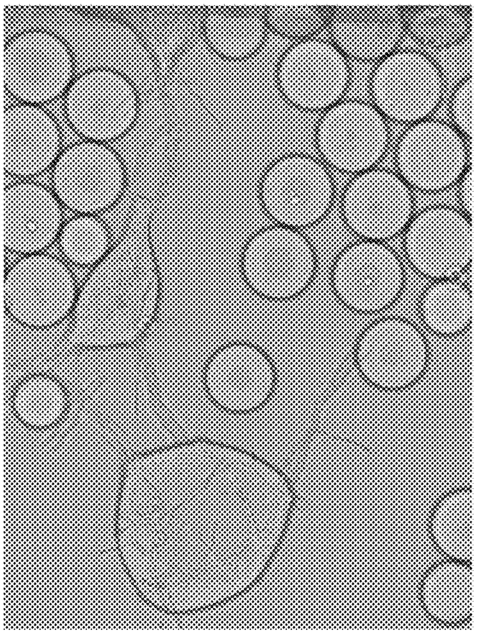
FIGS. 26A-26B illustrate inhibition of mold growth outside the aqueous phase when 60 mg/L dicloran is included in the oil phase of the water-in-oil droplets.
Figure 26B:
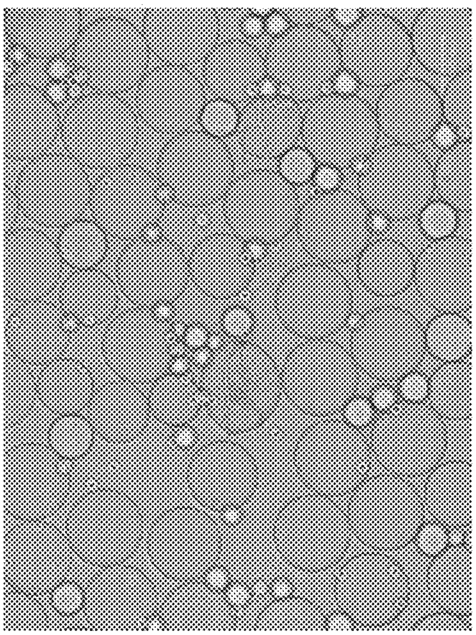
Figure 27A:
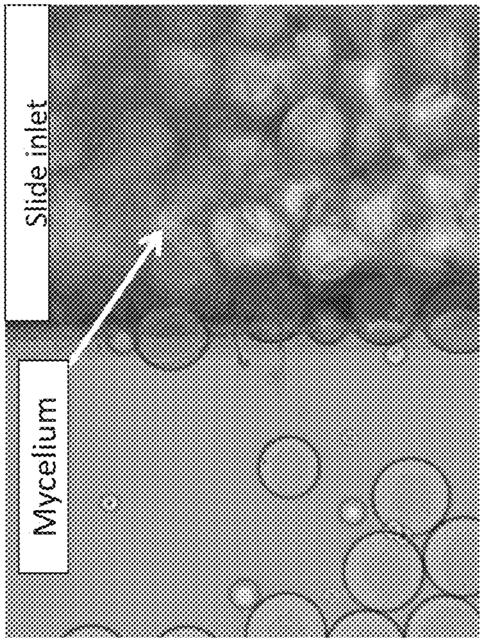
FIGS. 27A-27B illustrate inhibition of mold growth outside the aqueous phase when 80 mg/L dicloran is included in the oil phase of the water-in-oil droplets.
Figure 27B:
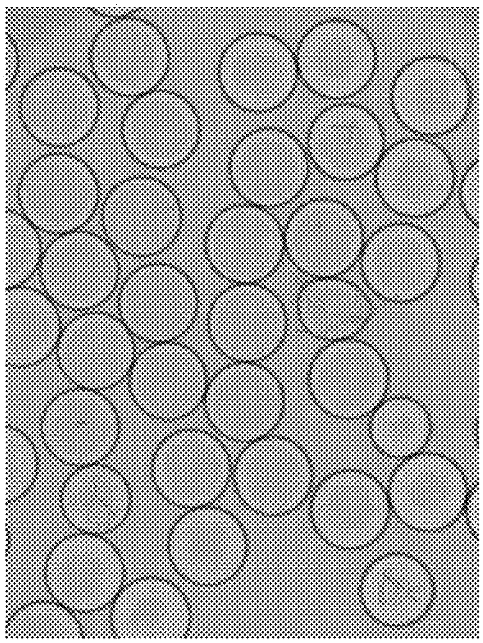

Results: In the absence of anti-fungal compound (control condition), mold hyphae were able to cross droplet membranes and to propagate through the sample, resulting in droplet coalescence (FIG. 20A). Further growth led to the sporulation of the strain and spores could be randomly observed in larger droplets (FIG. 20B). In some cases, strains produced mycelia that were responsible for clogging at the sample inlet of the observation slide.

Figure 28A:
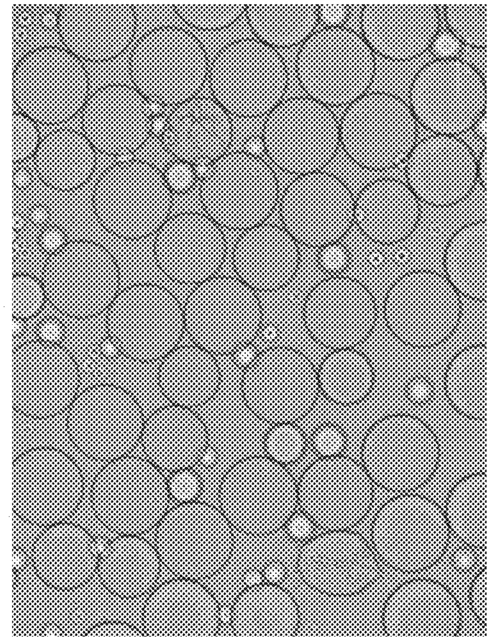
FIGS. 28A-28B illustrate inhibition of *Erotium rubrum* CECT 20807 growth outside the aqueous phase when 80 mg/L dicloran is included in the oil phase of the water-in-oil droplets. The fluorogenic substrate 5,6 carboxyfluorescein diacetate (25 mg/L) was added to the broth.
Figure 28B:
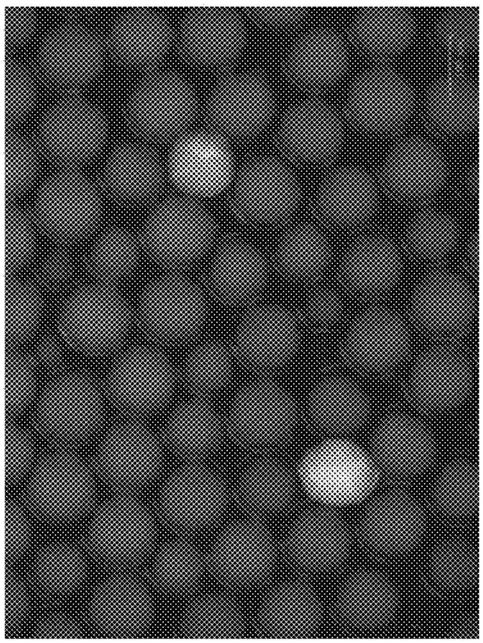
Figure 29A:
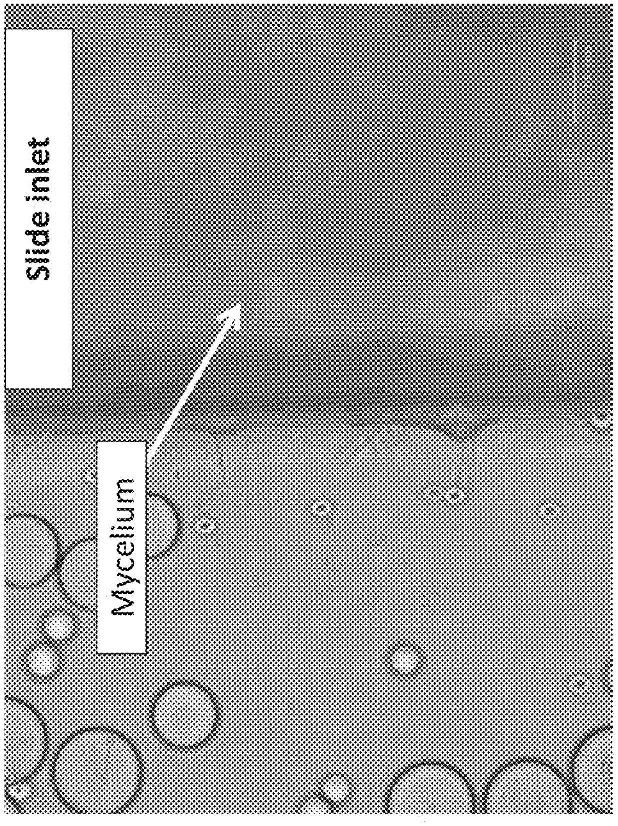
FIGS. 29A-29B illustrate inhibition of mold growth outside the aqueous phase when 100 mg/L dicloran is included in the oil phase of the water-in-oil droplets.
Figure 29B:
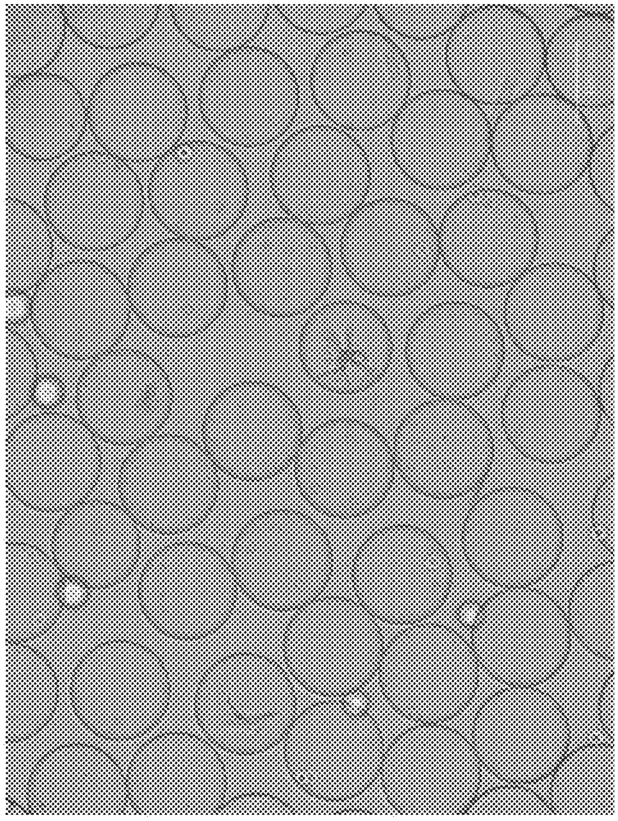

When dicloran was added to the oil for EvaGreen at concentrations ranging from 40 to 100 mg/L, the hyphae spreading was inhibited and mold growth was confined within the droplet. FIGS. 21A-29B show examples of the inhibition of the mold propagation by dicloran for several usual foodborne mold strains (e.g., *Fusarium graminearum* DSM 1096, *Mucor racemosus* CECT 20821, *Aspergillus restrictus* CECT 20807, *Penicillium hirsutum* ATCC 16025, and *Eurotium rubrum* CECT 20807). FIGS. 22 and 28 illustrate how the confinement of the hyphae in the droplet improved the detection of droplets positive for the mold when the fluorogenic substrate CFDA was added to the YGC broth. Note that because dicloran solution was prepared in acetone, the absence of inhibition of the strain by the acetone alone (0.5% v/v) was checked for each tested mold strain.

14. Inhibition of Mold Growth Outside the Droplet Aqueous Phase with Rose Bengal or Imazalil Goal: To determine if including an antifungal agent (e.g., rose bengal or imazalil) in the droplet oil phase inhibits mold growth outside the droplet aqueous phase.

Materials

| Reagent | Reference | Supplier | CAS number |
|---|---|---|---|
| Rose Bengal | 330000 | Sigma Aldrich | 632-69-9 |
| Ethanol 97% | | Sigma Aldrich | 64-17-5 |
| Imazalil (Enilconazole) | 32007 | Sigma Aldrich | 35554-44-0 |
| Acetone | 20066.31 | VWR | 67-64-1 |
| YGC broth | 3555489 | Bio-Rad | N/A |
| Yeast extract | 5 g/L | | |
| Glucose | 20 g/L | | |
| Chloramphenicol | 0.3 g/L | | |

| Mold strain |
|---|
| *Aspergilluis restrictus* CECT 20807 |
| *Penicillium hirsutum* ATCC 16025 |

| Droplet generation component | Reference | Supplier |
|---|---|---|
| Oil for Eva Green | 186-4006 | Bio-Rad |
| Pluronic F68 surfactant 10% | — | DBG |
| DG8 cartridge | 186-4008 | Bio-Rad |
| DG8 gasket | 186-3009 | Bio-Rad |
| TC20 counting slide | 1450011 | Bio-Rad |

Methods

Rose bengal was dissolved in ethanol and added to the Oil for Eva Green at the concentration of 150 mg/L. The final concentration of ethanol in the oil phase was of 0,5% (v/v).

Imazalil was prepared in acetone and added to the Oil for Eva Green at the concentration of 0.5 mg/L. The final concentration of acetone in the oil phase was of 0.1% (v/v).

Spore suspensions were encapsulated at the concentration of 105 spores/mL in the YGC broth to reach the ratio of 1 positive droplet (containing 1 cell) out of 10.

Droplet emulsions were prepared with Oil for Eva Green supplemented with the appropriate fungicide.

The droplets were then transferred at 28° C. for 24-48 hours.

After incubation, droplet samples were observed under the ZOE™ fluorescent Cell Imager.

Note that the absence of an effect of ethanol on the growth of the strains used to test rose bengal was checked as was the absence of an effect of acetone on the growth of the strains used to test imazalil.

Figure 30A:
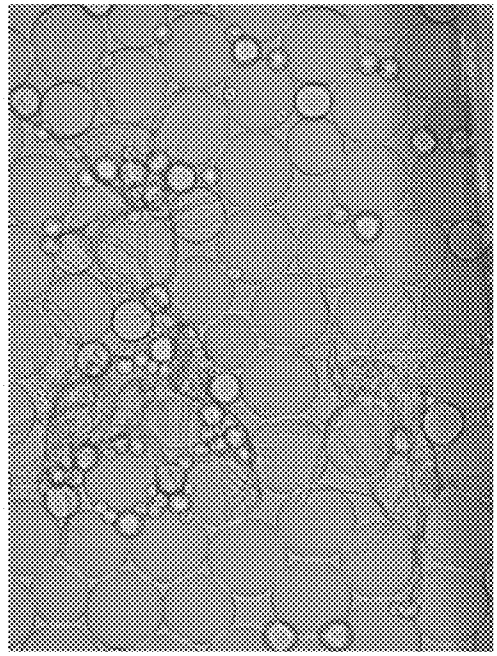
FIGS. 30A-30B illustrate inhibition of mold growth outside the aqueous phase when 150 mg/L rose bengal is included in the oil phase of the water-in-oil droplets.
Figure 30B:
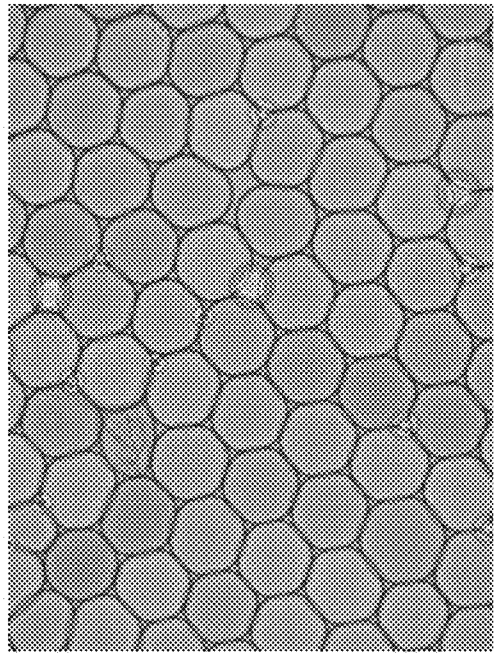
Figure 31A:
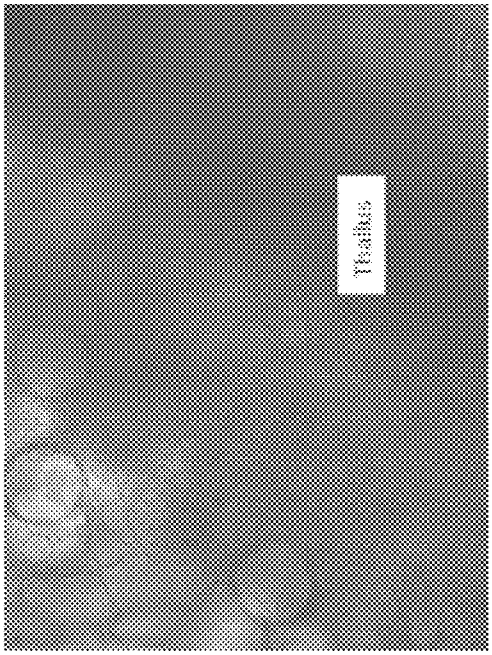
FIGS. 31A-31B illustrate inhibition of mold growth outside the aqueous phase when 0.5 mg/L Imazalil is included in the oil phase of the water-in-oil droplets.
Figure 31B:
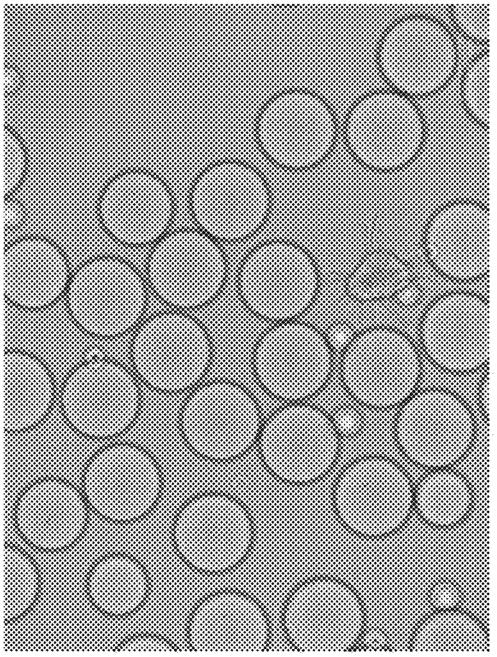

Results: In the absence of anti-fungal compound (control condition), mold hyphae were able to cross droplet membranes and to propagate through the sample, resulting in droplet coalescence (FIGS. 30A and 31A). When 150 mg/L rose bengal (FIG. 30B) or 0.5 mg/L Imazalil (FIG. 31B) was added to the oil for EvaGreen, the hyphae spreading was inhibited and mold growth was confined within the droplet.

15. Detection of Microorganisms Using a Lectin as a Marker

A solution of 5 mg/mL of fluorescein-labeled ConcanavalinA ("ConA" from Thermofisher) in sodium bicarbonate was diluted in TCS broth (Bio-Rad Laboratories) or RPMI previously spiked with strains (at 1 McFarland for yeasts and 0.5McFarland for bacteria) belonging to the following species: *Candida albicans, C. parapsilosis, C. tropicalis, C. krusei, C. glabrata, Cryptococcus neoformans, Bacillus subtilis, E. coli, S. aureus.* 20 μL of this mix were used to prepare droplets that were read using the ZOE™ Fluorescent Cell Imager (Bio-Rad Laboratories) without any incubation time.

Figure 33:
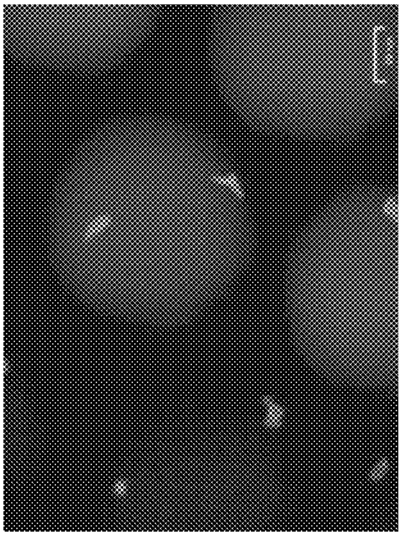
FIGS. 32-35 illustrate the use of lectin for detection of microorganisms.
Figure 32:
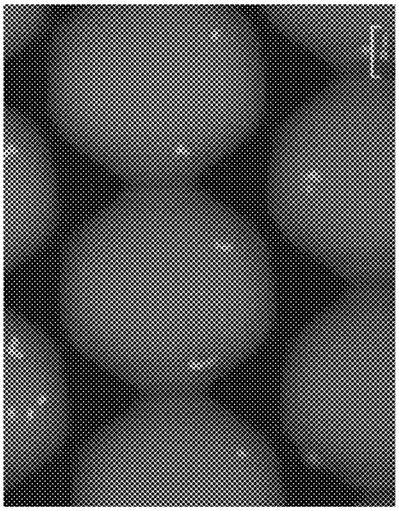
Figure 34:
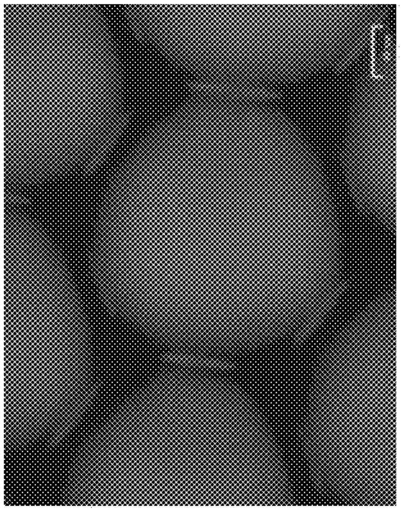

The results (FIGS. 32, 33, and 34 for *C. glabrata, C. tropicalis*, and *E Coli*, respectively) and the table below showed that *Candida* (i.e., *C. albicans, C. parapsilosis, C. tropicalis, C. krusei, C. glabrata*) can be directly and specifically detected, whereas bacteria such as *E. coli* did not fluoresce and cannot be detected.

| | fluorescence | |
|---|---|---|
| | yes | no |
| *C. albicans* | x | |
| *C. tropicalis* | x | |
| *C. glabrata* | x | |
| *C. krusei* | x | |
| *C. neoformans* | | x (very faint) |
| *B. subtilis* | | X |
| *E. coli* | | X |
| *S. aureus* | | X |

Figure 35:
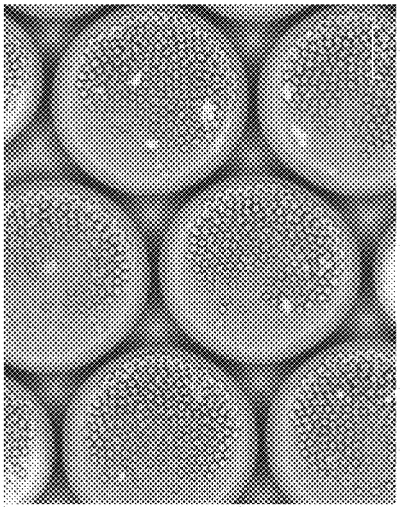

In another assay using *C. krusei*, up to 10% of blood was added before the droplet making step. The samples were read using the ZOE™ Fluorescent Cell Imager (Bio-Rad Laboratories) at $T_0$. FIG. 35 is a merged image of a visible image and a green fluorescence image from the sample. In FIG. 35, the red blood cells were grey and the *Candida krusei* cells were green fluorescent. The results demonstrate that ConA can be used to specifically detect the presence of *Candida* species in a sample even though it contains 10% of blood.

16. Droplet Gelation

Goal: To determine if including a gelling agent prevents a reduction in the droplet size as yeast strains are grown in the droplets.

Materials

| Reagent | Reference | Supplier | CAS number |
|---|---|---|---|
| YGC broth | 3555489 | Bio-Rad | N/A |
| Yeast extract | 5 g/L | | |
| Glucose | 20 g/L | | |
| Chloramphenicol | 0.3 g/L | | |
| Sodium alginate (viscosity 100-300 cP) | A2158 | Sigma | 9005-38-3 |
| Calcium Carbonate ($CaCO_3$) | 500016 | Merck | 471-34-2 |
| Oil for Eva Green | 186-4006 | Bio-Rad | N/A |
| Acetic acid | 500005 | MR | 64-19-7 |

| Strain | Characteristic |
|---|---|
| *Candida albicans* ATCC 10231 | Fermentative strain (broth acidification) |
| *Saccharomyces cerevisiae* DSM 1333 | Fermentative strain (broth acidification) |
| *Debagomyces hansenii* CLIB 197 | Weakly fermentative strain |

| Droplet generation component | Reference | Supplier |
|---|---|---|
| Oil for Eva Green | 186-4006 | Bio-Rad |
| Pluronic F68 surfactant 10% | — | DBG |
| DG8 cartridge | 186-4008 | Bio-Rad |
| DG8 gasket | 186-3009 | Bio-Rad |
| TC20 counting slide | 1450011 | Bio-Rad |

Methods

Sterile YGC broth supplemented with calcium carbonate (0, 0.5 or 1 g/L) and sodium alginate (0, 2.5 or 3.5 g/L) was used as the culture medium.

Cells of *Candida albicans* ATCC 10231, *Saccharomyces cerevisiae* DSM 1333 and Debaryomyces *hansenii* CLIB 197 were encapsulated in order to observe the effective gelation of the droplets.

Droplets were generated with oil for Eva Green containing 0.1% (v/v) of acetic acid unless otherwise indicated.

Droplet emulsions were incubated for 22-48 hours at 28° C. and observed with a ZOE™ Cell Imager.

Figure 36B:
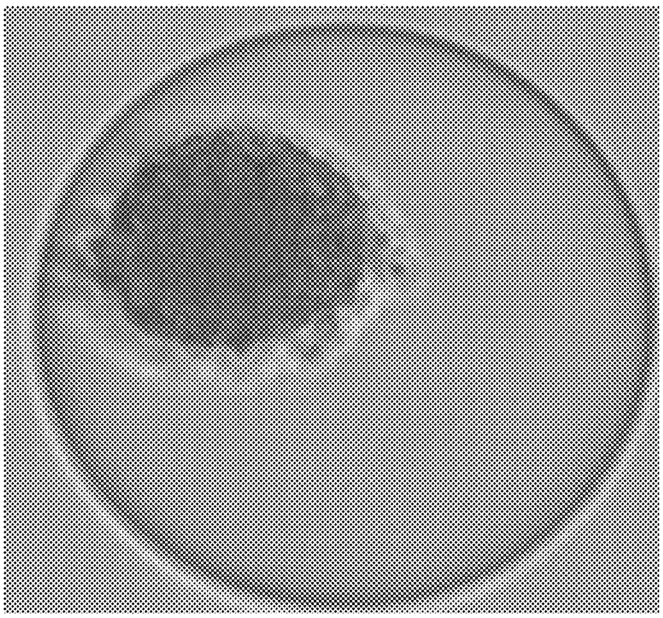
FIGS. 36A and 36B illustrate growth of *Candida albicans* ATCC 10231 in a non-gelled droplet (FIG. 36A) and a gelled droplet (FIG. 36B).
Figure 36A:
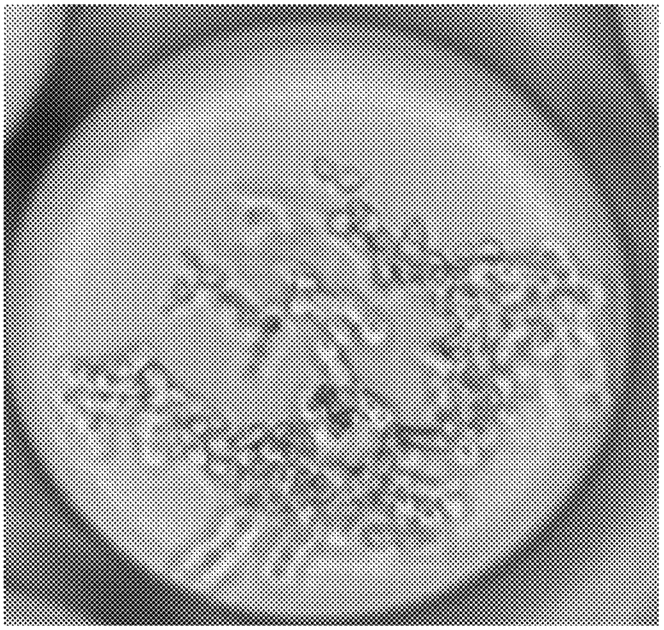

Results: FIGS. 36A-42D illustrate the droplet gelation results. FIGS. 36A and 36B show growth of *Candida albicans* ATCC 10231 in a non-gelled (FIG. 36A) and a gelled (FIG. 36B) droplet after 22 hours of incubation. Gelation was obtained by supplementing the YGC culture broth with 3.5 g/L of sodium alginate and 1 g/L of calcium carbonate. The gelled droplets showed no modification of shape. Gelation was only visible with cell growth. Cells showed movement and scattered in the non-gelled droplets. Cells looked embedded and grew as microcolonies in the gelled droplets.

To ensure that the presence of sodium alginate or calcium carbonate alone does not cause gelation, sodium alginate and calcium carbonate were tested separately in a control assay with *Candida albicans* ATCC 10231 (FIGS. 37A-37D) or *Saccharomyces cerevisiae* DSM 1333 (FIGS. 38A-38D). FIGS. 37A-37D and FIGS. 38A-38D show growth of the microorganisms in droplets after 24 hours of incubation. Growth of the microorganisms was in (A) YGC broth; (B)

Figure 37A:
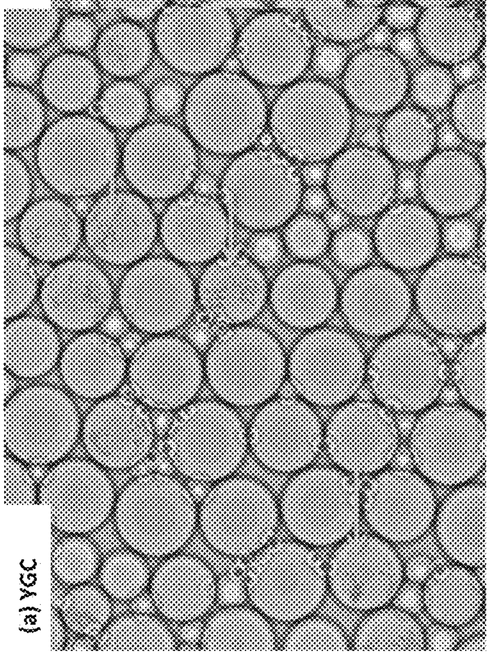
FIGS. 37A-37D illustrate control conditions to ensure that gelation was not due to the presence of gelling agent alone. The droplets contained *Candida albicans* ATCC 10231 in YGC broth in the aqueous phase and 0.1% (v/v) acetic acid in the oil phase. Arrows show examples of droplets positive for *Candida albicans.*
Figure 37B:
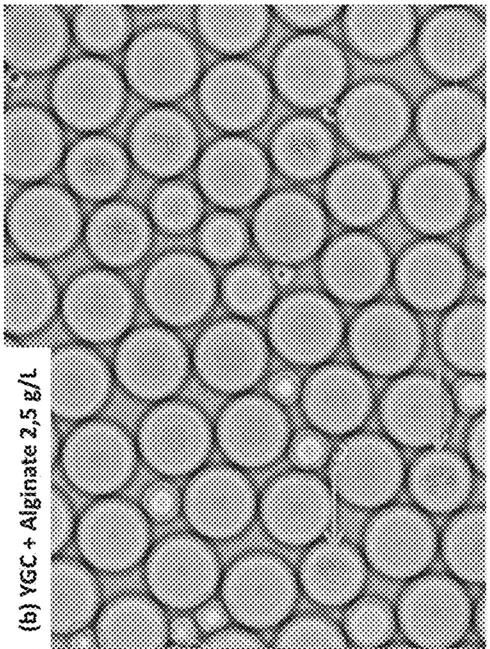
Figure 37C:
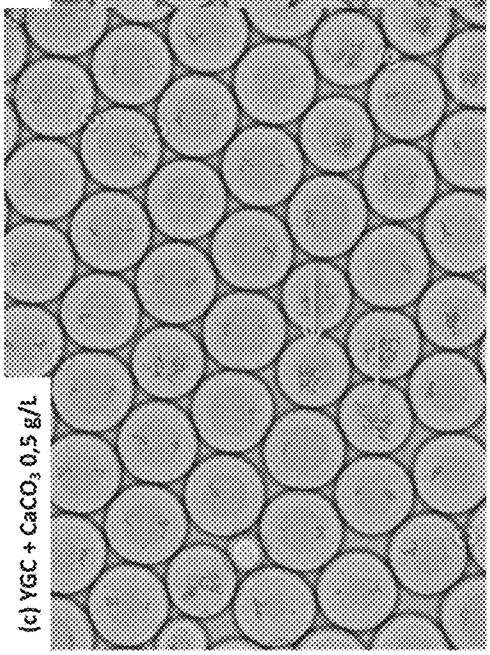
Figure 37D:
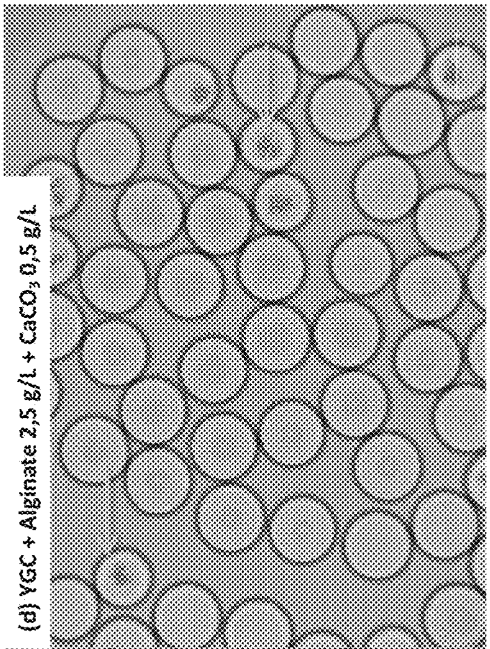
Figure 38A:
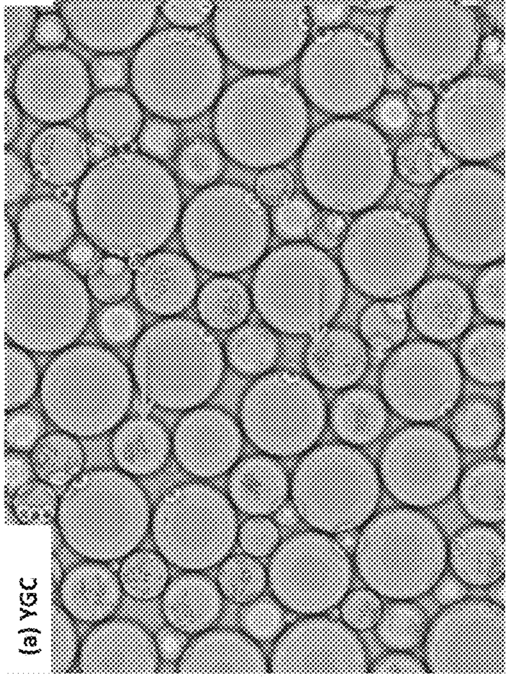
FIGS. 38A-38D illustrate control conditions to ensure that gelation was not due to the presence of gelling agent alone. The droplets contained *Saccharomyces cerecisiae* DSM 1333 in YGC broth in the aqueous phase and 0.1% (v/v) acetic acid in the oil phase. Arrows show examples of droplets positive for *Saccharomyces cerecisiae.*
Figure 38B:
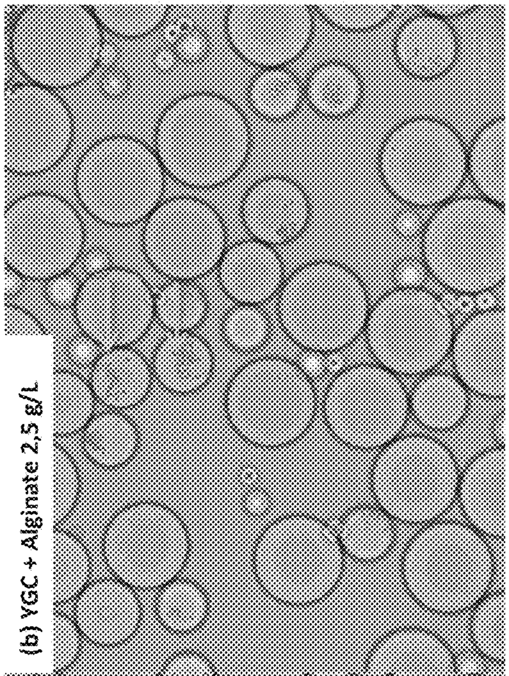
Figure 38C:
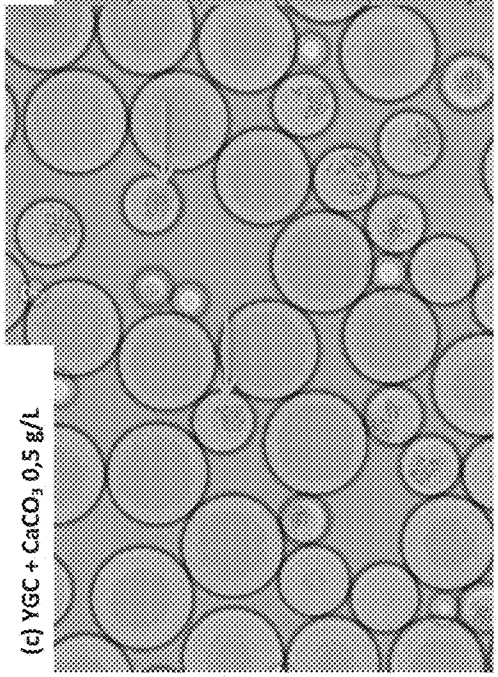
Figure 38D:
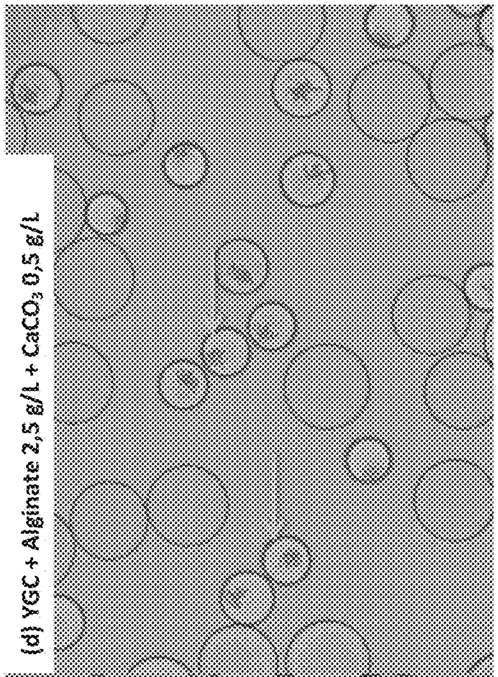

YGC supplemented with 2.5 g/L alginate; (C) YGC supplemented with 0.5 g/L calcium carbonate; or (D) YGC supplemented with 2.5 g/L alginate and 0.5 g/L calcium carbonate. Gelation of the droplets occurred only when sodium alginate and calcium carbonate were present simultaneously, as shown by the formation of micro-colonies in the positive droplets (FIGS. 37D and 38D). In the other assays (FIGS. 37A-37C and 38A-38C), the cells were motile and spread. Arrows show examples of positive droplets.

Figure 39A:
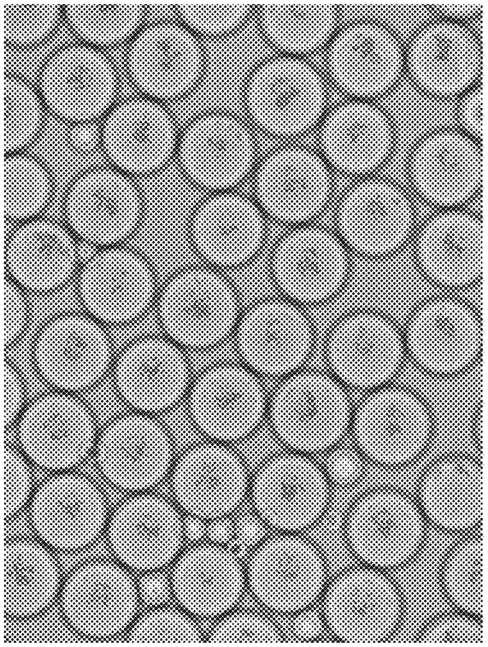
FIGS. 39A-39C and FIGS. 40A-40C illustrate gelation in the presence of acidifying yeast strain *Saccharomyces cerecisiae* DSM 1333 (FIGS. 39B and 40B) and non-acidifying yeast strain Debaryomyces *hansenii* CLIB 197 (FIGS. 39C and 40C). The strains were grown for 24 hours in YGC broth supplemented with 1 g/L calcium carbonate. No acetic acid was added to the oil.
Figure 39C:
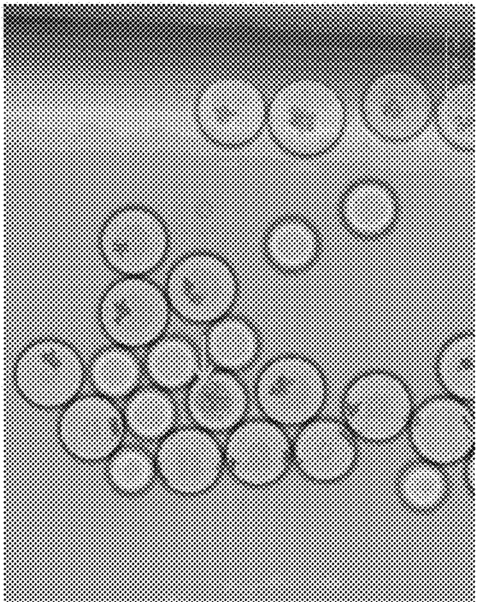
Figure 39B:
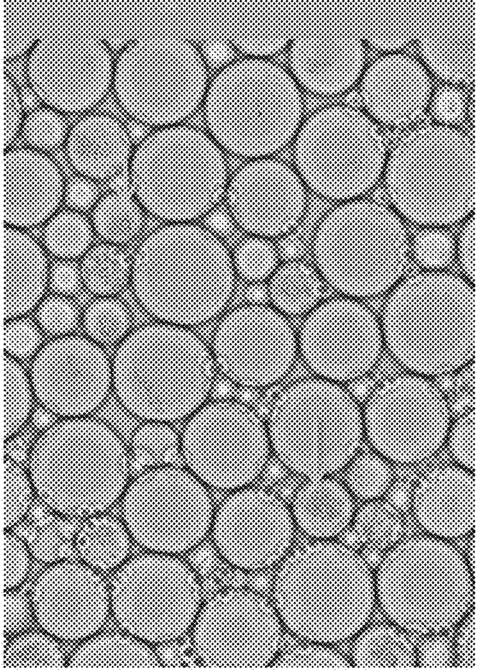
Figure 40A:
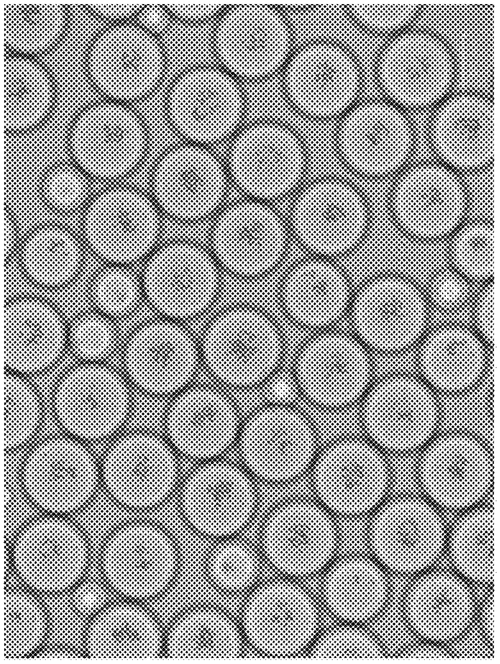
Figure 40C:
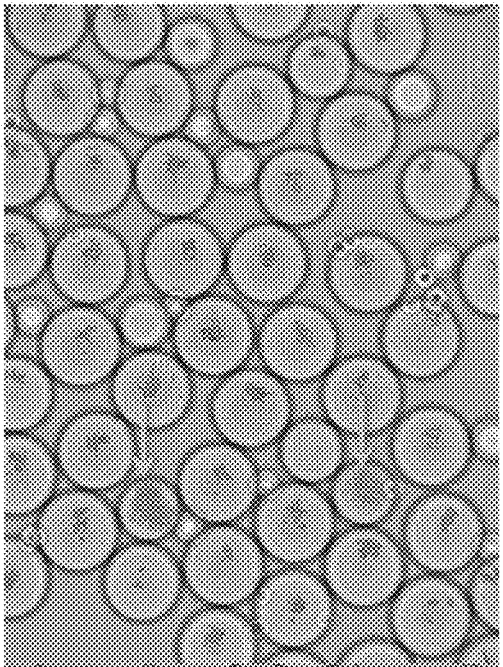
Figure 40B:
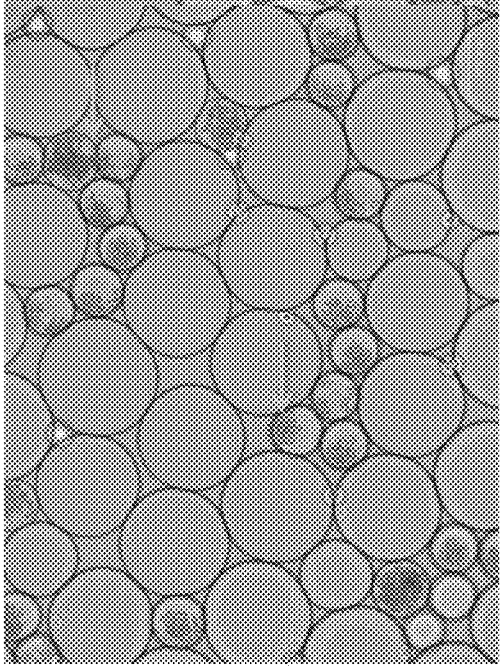

FIGS. 39A-39C and 40A-40C show the results of experiments using acidifying and non-acidifying yeast strains and with no acetic acid added to the oil phase. FIGS. 39A and 40A are negative controls. *Saccharomyces cerevisiae* DSM 1333 (FIGS. 39B and 40B) or Debaryomyces *hansenii* CLIB 197 (FIGS. 39C and 40C) were grown in YGC broth supplemented with 1 g/L calcium carbonate after 24 hours of incubation. The calcium carbonate was partially dissociated in the presence of acidifying *Saccharomyces* strain only. With the non-acidifying Debaryomyces strain, the particles of calcium carbonate were observed as in the negative control. Arrows show examples of positive droplets.

Figure 41A:
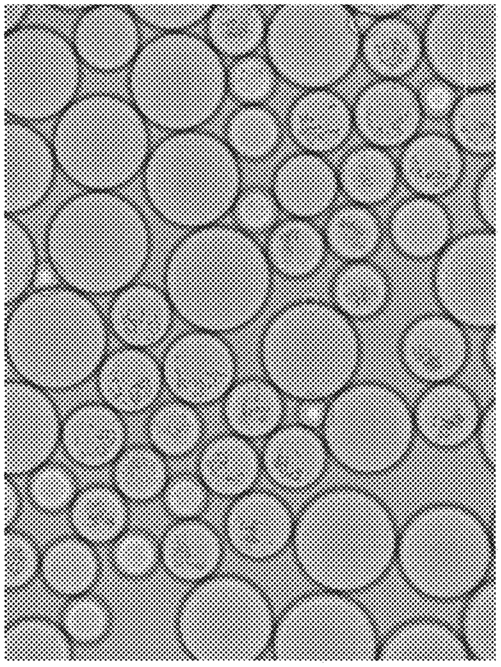
FIGS. 41A-41D illustrate gelation in the absence (FIGS. 41A and 41C) and presence (FIGS. 41B and 41D) of acetic acid after droplets containing *Saccharomyces cerecisiae* DSM 1333 were incubated 24 hours.
Figure 41B:
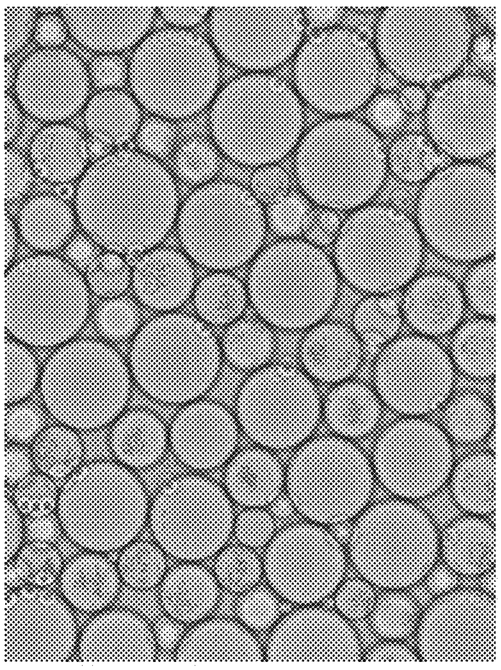
Figure 41C:
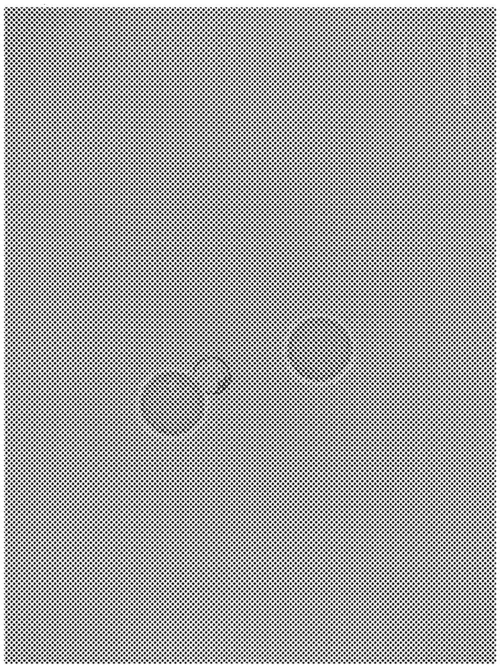
Figure 41D:
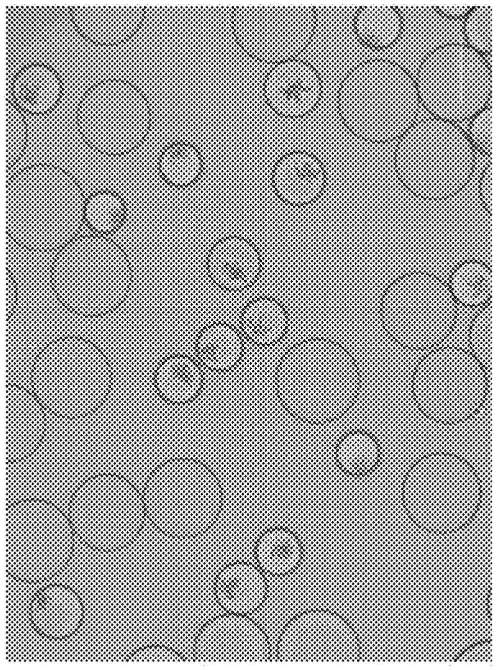

FIGS. 41A-41D show the results of a gelation experiment in the absence (FIGS. 41A and 41C) and presence (FIGS. 41B and 41D) of acetic acid after droplets containing *Saccharomyces cerecisiae* DSM 1333 were incubated 24 hours. In FIGS. 41A and 41B, the *Saccharomyces* strain was grown in YGC broth only. In FIGS. 41C and 41B, the *Saccharomyces* strain was grown in YGC broth supplemented with 2.5 g/L alginate and 0.5 g/L calcium carbonate. Gelation occurred in the presence or absence of acetic acid.

Figure 42A:
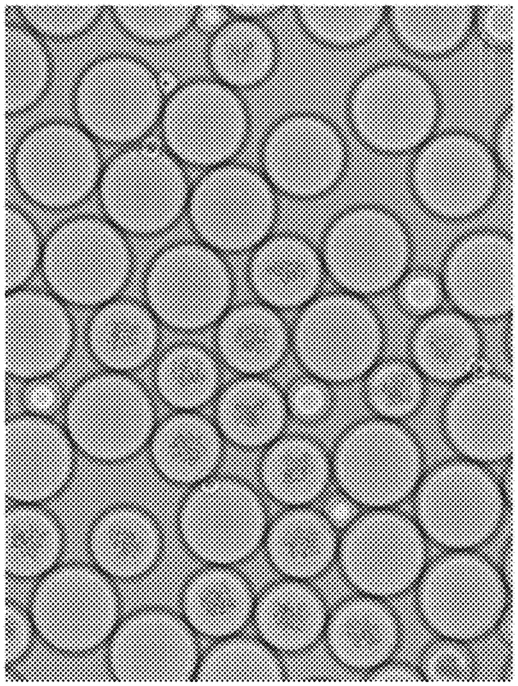
FIGS. 42A-42D illustrate gelation in the absence (FIGS. 42A and 42C) and presence (FIGS. 42B and 42D) of acetic acid after droplets containing *Candida albicans* ATCC 10231 were incubated 48 hours.
Figure 42B:
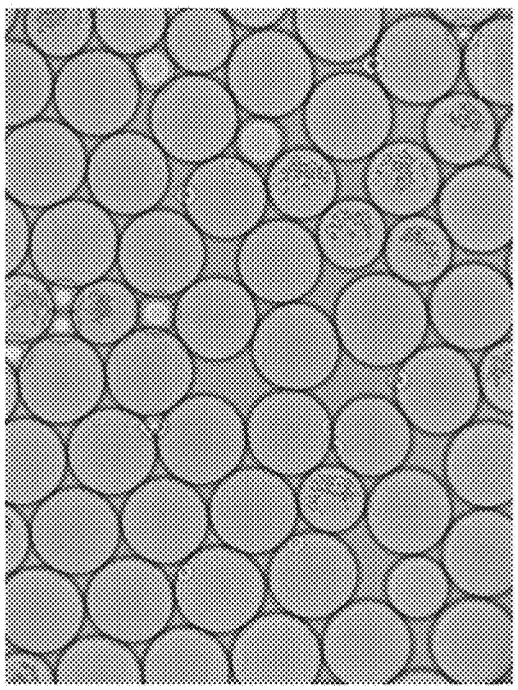
Figure 42C:
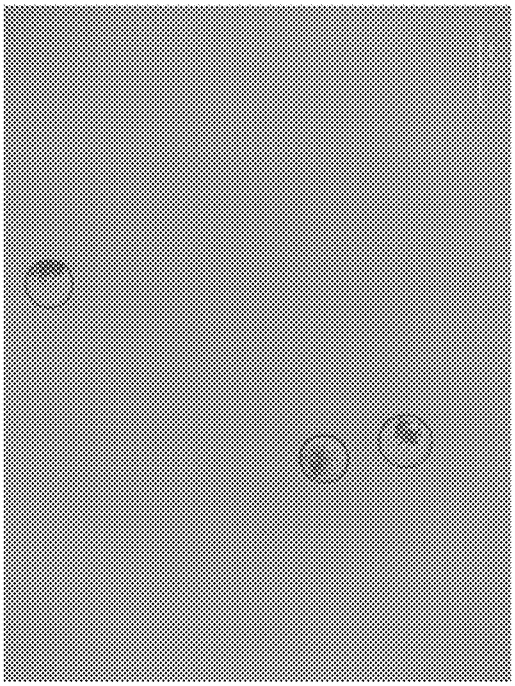
Figure 42D:
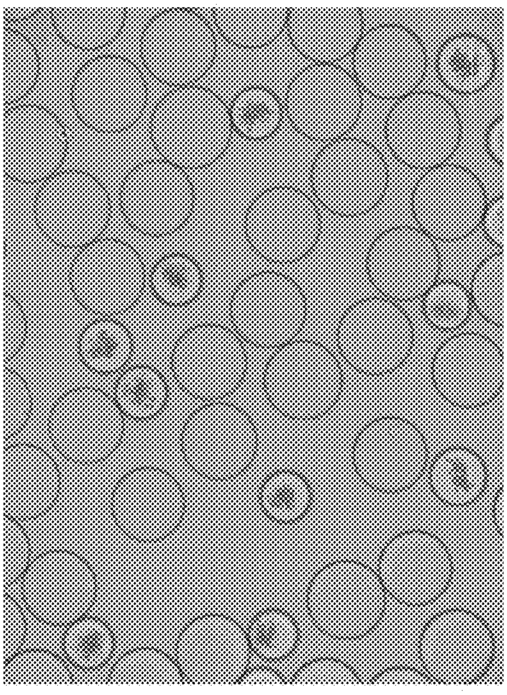

FIGS. 42A-42D show the results of a gelation experiment in the absence (FIGS. 42A and 42C) and presence (FIGS. 42B and 42D) of acetic acid after droplets containing *Candida albicans* ATCC 10231 were incubated 24 hours. In FIGS. 42A and 42B, the *Candida* strain was grown in YGC broth only. In FIGS. 42C and 42B, the *Candida* strain was grown in YGC broth supplemented with 2.5 g/L alginate and 0.5 g/L calcium carbonate. Gelation occurred in the presence or absence of acetic acid.

The results demonstrate that a gelling agent can prevent a reduction in droplet size when yeast is grown in the droplets. The results also show that acetic acid is not required in the oil phase when acidifying yeast strains are grown in YGC broth supplemented with alginate and calcium carbonate.

17. Use of an Esterase Substrate or a Phosphatase Substrate for Detection of Various Strains of Yeast and Mold Materials

| Reagent | Reference | Supplier | CAS number |
|---|---|---|---|
| YGC broth | 3555489 | Bio-Rad | NA |
| Yeast extract | 5 g/L | | |
| Glucose | 20 g/L | | |
| Chloramphenicol | 0.3 g/L | | |
| CFDA = Esterase substrate | | | |
| 5(6)-carboxyfluorescein diacetate | 21879 | Sigma Aldrich | 124387-19-5 |
| λExc max = 492 nm | | | |
| λEm max = 517 nm | | | |
| ALDOL ® 515 Phosphate = Phosphatase substrate | | | |
| λExc max = 500 nm | A-4721 | Biosynth | — |
| λEm max = 610 nm | | | |
| DMSO | 2384.297 | VWR | 67-68-5 |

Figure 43B:
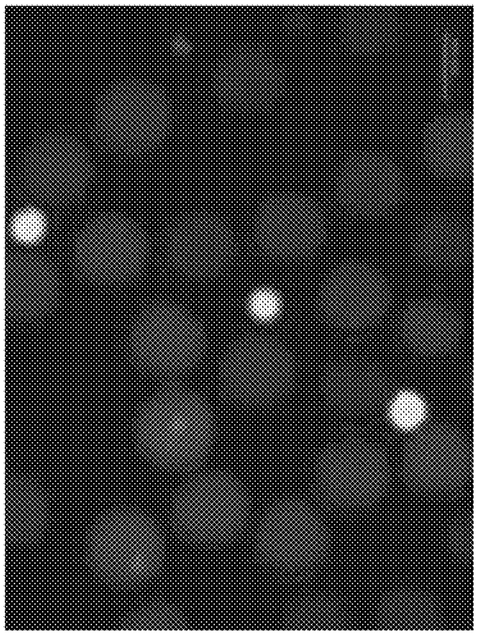
Figure 44B:
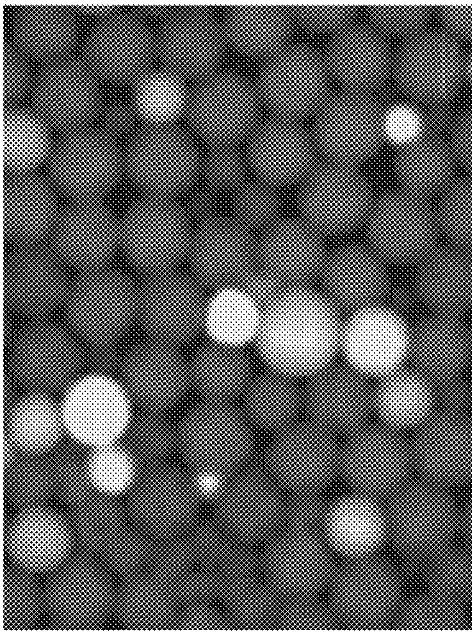
FIGS. 44A and 44B show detection of *Kluyveromyces lactis* CLIB 196 in the absence and presence, respectively, of CFDA.
Figure 43A:
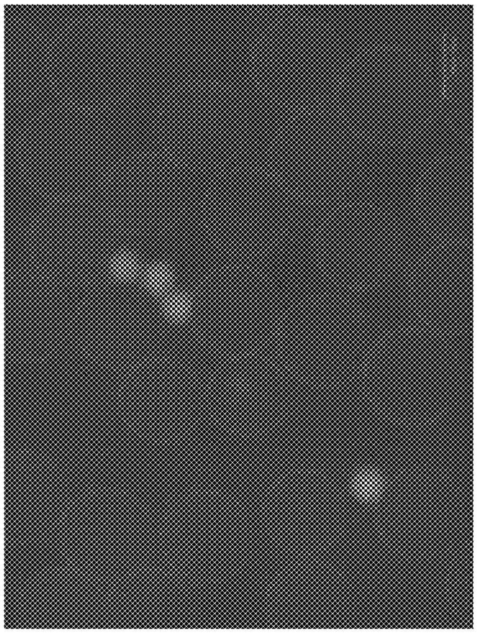
Figure 44A:
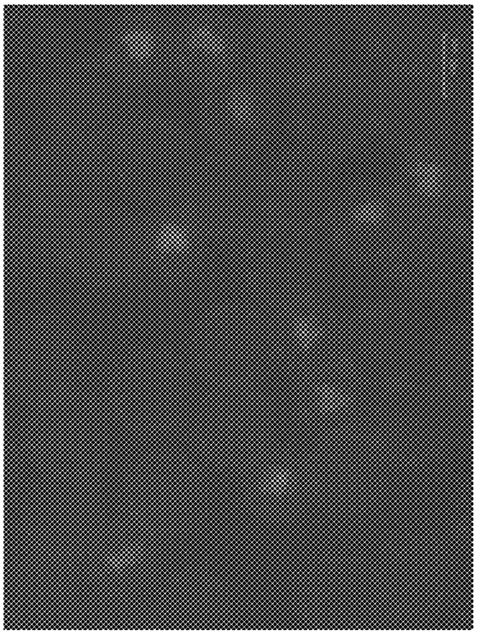
Figure 45B:
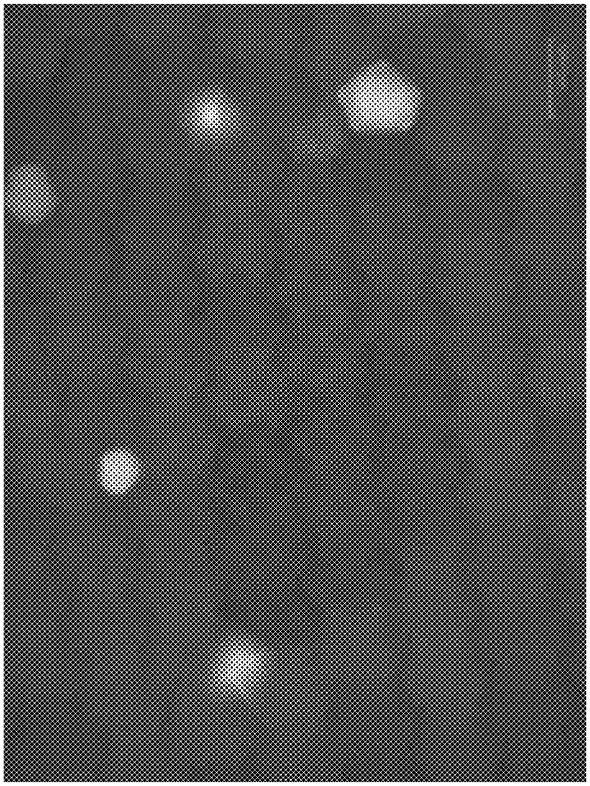
Figure 45A:
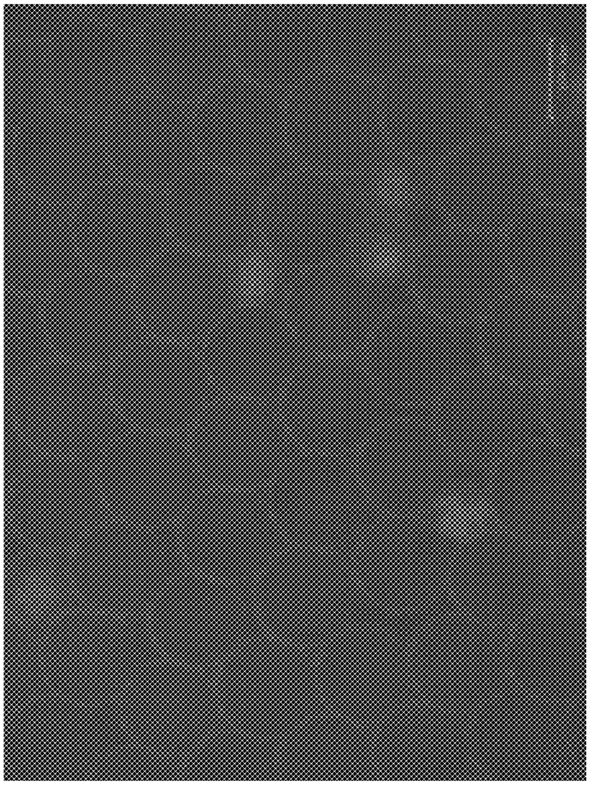
Figure 46B:
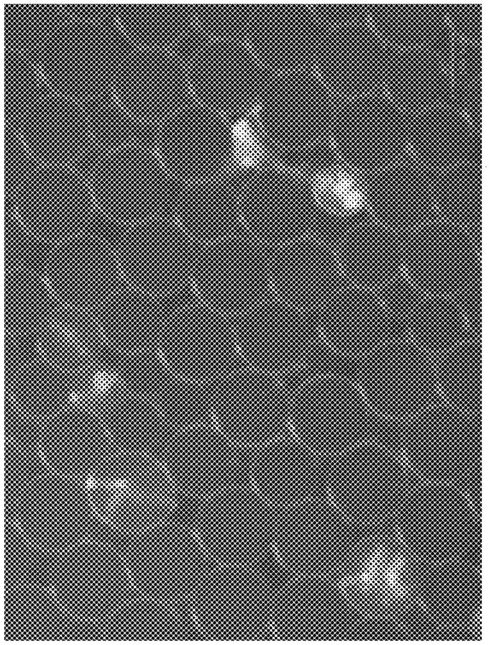
FIGS. 46A-46D illustrate the specific detection and/or enumeration of *Mucor racemosus* CECT 20821 in the absence (FIGS. 46A and 46B) and presence (FIGS. 46C and 46D), respectively, of 25 mg/L CFDA after 48 hours of incubation in YGC broth. Dicloran was added to the oil phase to confine the growth of the hyphae in the aqueous phase.
Figure 46D:
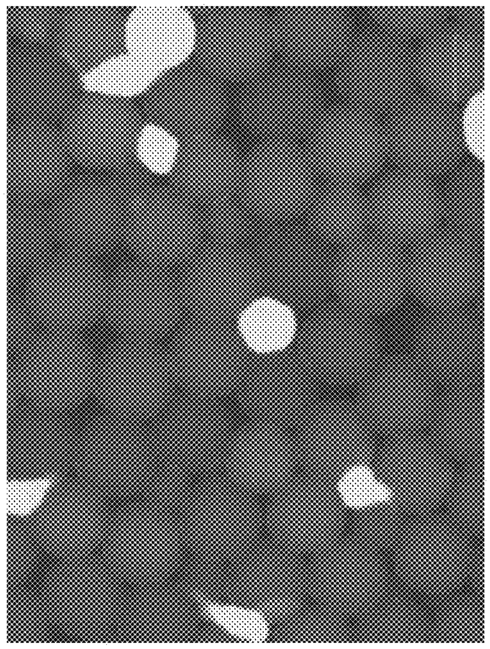
Figure 46A:
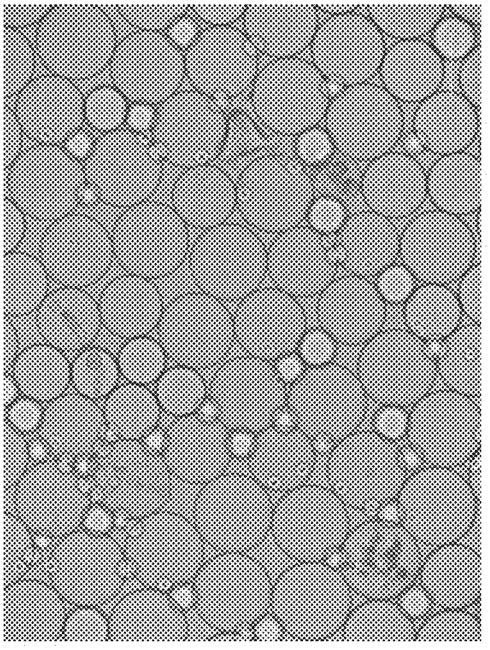
Figure 46C:
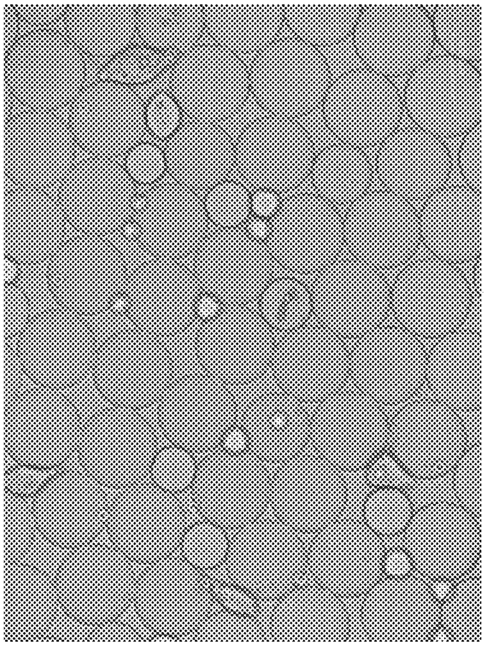
Figure 47A:
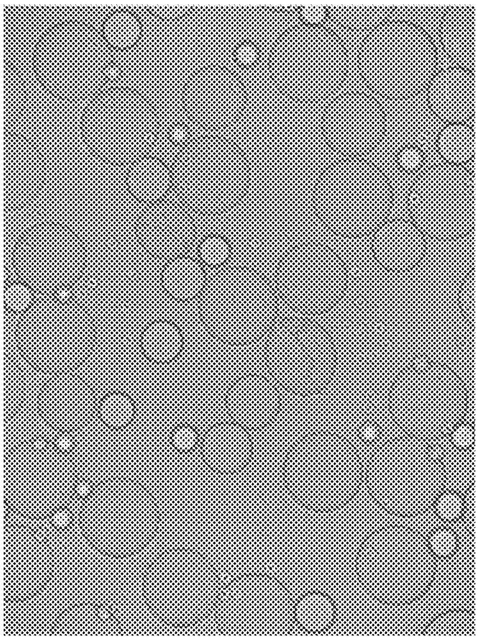
FIGS. 47A-47D illustrate the specific detection and/or enumeration of *Eurotium rubrum* CECT 20808 in the absence (FIGS. 47A and 47B) and presence (FIGS. 47C and 47D), respectively, of 25 mg/L CFDA after 24 hours of incubation in YGC broth. Dicloran was added to the oil phase to confine the growth of the hyphae in the aqueous phase.
Figure 47B:
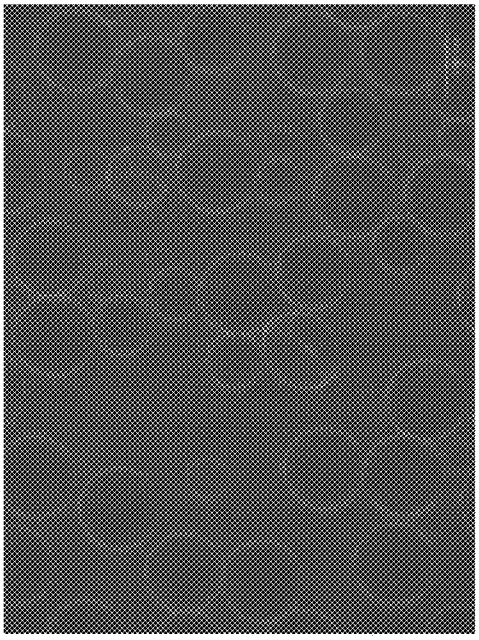
Figure 47C:
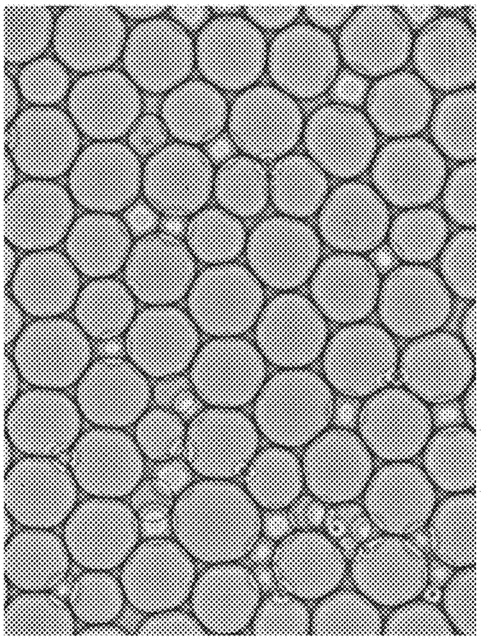
Figure 47D:
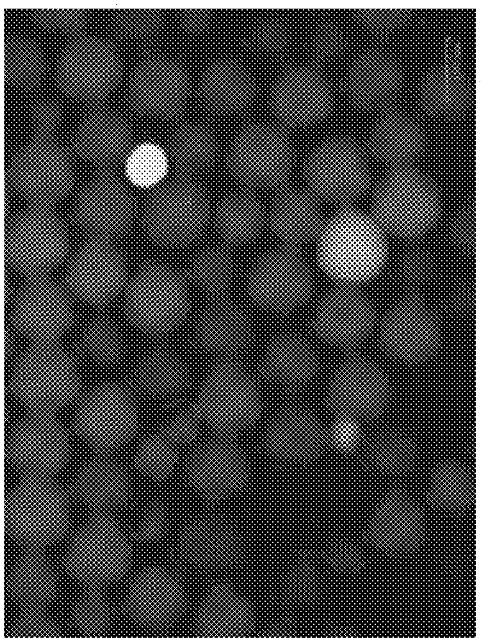
Figure 48A:
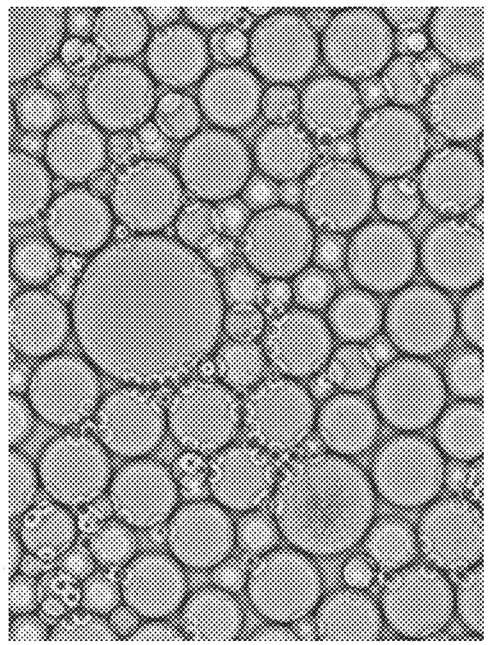
FIGS. 48A-48D illustrate the specific detection and/or enumeration of *Fusarium graminearum* DSM 1096 in the absence (FIGS. 48A and 48B) and presence (FIGS. 48C and 48D), respectively, of 25 mg/L CFDA after 48 hours of incubation in YGC broth. Dicloran was added to the oil phase to confine the growth of the hyphae in the aqueous phase.
Figure 48B:
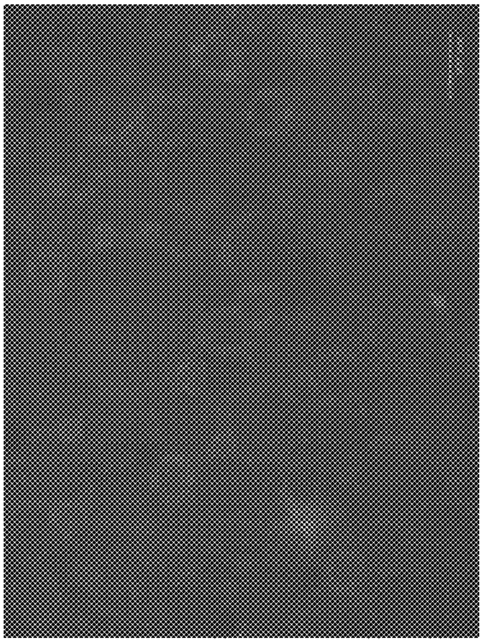
Figure 48C:
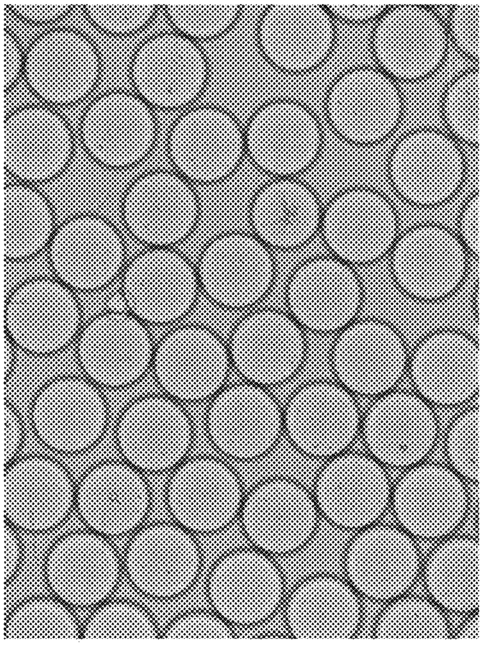
Figure 48D:
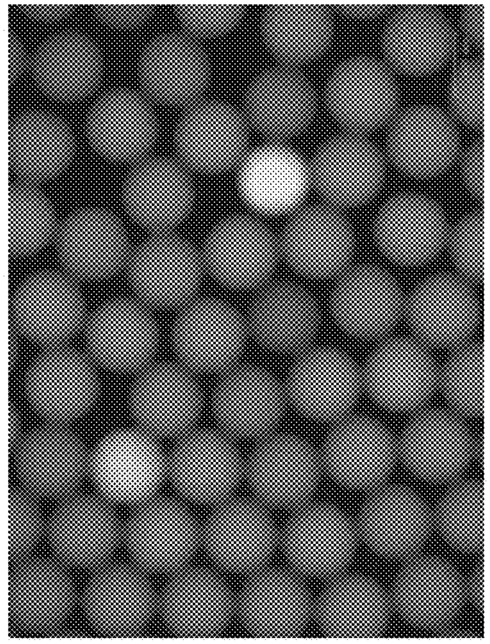
Figure 49B:
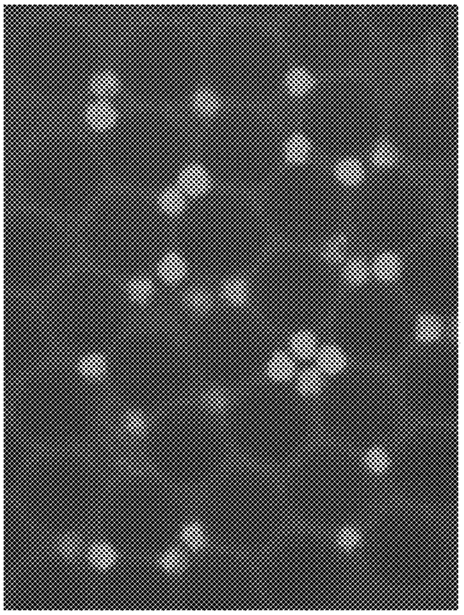
FIGS. 49A and 49B illustrate the specific detection and/or enumeration of *Candida tropicalis* ATCC 750 in the absence (FIG. 49A) and presence (FIG. 49B), respectively, of 50 mg/L ALDOL® 515 Phosphate after 24 hours of incubation in YGC broth.
Figure 50B:
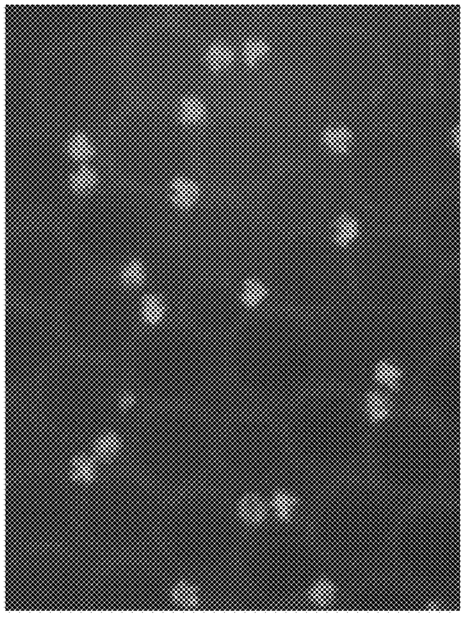
FIGS. 50A and 50B illustrate the specific detection and/or enumeration of *Saccharomyces cerevisiae* DSM 1333 in the absence (FIG. 50A) and presence (FIG. 50B), respectively, of 50 mg/L ALDOL® 515 Phosphate after 24 hours of incubation in YGC broth.
Figure 49A:
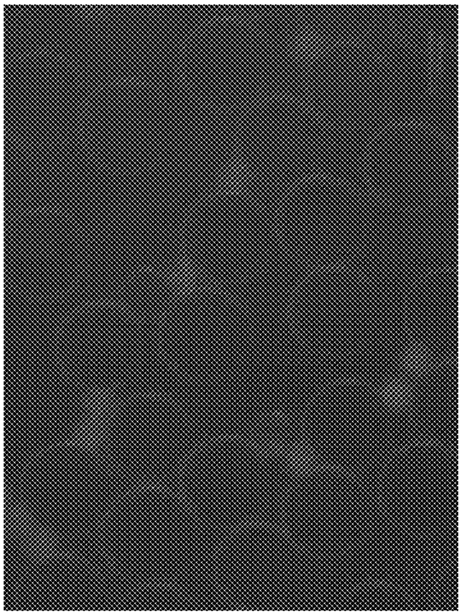
Figure 50A:
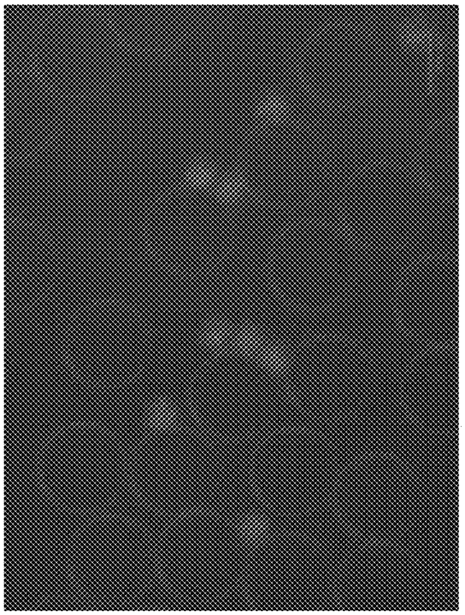
Figure 51B:
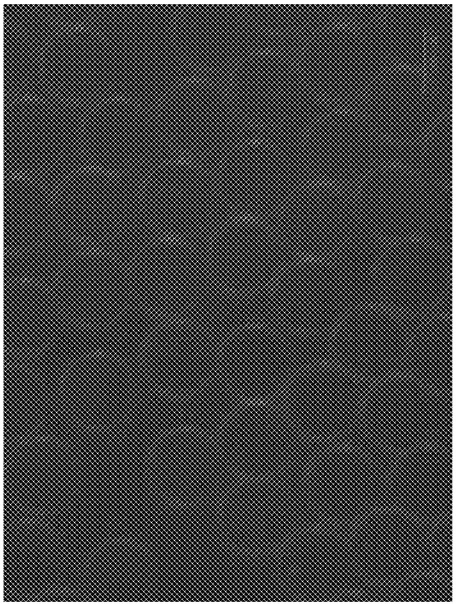
FIGS. 51A-51D illustrate the specific detection and/or enumeration of *Fusarium graminearum* DSM 1096 in the absence (FIGS. 51A and 51B) and presence (FIGS. 51C and 51D), respectively, of 25 mg/L ALDOL® 515 Phosphate after 24 hours of incubation in YGC broth. Dicloran was added to the oil phase to confine the growth of the hyphae in the aqueous phase.
Figure 51D:
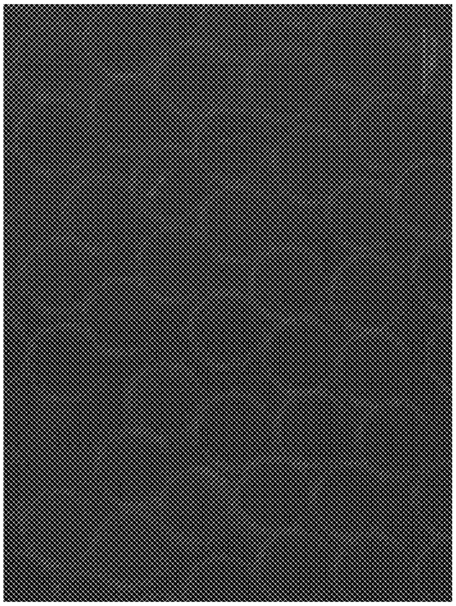
Figure 51A:
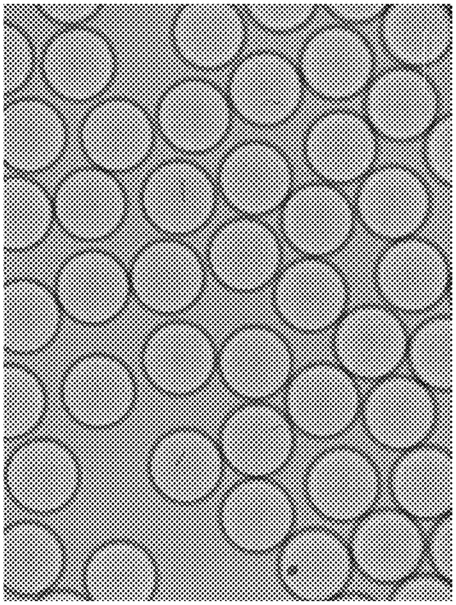
Figure 51C:
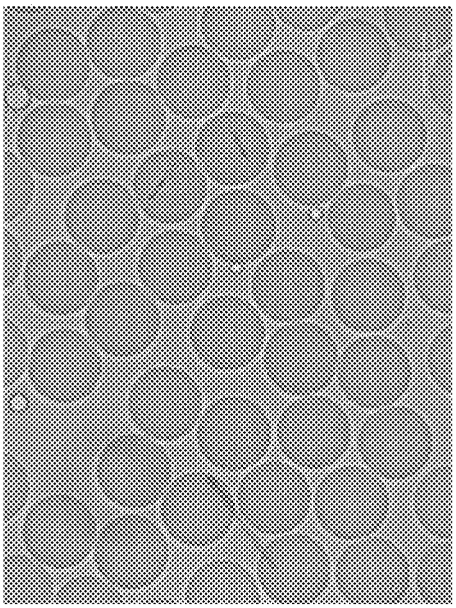
Figure 52A:
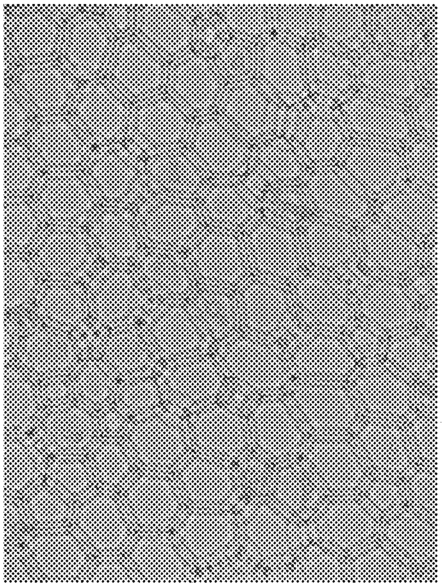
FIGS. 52A-52D illustrate the specific detection and/or enumeration of *Mucor racemosus* CECT 20821 in the absence (FIGS. 52A and 52B) and presence (FIGS. 52C and 52D), respectively, of 25 mg/L ALDOL® 515 Phosphate after 24 hours of incubation in YGC broth. Dicloran was added to the oil phase to confine the growth of the hyphae in the aqueous phase.
Figure 52B:
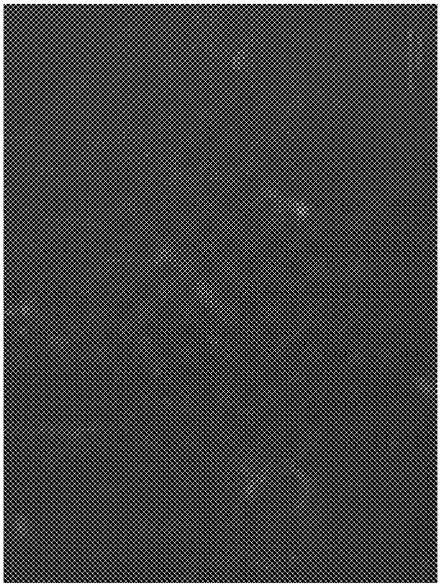
Figure 52C:
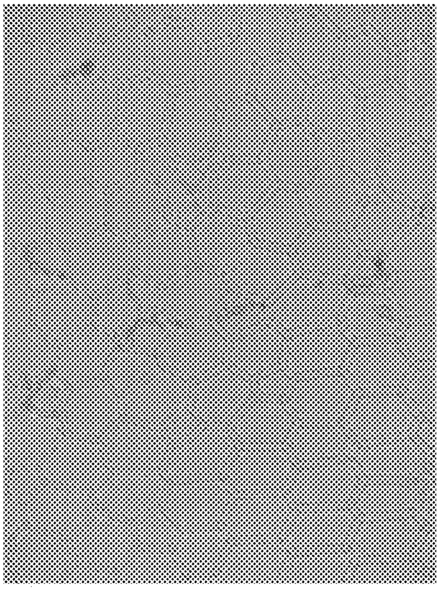
Figure 52D:

| Yeast Strain |
|---|
| *Candida albicans* ATCC 10231 (FIGS. 43A-43B) |
| *Candida tropicalis* ATCC 750 (FIGS. 49A-49B) |
| *Kluyveromyces lactis* CLIB 196 (FIGS. 44A-44B) |
| *Zygosaccharmyces rouxii* DSM 7525 (FIGS. 45A-45B) |
| *Saccharomyces cerevisiae* DSM 1333 (FIGS. 50A-50B) |
| Mold strain |
| *Mucor racemosus* CECT 20821 (FIGS. 46A-46D, 52A-52D) |
| *Eurotium rubrum* CECT 20808 (FIGS. 47A-47D) |
| *Fusarium graminearum* DSM 1096 (FIGS. 48A-48D, 51A-51D) |

| Droplet generation component | Reference | Supplier |
|---|---|---|
| Oil for Eva Green | 186-4006 | Bio-Rad |
| Pluronic F68 surfactant 10% | — | DBG |
| DG8 cartridge | 186-4008 | Bio-Rad |
| DG8 gasket | 186-3009 | Bio-Rad |
| TC20 counting slide | 1450011 | Bio-Rad |

Methods

The CFDA and the ALDOL®515 Phosphate substrates were dissolved in DMSO and added to YGC broth at the final concentration of 25 mg/L. Some experiments were also performed with 50 mg/L of ALDOL®515 Phosphate.

The concentration of DMSO was of 0.14% (v/v).

Cell suspensions were encapsulated at the concentration of $10^5$ cells or spores/ml in the YGC broth to reach the ratio of 1 positive droplet (containing 1 cell) out of 10. Droplet emulsions were prepared with Oil for Eva Green supplemented with dicloran for molds assays (to confine hyphae growth in the droplets).

The droplets were then transferred at 28° C. for 24 hours (FIGS. 43A-45B; 47A-47D; 49A-52D) or 48 hours (FIGS. 46A-46D; 48A-48D).

After incubation, droplet samples were observed under the ZOE™ Fluorescent Cell Imager for the detection of the esterase (CFDA hydrolysis) or phosphatase (ALDOL®515 Phosphate hydrolysis) activities.

Results: FIGS. 43A-48D show images of various strains of yeast and mold grown in the absence or presence of 25 mg/L CFDA. See the above table of yeast and mold strains for the figure having the given microorganism. In the absence of CFDA, no fluorescence was observed in droplets having yeast or mold growth. In the presence of CFDA, the esterase activity of the microorganism hydrolyzes the substrate and releases a fluorescent compound such that the droplets having yeast or mold growth produce green fluorescence, thereby demonstrating that a specific substrate can be used to identify the microorganism in droplets.

FIGS. 49A-52D show images of various strains of yeast and mold grown in the absence or presence of 50 mg/L ALDOL® 515 phosphate (FIGS. 49A-50B) or 25 mg/L ALDOL® 515 phosphate (FIGS. 52A-52D). See the above table of yeast and mold strains for the figure having the given microorganism. In the absence of ALDOL® 515 phosphate, no fluorescence was observed in droplets having yeast or mold growth. In the presence of ALDOL® 515 phosphate, the phosphatase activity of the microorganism hydrolyzes the substrate and releases a fluorescent compound such that the droplets having yeast or mold growth produce red fluorescence, thereby demonstrating that a specific substrate can be used to identify the microorganism in droplets.

18. Use of a Glucuronidase Substrate for Detection of *E. Coli*

Materials and Methods

A pepton-alginate-salt broth supplemented with resorufin-beta-D-glucuronic acid methyl Ester™ at 100 mg/L was spiked with *Escherichia coli* ATCC 25922.

Droplets were then produced with the Bio-Rad droplets generator and EvaGreen oil in order to obtain 1/10 of droplets containing 1 single bacterial cell.

Figure 53B:
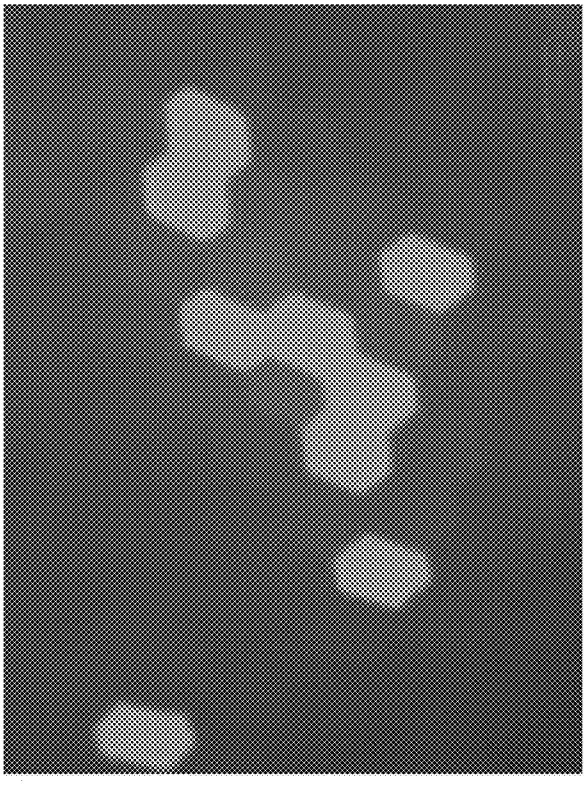
FIGS. 53A and 53B illustrate the use of a β-glucuronidase substrate for specific detection and/or enumeration of a target microorganism that expresses the β-glucuronidase enzyme. Droplets were formed from buffered peptone water broth spiked with *E. coli* ATCC 25922 in the absence (FIG. 53A) or presence (FIG. 53B) of resorufin-β-D-glucuronic.
Figure 53A:
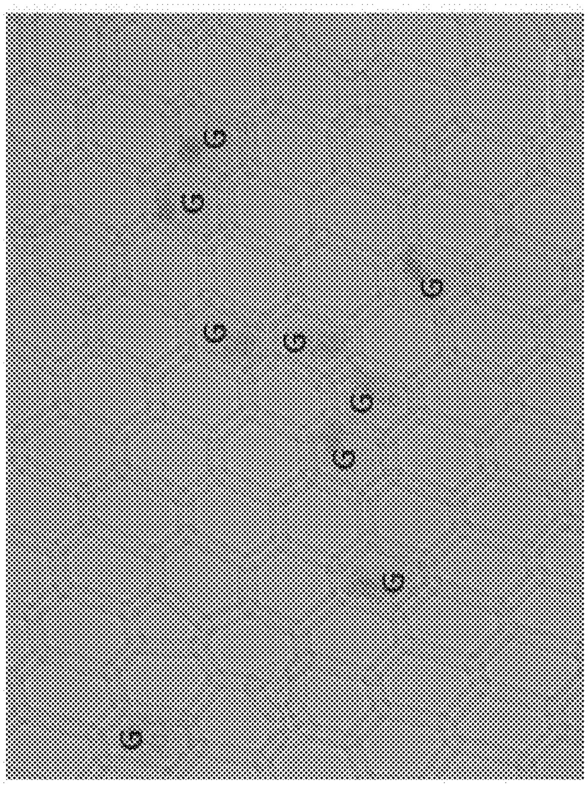

Droplets were incubated in a monolayer for 6 hours at 37° C. and then imaged with the ZOE™ Fluorescent Cell Imaging System using a bright-field channel (FIG. 53A) or using a red fluorescence filter (FIG. 53B).

Results: The droplets showing bacterial growth (G) produced a bright red fluorescence due to the cleavage of the resorufin-beta-D-glucuronic acid methyl Ester™ substrate by glucuronidase of the *E. Coli* strain. The demonstrates that a specific substrate can be used to identify the microorganism in droplets.

Although the foregoing invention has been described in some detail by way of illustration and example for purposes of clarity of understanding, one of skill in the art will appreciate that certain changes and modifications may be practiced within the scope of the appended claims. In addition, each reference provided herein, such as patents, patent applications, patent publications, journals, books, papers, and web contents throughout this disclosure, is incorporated by reference in its entirety and for all purposes to the same extent as if each reference was individually incorporated by reference. Where a conflict exists between the instant application and a reference provided herein, the instant application shall dominate.

As used in this specification and the appended claims, the singular forms “a”, “an”, and “the” include plural referents unless the content clearly dictates otherwise. As used herein, the term “about” refers to the recited number and any value within 10% of the recited number. Thus, “about 5” refers to any value between 4.5 and 5.5, including 4.5 and 5.5.

The invention claimed is:

1. A method for determining the presence or absence of a microorganism in a sample, the method comprising:

i) encapsulating a sample in a plurality of water-in-oil emulsion droplets wherein the water-in-oil emulsion droplets further encapsulate a microbiological growth medium;

ii) incubating the plurality of water-in-oil emulsion droplets at a temperature permissive of microbiological growth, and for a period of time sufficient to allow the target microorganisms to go through 5 to 45 doubling times;

iii) measuring autofluorescence, turbidity, an amount of a labeled microorganism binding agent and/or an intercalating dye in each of the water-in-oil emulsion droplets and identifying water-in-oil emulsion droplets comprising target microorganisms on the basis of autofluorescence, turbidity, signal of binding agent bound to the microorganism, and/or the presence of intercalating dye in the nucleic acids of the microorganism; and iv) responsive to identifying the target microorganism in at least one water-in-oil emulsion droplet, determining that the target microorganism is present in the sample, wherein the target microorganisms are selected from bacteria, yeasts and molds and wherein the incubating step is performed for a period of time corresponding to:

at least about 4 hours and no more than about 16 hours when the target microorganisms are bacteria;

at least about 6 hours and no more than about 12 hours when the target microorganisms are yeasts; and at least about 8 hours and no more than about 36 hours when the target microorganisms are molds.

2. The method of claim 1, wherein the incubating step is performed for a period of time corresponding to:

at least about 4 hours and no more than about 8 hours when the target microorganisms are bacteria;

at least about 8 hours and no more than about 12 hours when the target microorganisms are yeasts; and at least about 8 hours and no more than about 24 hours when the target microorganisms are molds.

3. The method of claim 1, wherein the oil phase of the water-in-oil emulsion droplets comprises an antifungal agent.

4. The method of claim 3, wherein the antifungal agent is selected from the group consisting of 2,6-dichloro-4-nitroaniline, 4,5,6,7-tetrachloro-2',4',5',7'-tetraiodofluorescein, (RS)-1-[2-(allyloxy)-2-(2,4-dichlorophenyl)ethyl]-1H-imidazole, and chitosan.

5. The method of claim 1, wherein the presence of microorganisms in the sample is determined by the detection of autofluorescence in the water-in-oil emulsion droplets comprising said sample.

6. The method of claim 1, wherein the presence of microorganisms in the sample is determined by the detection of turbidity in the water-in-oil emulsion droplets comprising said sample.

7. The method of claim 1, wherein the presence of microorganisms in the sample is determined by the detection of intercalated dye within the nucleic acids of microorganisms in the water-in-oil emulsion droplets comprising said sample.

8. The method of claim 1, wherein the presence of microorganisms in the sample is determined by the detection of labeled binding agent bound to microorganisms in the water-in-oil emulsion droplets comprising said sample.

9. The method of claim 1, wherein the sample is a food matrix, an environmental sample, or a clinical sample from a subject.

10. The method of claim 9, wherein the sample is an environmental sample.

11. The method of claim 9, wherein the sample is a clinical sample from a subject.

12. The method of claim 11, wherein the clinical sample is a blood sample, a plasma sample, a serum sample, a tissue sample, a urine sample, a sample of saliva, a pericardial sample, a pleural sample, a spinal fluid sample, a sputum sample, a bone marrow stem cell concentrate sample, a platelet concentrate sample, a nasal sample, a rectal sample, a vaginal sample, an inguinal swab, a sample from a wound, a skin sample, a sample from a mouth, tongue, or throat, an ascites sample, or a stool sample.

13. The method of claim 10, wherein the environmental sample is a sample from a surface or a water sample.

* * * * *